(12) United States Patent
Spiegel et al.

(10) Patent No.: US 12,312,621 B2
(45) Date of Patent: May 27, 2025

(54) REPROGRAMMING UROKINASE INTO AN ANTIBODY-RECRUITING ANTICANCER AGENT

(71) Applicant: YALE UNIVERSITY, New Haven, CT (US)

(72) Inventors: David A. Spiegel, New Haven, CT (US); Charles E. Jakobsche, Worcester, MA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 18/243,169

(22) Filed: Sep. 7, 2023

(65) Prior Publication Data

US 2024/0067952 A1    Feb. 29, 2024

Related U.S. Application Data

(60) Continuation of application No. 17/182,437, filed on Feb. 23, 2021, now Pat. No. 11,920,172, which is a division of application No. 16/149,299, filed on Oct. 2, 2018, now Pat. No. 10,961,527, which is a continuation of application No. 14/356,820, filed as application No. PCT/US2012/063844 on Nov. 7, 2012, now abandoned.

(60) Provisional application No. 61/558,811, filed on Nov. 11, 2011.

(51) Int. Cl.
| | |
|---|---|
| C12N 9/96 | (2006.01) |
| A61K 31/165 | (2006.01) |
| A61K 31/352 | (2006.01) |
| A61K 31/365 | (2006.01) |
| A61K 38/05 | (2006.01) |
| A61K 38/48 | (2006.01) |
| A61K 45/06 | (2006.01) |
| A61K 47/54 | (2017.01) |
| A61K 47/60 | (2017.01) |
| C07C 279/12 | (2006.01) |
| C07D 491/107 | (2006.01) |
| C07D 493/10 | (2006.01) |
| C07K 5/062 | (2006.01) |

(52) U.S. Cl.
CPC .............. *C12N 9/96* (2013.01); *A61K 31/165* (2013.01); *A61K 31/352* (2013.01); *A61K 31/365* (2013.01); *A61K 38/05* (2013.01); *A61K 38/482* (2013.01); *A61K 45/06* (2013.01); *A61K 47/54* (2017.08); *A61K 47/60* (2017.08); *C07C 279/12* (2013.01); *C07D 491/107* (2013.01); *C07D 493/10* (2013.01); *C07K 5/06026* (2013.01)

(58) Field of Classification Search
CPC .......... C12N 9/96; A61K 47/54; A61K 47/60; A61K 31/165; A61K 31/352; A61K 31/365; A61K 38/05; A61K 38/482; A61K 45/06; C07C 279/12; C07D 491/107; C07D 493/10; C07K 5/06026

USPC .......................................................... 424/450
See application file for complete search history.

(56) References Cited

U.S. PATENT DOCUMENTS

| | | | |
|---|---|---|---|
| 6,242,173 B1 | 6/2001 | Mann | |
| 6,610,269 B1 | 8/2003 | Klaveness et al. | |
| 8,859,509 B2 | 10/2014 | Spiegel | |
| 9,181,224 B2 | 11/2015 | Spiegel | |
| 10,961,527 B2 * | 3/2021 | Spiegel | A61K 31/365 |
| 11,920,172 B2 * | 3/2024 | Spiegel | C07D 493/10 |
| 2002/0147136 A1 | 10/2002 | Von Wronski | |
| 2007/0212305 A1 | 9/2007 | Klaveness et al. | |
| 2008/0019907 A1 | 1/2008 | Klaveness et al. | |
| 2008/0044350 A1 | 2/2008 | Klaveness et al. | |
| 2013/0245040 A1 | 9/2013 | Spiegel | |
| 2015/0018395 A1 | 1/2015 | Spiegel | |

(Continued)

FOREIGN PATENT DOCUMENTS

| | | |
|---|---|---|
| WO | 2011046946 | 4/2011 |
| WO | 2012068366 | 5/2012 |
| WO | 2013162757 | 10/2013 |

(Continued)

OTHER PUBLICATIONS

Ellis V, Pyke C, Eriksen J, Solbrg H and Dano K; The Urokinase Receptor: Involvement in Cell Surface Proteolysis and Cancer Invasion. Annals of the New York Academy of Sciences, 1992; vol. 667, pp. 13-31. doi:10.1111/j.1749-6632.1992.tb51591.

(Continued)

*Primary Examiner* — Yih-Horng Shiao
(74) *Attorney, Agent, or Firm* — Henry D. Coleman; R. Neil Sudol

(57) ABSTRACT

The present invention relates to chimeric (preferably, bifunctional) compounds, compositions comprising those compounds and methods of treating cancer in a patient or subject, especially including metastatic cancer where cancer cells exhibit overexpression (heightened expression) of cell surface urokinase-type plasminogen activator receptor (urokinase receptor) compared to normal (non-cancerous) cells. The compounds preferably covalently bind to the urokinase receptor and recruit native antibodies of the patient or subject where the antibodies can selectively degrade and/or deactivate targeted cancer cells through antibody-dependent cellular phagocytosis and/or antibody-dependent cellular cytotoxicity (ADCC) against a large number and variety of cancers, thus providing cancer cell death and/or an inhibition of growth, elaboration and/or metastasis of the cancer, including remission and cure of the patient's cancer.

20 Claims, 26 Drawing Sheets

(56) References Cited

U.S. PATENT DOCUMENTS

| | | |
|---|---|---|
| 2015/0087609 A1 | 3/2015 | Spiegel |
| 2015/0110742 A1 | 4/2015 | Spiegel |

FOREIGN PATENT DOCUMENTS

| | | |
|---|---|---|
| WO | 2013166110 A1 | 11/2013 |
| WO | 2014178878 | 11/2014 |

OTHER PUBLICATIONS

Glossary of medical education terms. Institute of International Medical Education. http:// www.lime.org/glossary.htm Accessed in Mar. 2013.
Rullo et al.; Re-engineering the Immune Response to Metastatic Cancer: Antibody-Recruiting Small Molecules Targeting the Urokinase Receptor. Angew. Chem. Int. Ed., 2016; vol. 55, pp. 3642-3646.
Murphy, et al. A modified Tat peptide for selective intracellular delivery of macromolecules. J Pharm Pharmacol, 2011;63(5):611-618.
Kettner, et al. The Susceptibility of Urokinase to Affinity Labeling by Peptides of Arginine Chloromethyl Ketone. Biochimica et Biophysica Acta, 1979;569:31-40.
Rush, et al. New Aldehyde Tag Sequences Identified by Screening Formylglycine Generating Enzymes in Vitro and in Vivo. J Am Chem Soc, 2008;130:12240-12241.
Mazitschek, et al. Inhibitors of angiogenesis and cancer-related receptor tyrosine kinases. Current Opinion in Chemical Biology, 2004;8:432-441.
Jemal A, et al. Cancer statistics 2010. CA Cancer J. Clin, 2010;60:277-300.
Garbe C, et al.(2011) Systematic review of medical treatment in melanoma: current status and future prospects. The Oncologist, 2011;16:5-24.
Boyle P, Levin B. World Cancer Report 2008. International Agency for Research on Cancer, Lyon, 2008:438-443.
Andreasen PA, et al. The urokinase-type plasminogen activator system in cancer metastasis: A review. Int. J. Cancer, 1997;72:1-22.
Duffy MJ. Urokinase-type plasminogen activator and malignancy. Fibrinolysis, 1993;7:295-302.
Saksela O, Rifkin DB. Cell-associated plasminogen activation: Regulation and physiological functions. Ann. Rev. Cell. Biol, 1988;4:93-126.
Del Rosso M, et al. Multiple pathways of cell invasion are regulated by multiple families of serine proteases. Clin. & Exp. Metastasis, 2002;19:193-207.
Jessani N, et al. Enzyme activity profiles of the secreted and membrane proteome that depict cancer cell invasiveness. Proc. Natl. Acad. Sci. U.S.A, 2002;99:10335-10340.
Romer J, Nielsen BS, Ploug M. The Urokinase Receptor as a Potential Target in Cancer Therapy. Current Pharmaceutical Design, 2004;10:2359-2376.
Blasi F, Carmeliet P. uPAR: A Versatile Signalling Orchestrator. Nature, 2002;3:932-943.
Duffy MJ. Proteases as prognostic markers in cancer. Clinical Cancer Research, 1996;2:613-618.
Dano K, et al. The Urokinase Receptor. Protein Structure and Role in Plasminogen Activation and Cancer Invasion. Fibrinolysis, 1994;8 Suppl 1:189-203.
Quax Pha, et al. Metastatic Behavior of Human Melanoma Cell Lines in Nude Mice Correlates with Urokinase-Type Plasminogen Activator, its Type-1 Inhibitor, and Urokinase-mediated Matrix Degradation. The Journal of Cell Biology, 1991;115(1):191-199.
Madsen MA, et al. Enzyme Catalysis and Regulation: Activity-based Protein Profiling Implicates Urokinase Activation as a Key Step in Human Fibrosarcoma Intravasation. J Biol Chem, 2006;281:15997-16005.
Sier CFM, et al. The Level of Urokinase-type Plasminogen Activator Receptor Is Increased in Serum of Ovarian Cancer Patients. Cancer Res, 1998;58:1843-1849.
Harbeck N, et al. Urokinase-type plasminogen activator (uPA) and its inhibitor PAI-I: novel tumor-derived factors with a high prognostic and predictive impact in breast cancer. Thromb Haemost, 2004;91:450-456.
Duffy MJ, et al. Urokinase-Plasminogen Activator, a Marker for Aggressive Breast Carcinomas. Cancer, 1988;62:531-533.
Herszenyi L, et al. The Role of Cysteine and Serine Proteases in Colorectal Carcinoma. Cancer, 1999;86(7):1135-1142.
Harvey SR, et al. Evaluation of Urinary Plasminogen Activator, Its Receptor, Matrix Metalloproteinase-9, and von Willebrand Factor in Pancreatic Cancer. Clin Cancer Res, 2003;9:4935-4943.
Konecny G, et al. Association of Urokinase-Type Plasminogen Activator and Its Inhibitor with Disease Progression and Prognosis in Ovarian Cancer. Clin Cancer Res, 2001;7:1743-1749.
Schmitt M, et al. The urokinase plasminogen activator system as a novel target for tumour therapy. Fibrinolysis & Proteolysis, 2000;14:114-132.
Ertongur S, et al. Inhibition of the Invasion Capacity of Carcinoma Cells by WX-UK1, a Novel Synthetic Inhibitor of the Urokinase-Type Plasminogen Activator System. Int J Cancer, 2004;110:815-824.
Ossowski L, Reich E. Antibodies to Plasminogen Activator Inhibit Human Tumor Metastasis. Cell, 1983;35:611-619.
Liu S, et al. Potent antitumor activity of a urokinase-activated engineered anthrax toxin. PNAS, 2003;100(2):657-662.
Min HY, et al. Urokinase Receptor Antagonists Inhibit Angiogenesis and Primary Tumor Growth in Syngeneic Mice. Cancer Res, 1996;56:2428-2433.
Vallera DA, et al. Targeting Urokinase-Type Plasminogen Activator Receptor on Human Glioblastoma Tumors With Diphtheria Toxin Fusion Protein DTAT. Journal of the National Cancer Institute, 2002;94(8):597-606.
Spiegel DA. Synthetic immunology to engineer human immunity. Nature Chemical Biology, 2010;6:871-872.
Murelli RP, et al. Chemical Control over Immune Recognition: A Class of Antibody-Recruiting Small Molecules That Target Prostate Cancer. J Am Chem Soc, 2009;131:17090-17092.
Lu Y, Low PS. Folate targeting of haptens to cancer cell surfaces mediates immunotherapy of syngeneic murine tumors. Cancer Immunol Immunother, 2002;51:153-162.
Lu Y, Sega E, Low PS. Folate receptor-targeted immunotherapy: induction of humoral and cellular immunity against hapten-decorated cancer cells. Int J Cancer, 2005;116:710-719.
Popkov M, et al. Instant Immunity through Chemically Programmable Vaccination and Covalent Self-Assembly. PNAS, 2009;106(11):4378-4383.
Carlson CB, et al. Selective Tumor Cell Targeting Using Low-Afinity, Multivalent Interactions. ACS Chemical Biology, 2007;2(2):119-127.
Ortega E, et al. Natural DNP-Binding Immunoglobulins and Antibody Multispecificity. Molecular Immunology, 21(10):883-888 (year 1984).
Kettner C, Shaw E. Inactivation of Trypsin-Like Enzymes with Peptides of Arginine Chloromethyl Ketone. Methods in Enzymology, 1981;80:826-842.
Spraggon G, et al. The crystal structure of the catalytic domain of human urokinase-type plasminogen activator. Structure, 1995;3:681-691.
Williams EB, et al. Zymogen/Enzyme Discrimination Using Peptide Chloromethyl Ketones. The Journal of Biological Chemistry, 1989;264(13):7536-7545.
Walker B, Elmore DT. The Behaviour of Urokinase and Porcine Kidney Cell Plasminogen Activator Towards Some Synthetic Peptides. Thrombosis Research, 1984;103-107.
Binnema DJ, et al. Quantitation of Urokinase Antigen in Plasma and Culture Media by Use of an ELISA. Thrombosis Research, 1986;43:569-577.

(56) References Cited

OTHER PUBLICATIONS

Rajagopal V, Kreitman RJ. Recombinant Toxins That Bind to the Urokinase Receptor Are Cytotoxic without Requiring Binding to the alpha2-Macroglobulin Receptor. J Biol Chem, 2000;275:7566.

Bracher M, et al. Three-colour flow cytometric method to measure antibody-dependent tumour cell killing by cytotoxicity and phagocytosis. Journal of Immunological Methods, 2007;323:160-171.

Boltz-Nitulescu G, et al. Modulation of IGA, IGE, and IgG Fc receptor expression on human mononuclear bhagocytes by 1alpha,25-dihydroxyvitamin D3 and cytokines, J. Leukoc. Biol. 58:256-262, 1995.

Lu Y, et al. Strategy to Prevent Drug-Related Hypersensitivity in Folate-Targeted Hapten Immunotherapy of Cancer. The AAPS Journal, 2009;11(3):628-638.

Kute TE, et al. Breast tumor cells isolated from in vitro resistance to trastuzumab remain snesitive to trastuzumab anti-tumor effects in vivo and to ADCC killing. Cancer Immunol Immunother, 2009;58:1887-1896.

Zhu J, et al. Dynamic and label-free monitoring of natural killer cell cytotoxic activity using electronic sensor arrays. Journal of Immunological Methods, 2006;309:25-33.

Weiner GJ. Monoclonal antibody mechanisms of action in cancer. Immunol Res, 2007;39:271-278.

Harris TD, et al. Structure-Activity Relationships of 111In- and 99mTc-Labeled Quinolin-4-one Peptidomimetics as Ligands for the Vitronectin Receptor: Potential Tumor Imaging Agents. Bioconjugate Chem, 2006; 17:1294-1313.

Sakakibara S, Inukai N. A New Reagent for the p-Nitrophenylation of Carboxylic Acids. Short Communications, 1964;37(8):1231-1232.

Rueping M, et al. Design, Synthesis and Structural Investigations of a beta-Peptide Forming a 3(14)-Helix Stabilized by Electrostatic Interactions. Chem Eur J, 2004;10:1607-1615.

Yu N, et al. Real-Time Monitoring of Morphological Changes in Living Cells by Electronic Cell Sensor Arrays: An Approach to Study G Protein-Coupled Receptors. Anal Chem, 2006;78:35-43.

* cited by examiner

Compound 1

Compound 2

Compound 3

REPROGRAMMING UROKINASE INTO AN ANTIBODY-RECRUITING ANTICANCER AGENT

RELATED APPLICATIONS AND GRANT SUPPORT

This application is a divisional application of U.S. application Ser. No. 17/182,437, filed on Feb. 23, 2021, which is a divisional application of U.S. application Ser. No. 16/149,299 filed on Oct. 2, 2018, which is a continuation application of United States national phase patent application Ser. No. 14/356,820 of 371 Filing Date May 7, 2014, which is a United States national phase patent application based on International Patent Application No. PCT/US12/63844 of international filing date Nov. 7, 2012, entitled "Reprogramming Urokinase Into an Antibody-Recruiting Anticancer Agent", which claims the benefit of priority of United States provisional application U.S. 61/558,811, filed Nov. 11, 2011, entitled
"ARM-U: Reprogramming urokinase to serve as an antibody-recruiting anticancer agent", the entire contents of which each of said related applications is incorporated by reference.

This invention was made with government support under 1DP2OD002913-01 awarded by the National Institute of Health. The government has certain rights in the invention.

FIELD OF THE INVENTION

The present invention relates to chimeric (including bifunctional) compounds, compositions comprising those compounds and methods of treating cancer in a patient or subject, especially including metastatic cancer where cancer cells exhibit overexpression (heightened expression) of cell surface urokinase-type plasminogen activator receptor (urokinase receptor) compared to normal (non-cancerous) cells. The compounds preferably covalently bind to the urokinase-type plasminogen activator (uPA) on the surface of a cancer cell, including a metastatic cancer cell, and consequently recruit native antibodies of the patient or subject where the antibodies can selectively degrade and/or deactivate targeted cancer cells through antibody-dependent cellular phagocytosis and antibody-dependent cellular cytotoxicity (ADCC) and/or complement dependent cytotoxicity (CDC) against a large number and variety of cancers, thus providing cancer cell death and an inhibition of growth, elaboration and/or metastasis of the cancer, including remission and cure of the patient's cancer.

BACKGROUND OF THE INVENTION

Cancer is currently the second leading cause of death in the United States, having claimed over half a million American lives in 2010.[i] In general, metastatic cancers are particularly difficult to treat and are associated with higher levels of morbidity and mortality compared to localized tumors.[ii,iii] For example, while the five-year survival rate of patients with localized melanoma is >95%, this survival rate drops to 15-30% for patients whose disease has metastasized to distant locations.[i] Since American men and women have a 38-44% chance, respectively, of developing invasive cancers during their lifetimes,[i] novel strategies for treating advanced-stage invasive cancers have the potential to provide profound therapeutic impact.

Tumor metastasis begins with cancer cells invading surrounding tissues. This process is frequently accelerated by cell-surface proteases, including uPA,[iv,v,vi] which are capable of breaking down extracellular matrix proteins and activating migration-inducing signal transduction cascades.[vii,viii] uPA binds uPAR on the extracellular surface of many cancer cells, including those of the breast, colon, stomach, and bladder.[ix,x] Extensive evidence suggests that the levels of uPA and uPAR expression are substantially higher on invasive, malignant cancer cells than on either healthy tissues or benign Indeed, in clinical settings, high levels of uPA and uPAR are used as diagnostic markers for metastatic potential and poor clinical outcome in numerous malignancies.[iv,v,x,xv,xvi,xvii,xviii,xix,xx] For these reasons uPA and uPAR have emerged as promising therapeutic targets.[ix,xxi] Data has shown that inhibitors and cytotoxic fusion proteins that target the uPA-uPAR system can both reduce the invasive potential of cancer cells[xxii,xxiii] and reduce tumor volumes in animal models[xxiv,xxv,xxvi] without significantly damaging healthy tissue.[xxvi]

The growing field of synthetic immunology[xxvii] aims to develop novel synthetic materials capable of modulating the human immune system. One emerging concept in this area is to use bifunctional molecules to direct normal immune responses to attack cancer cells that are not sufficiently recognized and suppressed by the immune system on its own.[xxviii,xxix,xxx,xxxi,xxxii] We report here a novel application of this strategy to direct endogenous immunological effector mechanisms to act against uPAR-expressing human cancer cells (FIG. 1). We have designed and synthesized two small molecules that can convert uPA into catalytically inactive, bifunctional constructs (ARM-Us) that are capable of both recruiting antibodies and directing antibody-dependent immune responses against uPAR-expressing cancer cells. These small molecules quantitatively inhibit uPA's enzymatic activity by covalently binding to its active site, and this covalent modification simultaneously appends either a 2,4-dinitrophenyl (DNP) moiety or a fluorescein label. The DNP antigen is of particular interest for therapeutic application because anti-DNP antibodies have been found endogenously in the plasma of most humans.[xxxiii] Here we demonstrate that ARM-U can bind with high affinity to uPAR-expressing cancer cells, recruit antibodies to these cells, and induce phagocytosis and cytotoxicity in an antibody-dependent immune-mediated fashion. The technology reported herein represents a novel strategy to target uPAR-expressing cancers and has significant potential to impact the treatment of a variety of deadly malignancies.

BRIEF DESCRIPTION OF THE INVENTION

The present invention is directed to a compound (also referred to as a precursor compound or ARM-U precursor compound) according to the formula:

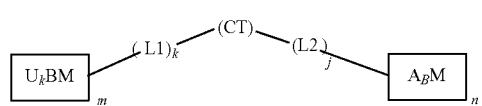

Where

is a moiety which covalently or non-covalently (preferably covalently) binds to an active site of urokinase-type plasminogen activator (uPA) on the surface of cancer cells of a patient or subject;

$$A_BM$$

is an antibody binding moiety comprising a hapten which is capable of binding to an antibody in said patient or subject;
L1 is a linker molecule which chemically links $$U_kBM$$

to CT, L2 or $$A_BM$$

in said compound;
L2 is a linker molecule which chemically links $$A_BM$$

to CT, L1 or $$U_kBM$$

in a molecule;
CT is a bond or a connector molecule which links L1 and/or L2 to $$U_kBM$$

and/or $$A_BM;$$

Each j is independently 0, 1, 2, 3, 4 or 5 (preferably 0 or 1, more preferably 1);
Each k is independently 0, 1, 2, 3, 4 or 5 (preferably 0 or 1, more preferably 1), with the proviso that k and/or j are other than 0 when CT is a bond; and
Each m and n is independently an integer from 1 to 15, 1 to 10, 1 to 5, 1 to 3, 2 to 3, 2 to 5, 1 to 2 or 1 (preferably m and n are each 1),
or a pharmaceutically acceptable salt, solvate or polymorph thereof.

In further aspects of the present invention, precursor compounds (as described above or otherwise as described herein) are reacted or complexed with urokinase-type plasminogen activator (UPA) according to the present invention to provide ARM-U compounds represented by the chemical formula:

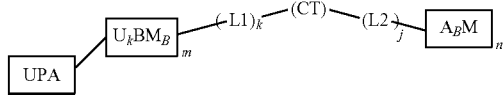

Where UPA is urokinase-type plasminogen activator (UPA) as otherwise described herein, $$U_kBM_B$$

is a

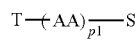

group which has covalently or non-covalently (preferably covalently bound) to UPA and each of $$U_kBM,$$

L1, CT, L2, $$A_BM,$$

j, k, m and n is the same as above or as otherwise described herein.

In certain embodiments of the present invention, compounds according to the present invention (i.e., compounds which are unbound to UPA or are precursors to compounds which are bound to UPA) may be represented by the chemical formula:

$$T-(AA)_{p1}-S$$

Where T is group which binds to UPA, preferably covalently, and is preferably a $R^e$ group or an amino acid group according to the chemical structure:

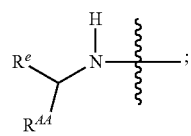

$R^{AA}$ is a sidechain of an amino acid, preferably a side chain of lysine or arginine

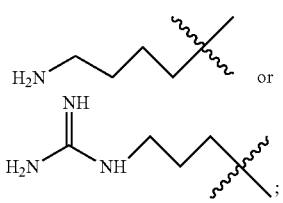

$R^e$ is H (resulting in non-covalent binding to UPA) or an electrophilic group which reactive with a nucleophile in the active site of uPA to produce a covalent bond (preferably on a histidine residue within the active site of UPA), preferably an electrophilic group according to the chemical formula:

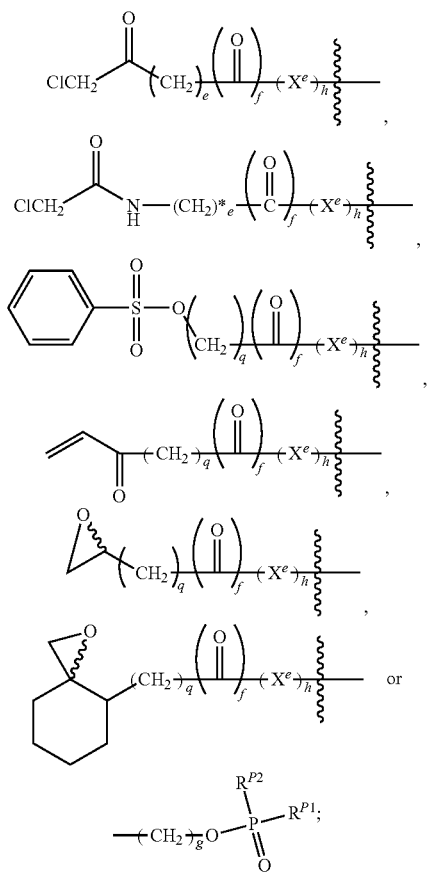

Where $X^e$ is O, S, or N—$R^{Xe}$;

$R^{Xe}$ is H or a $C_1$-$C_3$ alkyl or alkanol group;

$R^{P1}$ is any group which forms a stable linkage with the phosphate moiety, and is an optionally substituted hydrocarbyl group, often an optionally substituted $C_1$-$C_{12}$ alkyl group (preferably methyl), an optionally substituted aromatic or heterocyclic group (preferably, an optionally substituted phenyl group or a heteroaryl group which is a 5-6 membered ring);

$R^{P2}$ is a halogen (preferably F or Cl, most often F because of its reduced reactivity in aqueous solutions such as water/buffer solution)

Each e is independently 0, 1, 2, 3, 4, 5 or 6;
Each f is independently 0 or 1 (often 0); and
Each g is 0, 1, 2, 3, 4, 5 or 6 (often 1);
Each h is independently 0 or 1;
Each q is independently 1, 2, 3, 4, 5, or 6

Each (AA) is independently a single amino acid residue or if $p_1$ is more than 1, forms a polypeptide (i.e., an amino acid containing residue comprising at least two amino acids linked together through peptide bond(s)), the amino acid is often glycine, alanine, serine, threonine, leucine, isoleucine, lysine, aspartic acid or glutamic acid, is most often alanine or glycine, but may be any amino acid as otherwise described here);

$p_1$ is an integer from 0 to 25 (including all integers within that range), often 0 to 10 (preferably 1-6, 1, 2, 3, 4, 5, or 6) and S is

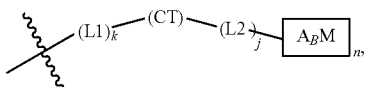

Where L1, CT, L2,

k, j and n are as otherwise described herein, or a pharmaceutically acceptable salt, enantiomer, solvate or polymorph thereof. In certain preferred aspects (AA)$p_1$ is an glycine (or alanine)-glutamic acid (or aspartic acid) dipeptide linked ot arginine (or lysine) with the arginine or lysine functioning as the terminal end of the compound (to which is linked an $R^e$ group) and the glutamic acid group linking the $U_k$BM group to the linker group (alternatively, one could also readily use aspartic acid, a lysine group or serine group to link the linker group to the $U_k$BM group and to provide additional functionality, although any amino acid could be used). Pursuant to an embodiment of the invention, these precursor compounds may be covalently or non-covalently bound to UPA to provide UPA complexed (ARM-U) compounds according to the present invention. These ARM-U compounds are the preferred compounds for administration to patients in order to treat cancer, especially including metastatic cancer.

In further embodiments according to the present invention, further precursor compounds according to the present invention relate to a chemical composition according to the chemical formula:

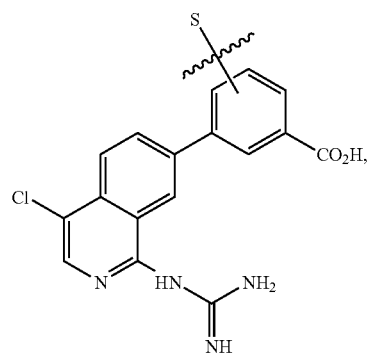

-continued

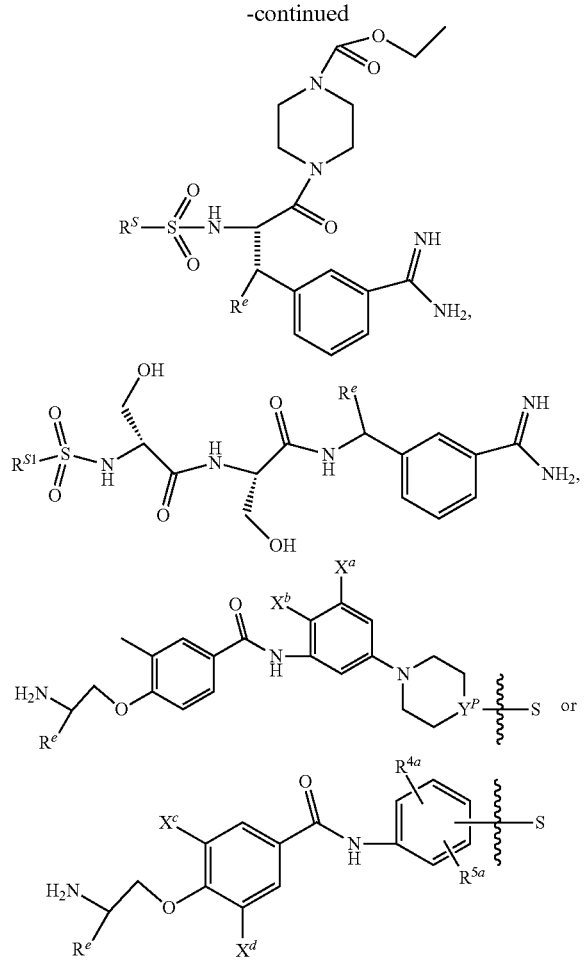

Where $R^e$ is the same as above (i.e., H or an electrophilic group as described, preferably, a chloromethylketone group);

$R^S$ is S or a group;

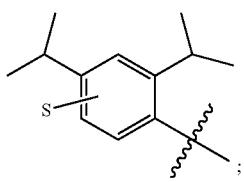

$R^{S1}$ is S or a group;

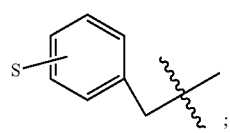

$Y^P$ is N or $CH_2$;

$X^a$ is H, a halogen (preferably F or Cl), a $C_1$-$C_3$ alkyl group (preferably methyl) or a —O—($C_1$-$C_3$ alkyl group), preferably $X^a$ is F, Cl or $CH_3$ (more often F or Cl);

$X^b$ is H, a halogen (preferably F or Cl), a $C_1$-$C_3$ alkyl group or a —O—($C_1$-$C_3$ alkyl group), preferably $X^b$ is H or O-Et;

$X^c$ and $X^d$ are each independently H, a halogen (preferably F or Cl), a $C_1$-$C_3$ alkyl group (often $CH_3$) or a —O—($C_1$-$C_3$ alkyl group), preferably Cl or $CH_3$, more preferably Cl and $CH_3$;

$R^{4a}$ and $R^{5a}$ are each independently H, a halogen (preferably F or Cl), a $C_1$-$C_3$ alkyl group (often $CH_3$) or a —O—($C_1$-$C_3$ alkyl group), preferably H, OMe, OEt or OiPr; and S (as a group) is

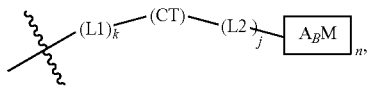

Where L1, CT, L2,

k, j and n are as otherwise described herein or a pharmaceutically acceptable salt thereof. In further embodiments, these compounds are covalently or non-covalently bound to UPA through the

group.

In certain preferred embodiments, L1 and/or L2 are (poly)ethylene glycol groups comprising from 1 to 25, from 1 to 15, from 1 to 12, from 2 to 11, 2 to 10, 2 to 8, 2 to 6, 2 to 5, 2 to 4 and 2 to 3 ethyleneglycol groups, which may be linked to

CT and/or

groups. In certain aspects of the invention, the connector group CT, when present, is a triazole group or an amide group. In certain embodiments, the

group is a dinitrophenyl (DNP) or fluorescein group as described in greater detail herein.

In preferred aspects of the invention

is a

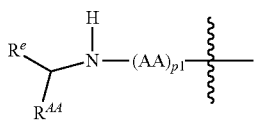

group, where $R^{AA}$ is a sidechain of an amino acid, preferably a side chain of lysine or arginine

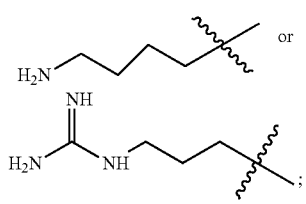

and $R^e$ is an electrophilic group according to the chemical formula:

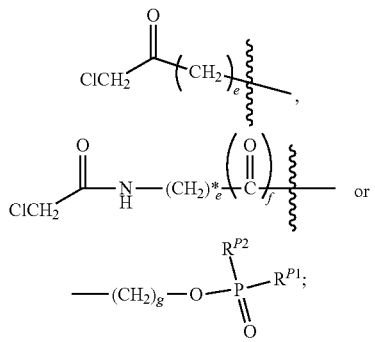

Where $R^{P1}$ is $C_1$-$C_6$ alkyl (preferably methyl);

$R^{P2}$ is a halogen (preferably F or Cl, more preferably F)

e is 0, 1, 2, 3, 4 or 5 (preferably, 0);

f is 0 or 1 (preferably 0); and g is 0, 1, 2, or 3 (preferably 1);

(AA) is a single amino acid residue or polypeptide (i.e., an amino acid containing residue comprising at least two amino acids linked together through peptide bond (s)) (the amino acid is often glycine, alanine, serine, threonine, leucine or isoleucine, is most often alanine or glycine, often alanine and glycine together, but may be any amino acid as otherwise described here); and $p_1$ is an integer from 0 to 10 (preferably 1-6, 1-3, 1-2, 2-6), or a pharmaceutically acceptable salt thereof.

In certain embodiments,

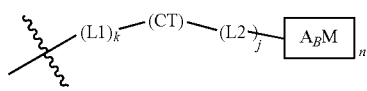

may be represented by the following structure (n is 1):

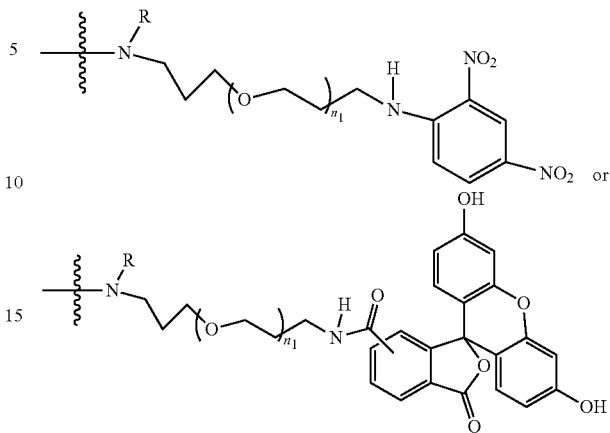

Where $n_1$ is from 1 to 12, 1 to 10, 1 to 6, 1, 2, 3, 4, or 5.

Preferred chimeric compounds are presented in attached FIG. 6, hereof.

In an additional aspect of the invention, a pharmaceutical composition comprises an effective amount of a chimeric (which term includes bifunctional) compound as described above, optionally and preferably in combination with a pharmaceutically acceptable carrier, additive or excipient. In alternative aspects, pharmaceutical combination compositions comprise an effective amount of a chimeric compound as described herein, in combination with at least one additional agent which is used to treat cancer, including metastatic cancer; or a secondary condition or effect of cancer, especially metastatic cancer or alternative secondary effect, including one or more of bone pain, hyperplasia, osteoporosis, kidney failure, liver failure, etc., as otherwise described herein.

In a further aspect of the invention, compounds according to the present invention are used to treat cancer in a patient. The method of treating cancer comprises administering to a patient in need an effective amount of a chimeric compound as otherwise described herein in combination with a pharmaceutically acceptable carrier, additive or excipient, optionally in further combination with at least one additional agent which is effective in treating cancer, including metastatic cancer, or one or more of its secondary conditions or effects.

The present invention also relates to a method for inhibiting cancer to reduce the likelihood or inhibit the spread or metastasis of the cancer into other tissues of the patients' body for any cancer, and especially such cancers including bone, lymph (lymph nodes), bladder, vas deferens, kidneys, liver, lungs, pancreas, brain, prostate and ovaries, among others.

Pursuant to the present invention, synthetic compounds for controlling or creating human immunity pursuant to the present invention have the potential to revolutionize disease treatment. Motivated by challenges in this arena, the present inventors provide a strategy to target metastatic cancer cells for immune-mediated destruction by targeting the urokinase-type plasminogen activator receptor (uPAR). Urokinase-type plasminogen activator (uPA) and uPAR are overexpressed on the surfaces of a wide range of invasive cancer cells and are believed to contribute substantially to the migratory propensities of these cells. The key component of the approach is an antibody-recruiting molecule that targets the urokinase receptor (ARM-U). This bifunctional construct is formed by selectively, covalently attaching an antibody-binding small molecule to the active site of the urokinase enzyme (uPA) to produce ARM-U compounds. The present inventors demonstrate that ARM-U is capable of redirecting antibodies to the surfaces of target cancer cells and mediating both antibody-dependent cellular phagocytosis (ADCP) and antibody-dependent cellular cytotoxicity (ADCC) against multiple human cancer cell lines. The present invention represents a novel technology has significant potential to impact the treatment of a variety of deadly, invasive cancers.

DETAILED DESCRIPTION OF THE INVENTION

Figure 1:
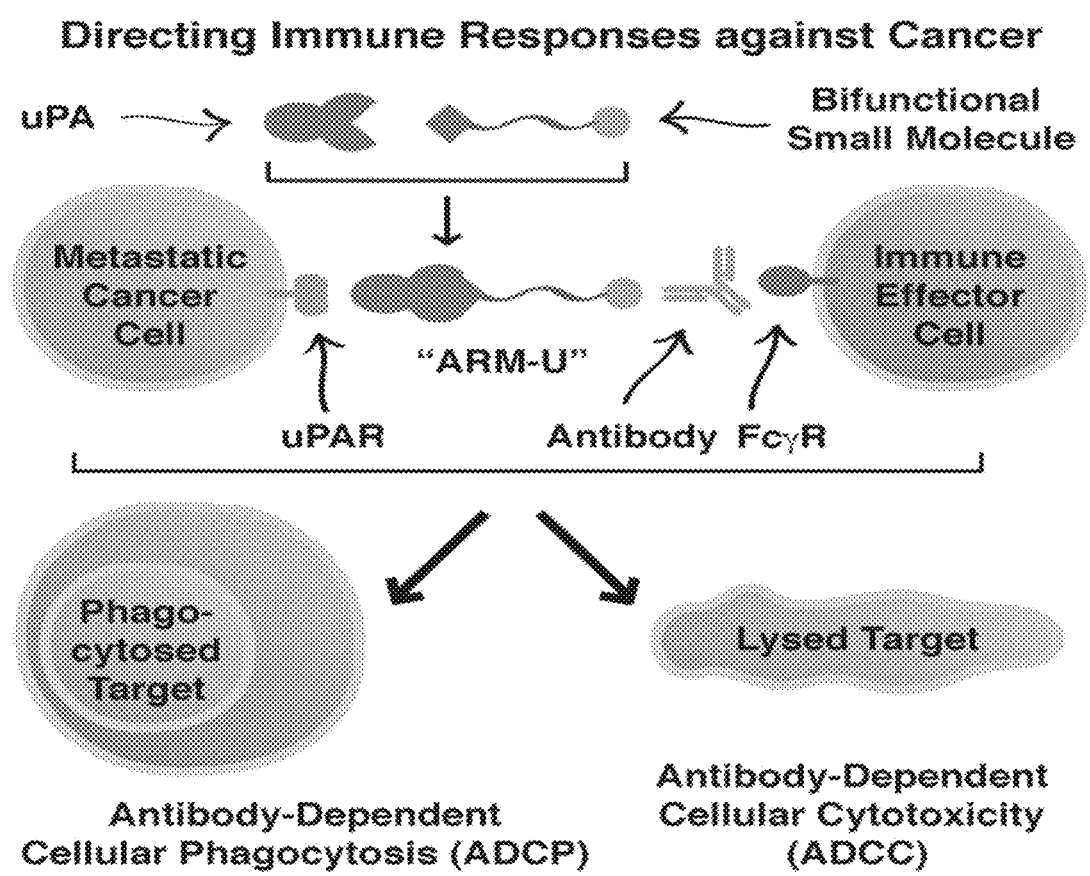
FIG. 1 provides an overview of using bifunctional ARM-U complexes to direct natural immune responses against uPAR-expressing cancer cells.

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, within context, to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder. Active chimeric compounds which have been reacted or complexed with urokinase-type plasminogen activator according to the present invention may collectively be referred to as ARM-U compounds, as well as difunctional compounds. Particular compounds may be precursor compounds or "precursors", i.e., compounds which are capable of covalently or non-covalently binding to urokinase-type plasminogen activator (uPA), or compounds which have covalently or non-covalently been bound to uPA (ARM-U compounds where precursor compounds are complexed/bound to uPA") to provide preferred pharmaceutical compositions for use in the present invention.

The term "patient" or "subject" is used throughout the specification within context to describe an animal, generally a mammal and preferably a human, to whom treatment, including prophylactic treatment (prophylaxis, including especially as that term is used with respect to reducing the likelihood of metastasis of an existing cancer), with the compositions according to the present invention is provided. For treatment of those infections, conditions or disease states which are specific for a specific animal such as a human patient or a patient of a particular gender, such as a human male or female patient, the term patient refers to that specific animal. Compounds according to the present invention are useful for the treatment of cancer, including especially for use in reducing the likelihood of metastasis of a cancer.

The term "effective" is used herein, unless otherwise indicated, to describe an amount of a compound or composition which, in context, is used to produce or effect an intended result, whether that result relates to the inhibition of the effects of a disease state (e.g. cancer) on a subject or the treatment of a subject for secondary conditions, disease states or manifestations of disease states as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer or metastasis of cancer, including improvement in the condition through lessening or suppression of at least one symptom, inhibition of cancer growth, reduction in cancer cells or tissue, prevention, reduction in the likelihood or delay in progression of metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds as anti-angiogenic compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "antibody binding moiety", "antibody binding terminus" or "antibody binding structure" ($A_BM$) within the general formula of compounds according to the present invention) is used to described that portion of a bifunctional ARM-HI compound according to the present invention which comprises at least one small molecule or hapten which can bind to antibodies within the patient. The term "hapten" is used to describe a small-molecular-weight inorganic or organic molecule that alone is not antigenic but which when linked to another molecule, such as a carrier protein (albumin, etc.) or in the case of the present invention, as an antibody terminus in the present compounds, is antigenic; and an antibody raised against the hapten (generally, the hapten bonded or complexed to the carrier) will react with the hapten alone. Because, in many instances, anti-hapten (anti-DNP) antibodies are already present in the human blood stream as endogenous antibodies because they naturally become raised to endogenous haptens (already present in patients), no pre-vaccination is necessary for ARM-HI activity.

It is preferred that the antibody binding terminal comprise a hapten which is reactive with (binds to) an endogenous antibody that pre-exists in the patient prior to initiate therapy with the compounds of the present invention and does not have to be separately raised as part of a treatment regimen (for example, by vaccination or other approach for enhancing immunogenicity). Thus, haptens which comprise a di- or trinitro phenyl group or a fluorescein group as depicted below, or a digalactose hapten (Gal-Gal-Z, preferably Gal-Gal-sugar, preferably Gal-Gal-Glu), are preferred. Additionally, a compound according to the general structure:

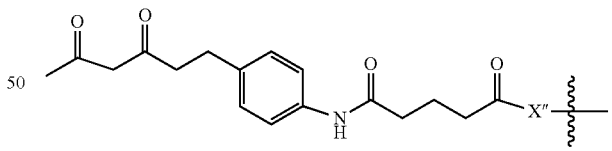

Where X" is O, $CH_2$, $NR^1$, S; and
$R^1$ is H, a $C_1$-$C_3$ alkyl group or a —C(O)($C_1$-$C_3$) group;
May be used as haptens in the present invention.
Further, a moiety according to the chemical structure:

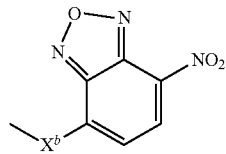

Where $X^b$ is a bond, O, $CH_2$, $NR^1$ (as above) or S may also be used as a hapten ($A_BM$) in the present invention. Other $A_BM$ moieties include the following structures:

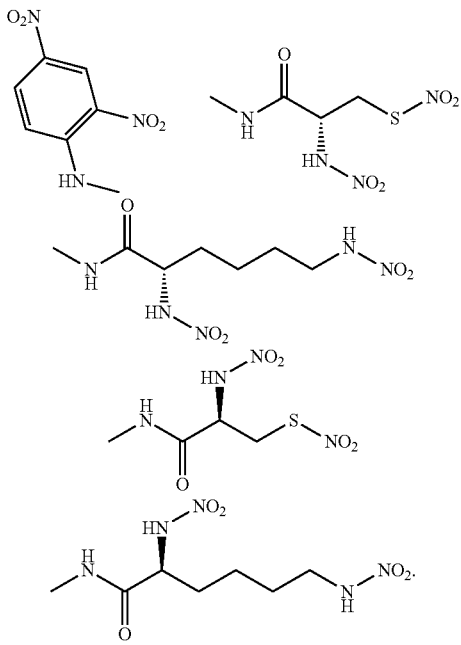

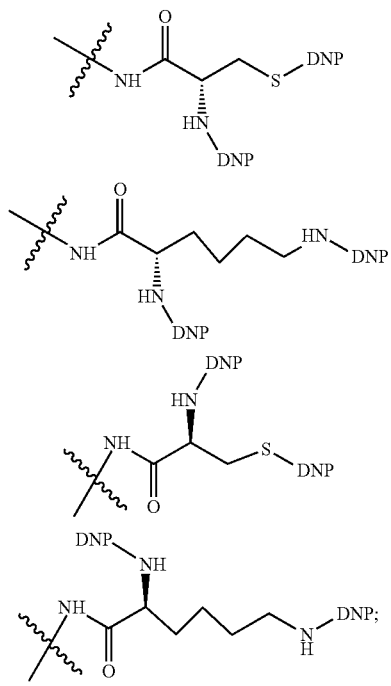

Each of the above amino acid $A_BM$ moieties may be further substituted with a dinitrophenyl group, optionally through an X group, e.g., through $CH_2$, S(O), $S(O)_2$, —$S(O)_2O$, —$OS(O)_2$, or $OS(O)_2O$ as otherwise described herein to provide the following $A_BM$ moieties:

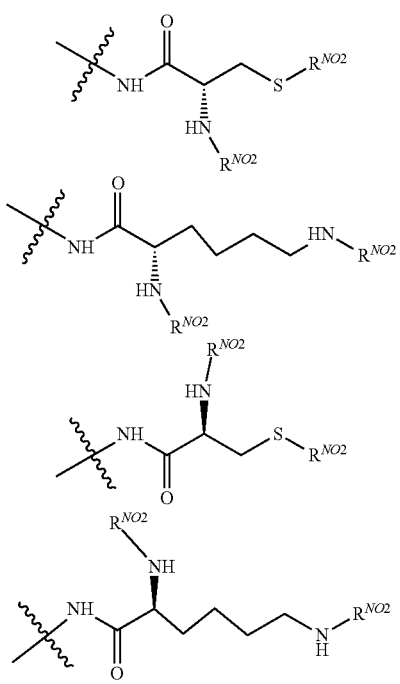

Where $R^{NO2}$ is a nitro group as above or a dinitrophenyl group as indicated below a group according to the chemical structure:

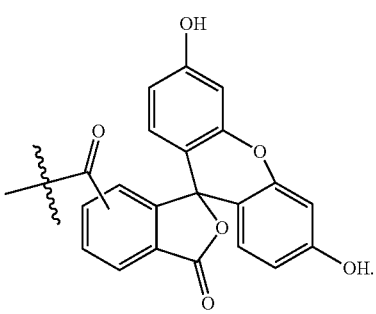

Where Y' is H or $NO_2$ (preferably H);

X is O, $CH_2$, $NR^1$, S(O), $S(O)_2$, —$S(O)_2O$, —$OS(O)_2$, or $OS(O)_2O$; and $R^1$ is H, a $C_1$-$C_3$ alkyl group, or a —$C(O)(C_1$-$C_3)$ group;

The fluorescein hapten ($A_BM$) moiety for use in the present invention is represented by the chemical structure (as a racemic mixture, or as either enantiomer) and is a preferred hapten for use in the present invention:

The (Gal-Gal-Z) hapten is represented by the chemical formula:

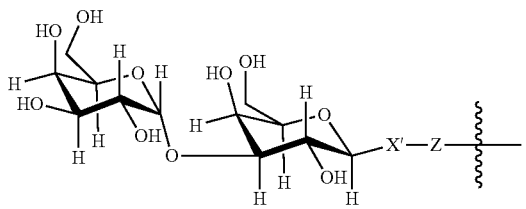

Where X' is $CH_2$, O, N—$R^{1'}$, or S, preferably O;
$R^{1'}$ is H or $C_1$-$C_3$ alkyl; and
Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferring, ceruloplasmin, major histocompatability complex proteins (MHC), enzymes, lectins and selectins, calnexin, calreticulin, and integrin glycoprotein IIb/IIa, among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or connector molecule) or a glucose or glucosamine (especially N-acetylglucosamine).

It is noted that Z is linked to a galactose residue through a hydroxyl group or an amine group on the galactose of Gal-Gal, preferably a hydroxyl group. A preferred hapten is Gal-Gal-Glu which is represented by the structure:

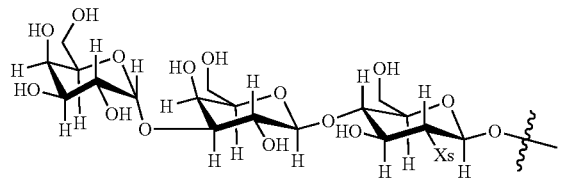

Where Xs is OH or NHAc.

Other $A_BM$ groups include, for example, the following groups:

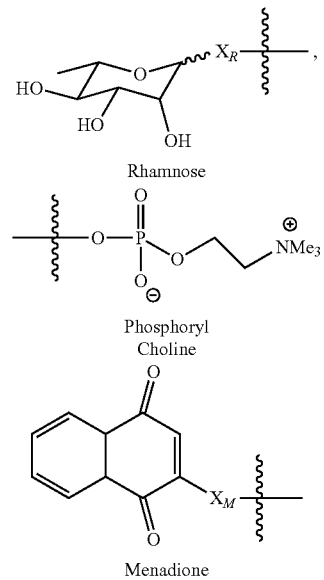

-continued

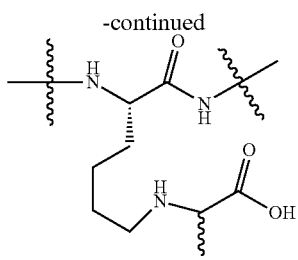

Carboxyethyl Lysine (CEL)

Where $X_R$ is O or S; and
$X_M$ is O or S.

It is noted in the carboxyethyl lysine $A_BM$ moiety either one, two or three of the nitrogen groups may be linked to the remaining portion of the molecule through the linker or one or both of the remaining nitrogen groups may be substituted with a dinitrophenyl through an X group as otherwise described herein.

The term "urokinase-type plasminogen activator", "uPA" or simply "urokinase" is used to describe a serine protease protein which has, as its physiological substrate, plasminogen, which becomes activated as plasmin. uPA is a 411-residue protein, consisting of three domains: the serine protease domain, the kringle domain, and the growth factor domain. uPA is synthesized as a zymogen form (prourokinase or single-chain urokinase), and is activated by proteolytic cleavage between L158 and I159. The two resulting chains are kept together by a disulfide bond. uPA which contains the two disulfide chains is referred to as high molecular weight uPA and is the preferred form for complexing with precursor compounds according to the present invention and creating ARM-U compounds (uPA complexed with precursor compounds) for use as pharmaceutical agents as otherwise described herein. It is noted that the uPA which may be used in the present invention is any uPA, including variants or mutants of uPA, preferably high molecular weight wild-type uPA, which can bind to precursor compounds according to the present invention and also bind to the urokinase-type plasminogen activator receptor (uPAR) and deliver antibody binding moieties to cancer cells through this binding. Mammalian uPA is often used, including primate uPA and human uPA, in particular human recombinant uPA. It is the high molecular weight uPA having two chains bound together by a disulfide bond, preferably human uPA, including human recombinant uPA, which is the preferred uPA used to complex precursor compounds according to the present invention. In the present invention, the higher molecular weight protein is used because this protein may be covalently or non-covalently bound to precursor compounds according to the present invention to produce a ARM-U or "urokinase complex", and these ARM-U compounds are the preferred compounds for administration to patients or subjects in the treatment of cancer, especially including metastatic cancer as described herein.

The term "urokinase binding moeity" or $U_KBM$ is use to described that portion of a chimeric compound according to the present invention which comprises at least one small molecule or moiety which can bind covalently or non-covalently to urokinase-type plasminogen activator or (uPA) to produce ARM-U compounds hereof. That binding may be non-covalent or covalent, but is preferably covalent in-order to maintain the compound in the active site of uPA in order to attract antibodies to cancer cells. Once bound, the $U_KBM$ group is often referred to as a $U_KBM_B$ group and the compounds are referred to as ARM-U compounds.

Preferred $U_KBM$ groups for use in the present invention are set forth below. In one embodiment the $U_KBM$ group (note that the $U_KBM$ group is set forth below represenatationally in complete chimeric compounds according to the present invention as

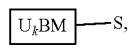

where there can be more than one

group in the final compound)

is a group according to the chemical structure (depicted with S attached):

Where T is group which binds to uPA, preferably covalently, and is preferably a $R^e$ group or an amino acid group according to the chemical structure:

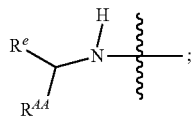

$R^{AA}$ is a sidechain of an amino acid, preferably a side chain of lysine or arginine

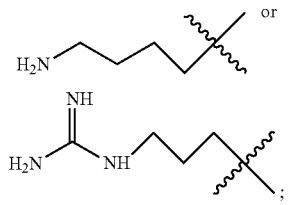

$R^e$ is H (resulting in non-covalent binding to uPA) or an electrophilic group which reactive with a nucleophile in the active site of uPA to produce a covalent bond (preferably on a histidine residue within the active site of uPA), preferably an electrophilic group according to the chemical formula:

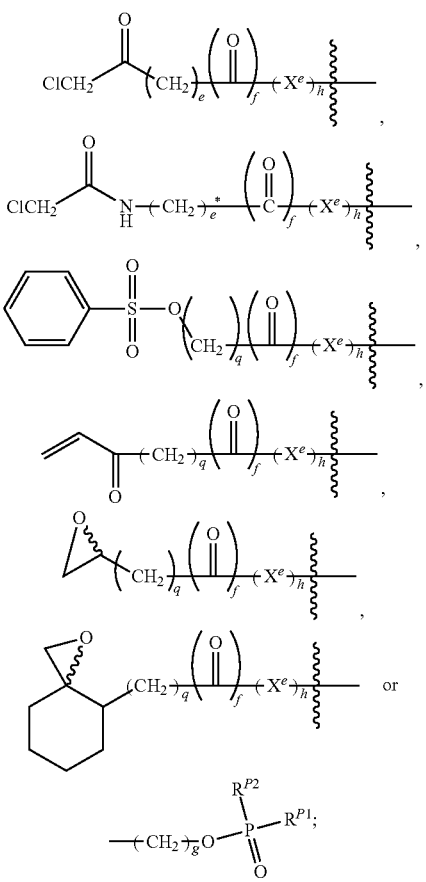

Where $X^e$ is O, S, or N—$R^{Xe}$;

$R^{Xe}$ is H or a $C_1$-$C_3$ alkyl or alkanol group;

$R^{P1}$ is any group which forms a stable linkage with the phosphate moiety, and is an optionally substituted hydrocarbyl group, often an optionally substituted $C_1$-$C_{12}$ alkyl group (preferably methyl), an optionally substituted aromatic or heterocyclic group (preferably, an optionally substituted phenyl group or a heteroaryl group which is a 5-6 membered ring);

$R^{P2}$ is a halogen (preferably F or Cl, most often F because of its reduced reactivity in water)

Each e is independently 0, 1, 2, 3, 4, 5 or 6;

Each f is independently 0 or 1 (often 0); and

Each g is 0, 1, 2, 3, 4, 5 or 6 (often 1);

Each h is independently 0 or 1;

Each q is independently 1, 2, 3, 4, 5, or 6

Each (AA) is independently a single amino acid residue or if $p_1$ is more than 1, forms a polypeptide (i.e., an amino acid containing residue comprising at least two amino acids linked together through peptide bond(s)), the amino acid is often glycine, alanine, serine, threonine, leucine, isoleucine, aspartic acid or glutamic acid, is most often alanine or glycine, but may be any amino acid as otherwise described here);

$p_1$ is an integer from 0 to 25 (including all integers within that range), often 0 to 10 (preferably 1-6, 1, 2, 3, 4, 5, or 6) and S is

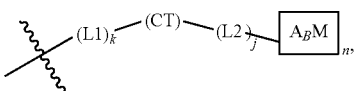

Where L1, CT, L2,

k, j and n are as otherwise described herein, or a pharmaceutically acceptable salt, enantiomer, solvate or polymorph thereof.

In alternative embodiments,

is a group according to the chemical structure:

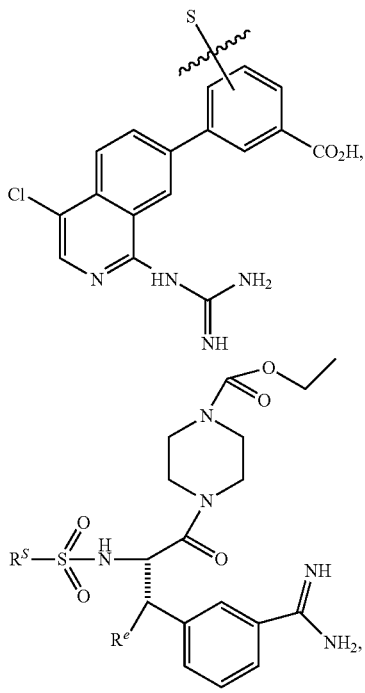

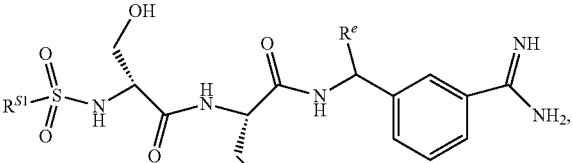

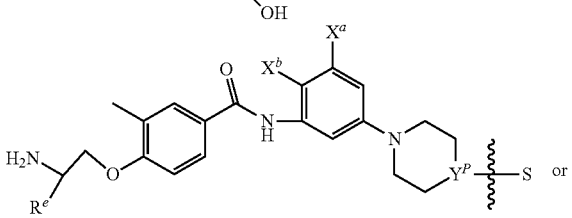 or

-continued

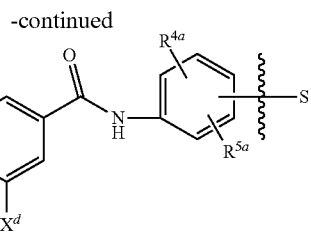

Where $R^e$ is the same as above (i.e., H or an electrophilic group as described, preferably, a chloromethylketone group);
$R^S$ is S or a group

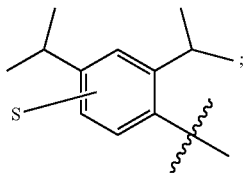

$R^{S1}$ is S or a group;

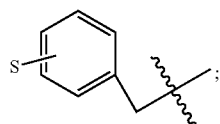

$Y^P$ is N or $CH_2$;
$X^a$ is H, a halogen (preferably F or Cl), a $C_1$-$C_3$ alkyl group (preferably methyl) or a —O—($C_1$-$C_3$ alkyl group), preferably $X^a$ is F, Cl or $CH_3$ (more often F or Cl);
$X^b$ is H, a halogen (preferably F or Cl), a $C_1$-$C_3$ alkyl group or a —O—($C_1$-$C_3$ alkyl group), preferably $X^b$ is H or O-Et;
$X^c$ and $X^d$ are each independently H, a halogen (preferably F or Cl), a $C_1$-$C_3$ alkyl group (often $CH_3$) or a —O—($C_1$-$C_3$ alkyl group), preferably Cl or $CH_3$, more preferably Cl and $CH_3$;
$R^{4a}$ and $R^{5a}$ are each independently H, a halogen (preferably F or Cl), a $C_1$-$C_3$ alkyl group (often $CH_3$) or a —O—($C_1$-$C_3$ alkyl group), preferably H, OMe, OEt or OiPr; and
S (as a group) is the same as above, or
a pharmaceutically acceptable salt thereof.

The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The term "amino acid" or, in certain instances "AA", is used to describe one or more amino acid residues (D- or L-amino acids) within a polypeptide (more than one amino acid linked together though peptide bonds) which may be natural or unnatural. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "sidechain of an amino acid" is used to describe a group on the chiral carbon to which the amine and carboxylic acid groups are also attached which is identifiable for a given amino acid. Thus, for glycine, its sidechain is "H", for alanine, its sidechain is "$CH_3$", each amino acid has a unique side chain which reflects its underlying chemical characteristics which is distinguishable from other amino acids. The sidechain of an amino acid which is on the chiral (except for glycine) carbon to which the amine and carboxylic acid groups are generally bound, may be disposed (provide a configuration) which is racemic or enantiomeric, with either the D- or L-configuration representing the configurational orientation of the sidechain. Typical amino acid sidechains include, for example, alanine (methyl), arginine (propyleneguanidine), asparagine (methylenecarboxyamide), aspartic acid (ethanoic acid), cysteine (thiol, reduced or oxidized di-thiol), glutamine (ethylcarboxyarnide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline (forms a cyclic ring with the adjacent nitrogen group to form a pyrrolidine group), serine (methanol), threonine (ethanol, 1-hydroxyethane), tryptophan (methyleneindole), tyrosine (methylene phenol) or valine (isopropyl).

The term "linker", "L1" or "L2" refers to a chemical entity connecting an antibody binding ($A_BM$) moiety to a urokinase-like plasminogen activator binding moiety (UkBM), optionally through a connector moiety (CT) through covalent bonds. The linker between the two active portions of the molecule, that is the antibody binding moiety ($A_BM$) and the urokinase binding moiety ($U_kBM$) ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 2 and 15 glycol units, 1 and 8 glycol units, 2 and 6 glycol units in length may be preferred. By having a linker with a length as otherwise disclosed herein, the $A_BM$ moiety and the $U_kBM$ moiety may be situated to advantageously take advantage of the biological activity of compounds according to the present invention which bind to urokinase-like plasminogen activator on cancer cells, including cancer cells prone to metastasis and attract endogenous antibodies to those cells to which the compounds are bound, resulting in the selective and targeted death of those cells. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages is preferred. Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

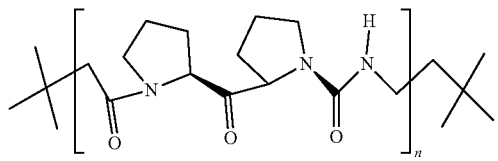

n polyproline linker
or

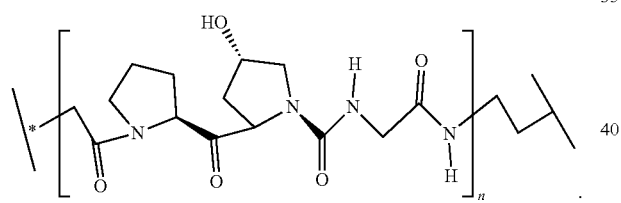

collagen linker.

Preferred linkers include those according to the chemical structures:

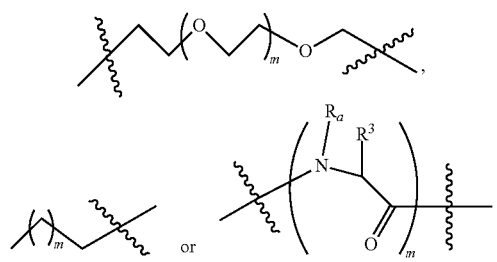

Or a polypropylene glycol or polypropylene-co-polyethylene glycol linker having between 1 and 100 alkylene glycol units;

Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m (within the context of this use) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n (within the context of this use) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.) or Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units, to which is bonded a lysine group (preferably at its carboxylic acid moiety) which binds one or two DNP groups to the lysine at the amino group(s) of lysine. Still other linkers comprise amino acid residues (D or L) to which are bonded to $A_BM$ moieties, in particular, DNP, among others at various places on amino acid residue as otherwise described herein. In another embodiment, as otherwise described herein, the amino acid has anywhere from 1-15 methylene groups separating the amino group from the acid group in providing a linker to the $A_BM$ moiety.

Or another linker is according to the chemical formula:

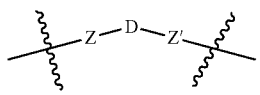

Where Z and Z' are each independently a bond, —$(CH_2)_i$—O, —$(CH_2)_i$—S, —$(CH_2)_i$—N—R,

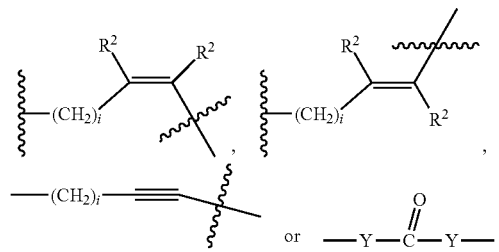

wherein said —$(CH_2)_i$ group, if present in Z or Z', is bonded to a connector (CT), $A_BM$ and/or $U_kBM$;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 0 to 100, 0 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;

D is

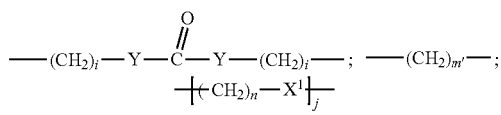

or
a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 (n is preferably 2);

$X^1$ is O, S or N—R; and

R is as described above, or a pharmaceutical salt thereof.

The term "connector", symbolized in the generic formulas by (CT), is used to describe a chemical moiety which is optionally included in bifunctional compounds according to the present invention which forms from the reaction product of an activated $A_B$M-linker with a $U_k$BM moiety (which also is preferably activated) or an $A_B$M moiety with an activated linker-$U_k$BM as otherwise described herein. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group, although in certain instances, incorporated into the linker group, as otherwise described herein. It is noted also that a connector group may be linked to a number of linkers to provide multifunctionality (i.e., more than one $U_k$BM moiety and/or more than one $A_B$M moiety within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups as otherwise described herein. It is further noted that a connector (or linker) may be connected to $A_B$M, a linker or $U_k$BM at positions which are represented as being linked to another group using the symbol

Where two or more such groups are present in a linker or connector, any of an $A_B$M, a linker or a $U_k$BM may be bonded to such a group. Where that symbol is not used, the linker may be at one or more positions of a moiety.

Common connector groups which are used in the present invention include the following chemical groups:

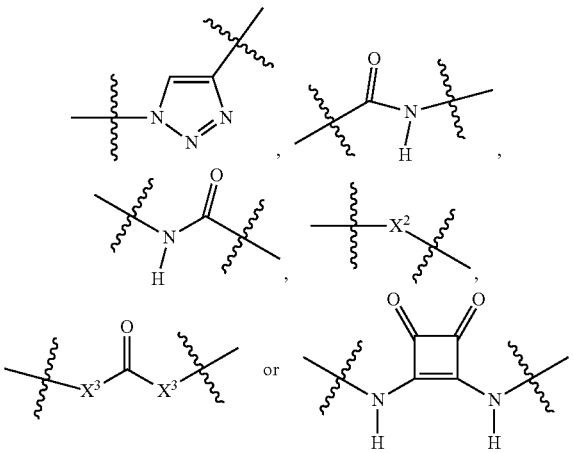

Where $X^2$ is O, S, $NR^4$, S(O), $S(O)_2$, —$S(O)_2$O, —OS$(O)_2$, or OS$(O)_2$O;

$X^3$ is O, S, $NR^4$; and $R^4$ is H, a $C_1$-$C_3$ alkyl or alkanol group, or a —C(O)($C_1$-$C_3$) group. The triazole group, indicated above, is a preferred connector group.

As discussed hereinabove, it is noted that each of the above groups may be further linked to a chemical moiety which bonds two or more of the above connector groups into a multifunctional connector, thus providing complex multifunctional compounds comprising more than one $A_B$M and/or $U_k$BM group within the multifunctional compound.

The term "hydrocarbon" or "hydrocarbyl" refers to any monovalent radical containing carbon and hydrogen, which may be straight, branch-chained or cyclic in nature and preferably contains from 1 to 30 carbon atoms, but may be larger. Hydrocarbons include linear, branched and cyclic hydrocarbons, including alkyl groups, alkylene groups, saturated and unsaturated hydrocarbon groups (e.g., alkene, alkyne), including aromatic groups both substituted and unsubstituted.

The term "alkyl" refers to a fully saturated monovalent radical containing carbon and hydrogen, and which may be cyclic, branched or a straight chain containing from 1 to 30 carbon atoms, from 1 to 20 carbon atoms, often 1 to 12 or 1 to 10 carbon atoms (1, 2, 3, 4, 5, 6, 7, 8, 9 or 10). Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ or $C_1$-$C_3$ alkyl groups. "Alkylene" when used, refers to a fully saturated hydrocarbon which is divalent (may be linear, branched or cyclic) and which is optionally substituted. Other terms used to indicate substitutent groups in compounds according to the present invention are as conventionally used in the art.

"Aryl" or "aromatic", in context, refers to a substituted or unsubstituted monovalent aromatic radical having a single ring (e.g., benzene) or multiple condensed rings (e.g., naphthyl, anthracenyl, phenanthryl, phenacenyl) and can be can be bound to the compound according to the present invention as indicated. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, pyridyl, furanyl, thiene, thiazole, pyridine, pyrimidine, pyrazine, triazole, oxazole, indole or preferably fused ring systems (bicyclic, tricyclic), among others, which may be substituted or unsubstituted as otherwise described herein. Preferred heteroaryl groups are hydrophobic in nature or can be rendered hydrophobic by including one or more hydrophobic substituents on the heteroaryl group, or creating a fused system where at least one of the rings is a benzene (phenyl) ring.

The term "cyclic" shall refer to an optionally substituted carbocyclic or heterocyclic group, preferably a 5- or 6-membered ring or fused rings (two, three or four rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred cyclic groups are hydrocarbyl groups, preferably unsaturated hydrocarbyl groups which are optionally substituted. Other cyclic groups are bicyclo alkyl groups, each of which may be optionally substituted. Preferred heterocyclic groups are heteroaryl or heteroaromatic.

The term "heterocyclic group" as used throughout the present specification refers to an aromatic ("heteroaryl") or non-aromatic cyclic group forming the cyclic ring(s) and including at least one hetero atom such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline, carbostyryl, piperazinyl, N-methylpiperazinyl, tetrahydropyranyl, 1,4-dioxane and phthalimide, among others.

Exemplary heteroaryl moieties which may be used in the present invent ion include for example, pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and especially aromatic heterocycles comprising 2 or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. Further heteroaryl groups may include pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine, furopyrimidine and thienopyrimidine, preferably benzothiophene, benzothiazole, quinoline, quinazoline, cinnoline, pyrrolopyrimidine, furopyridine and thienopyrimidine.

The term "substituted" shall mean substituted at a carbon (or nitrogen) position within context, hydroxyl, carboxyl, cyano (C≡N), nitro ($NO_2$), halogen (1, 2 or 3 halogens, especially on an alkyl, especially a methyl group such as a trifluoromethyl), thiol, alkyl group (often $C_1$-$C_{10}$, more often, $C_1$-$C_6$ or even $C_1$-$C_3$ alkyl), alkoxy group (preferably, $C_1$-$C_{10}$ alkyl or aryl, including phenyl and substituted phenyl), ester (preferably, $C_1$-$C_{10}$ alkyl or aryl) including alkylene ester (such that attachment is on the alkylene group, rather than at the ester function which is preferably substituted with a $C_1$-$C_{10}$ alkyl or aryl group), thioether (preferably, $C_1$-$C_{10}$ alkyl or aryl), thioester (preferably, $C_1$-$C_{10}$ alkyl or aryl), (preferably, $C_1$-$C_{10}$ alkyl or aryl), halogen (F, Cl, Br, I), nitro or amine (including a five- or six-membered cyclic alkylene amine, further including a $C_1$-$C_{10}$ alkyl amine or $C_1$-$C_{10}$ dialkyl amine), amido, which is preferably substituted with one or two $C_1$-$C_{10}$ alkyl groups (including a carboxamide which is substituted with one or two $C_1$-$C_{10}$ alkyl groups), alkanol (preferably, $C_1$-$C_{10}$ alkyl or aryl), or alkanoic acid (preferably, $C_1$-$C_{10}$ alkyl or aryl). Preferably, the term "substituted" shall mean within its context of use alkyl, alkoxy, halogen, ester, keto, nitro, cyano and amine (especially including mono- or di-$C_1$-$C_{10}$ alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms. Preferred substituents are those which have hydrophobic characteristics as otherwise described herein. It is noted that the incorporation of a hydrophobic substituent onto an otherwise less hydrophobic or non-hydrophobic moiety may render the enter moiety hydrophobic as described for the present invention.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially including metastatic cancer. Exemplary anticancer agents which may be coadministered in combination with one or more chimeric compounds according to the present invention include, for example, antimetabolites, inhibitors of topoisomerase I and/or II, alkylating agents and microtubule inhibitors (e.g., taxol), among numerous others, as otherwise described herein.

The term "additional anti-cancer agent" refers to one or more traditional cancer agent(s) which may be co-administered with compounds according to the present invention in the treatment of cancer. These agents include chemotherapeutic agents include one or more members selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3-inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumurnab, arnrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, arninoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxyrnesterone, lutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa tretinoin, vindesine. 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

Chemical Synthesis

Figure 6:
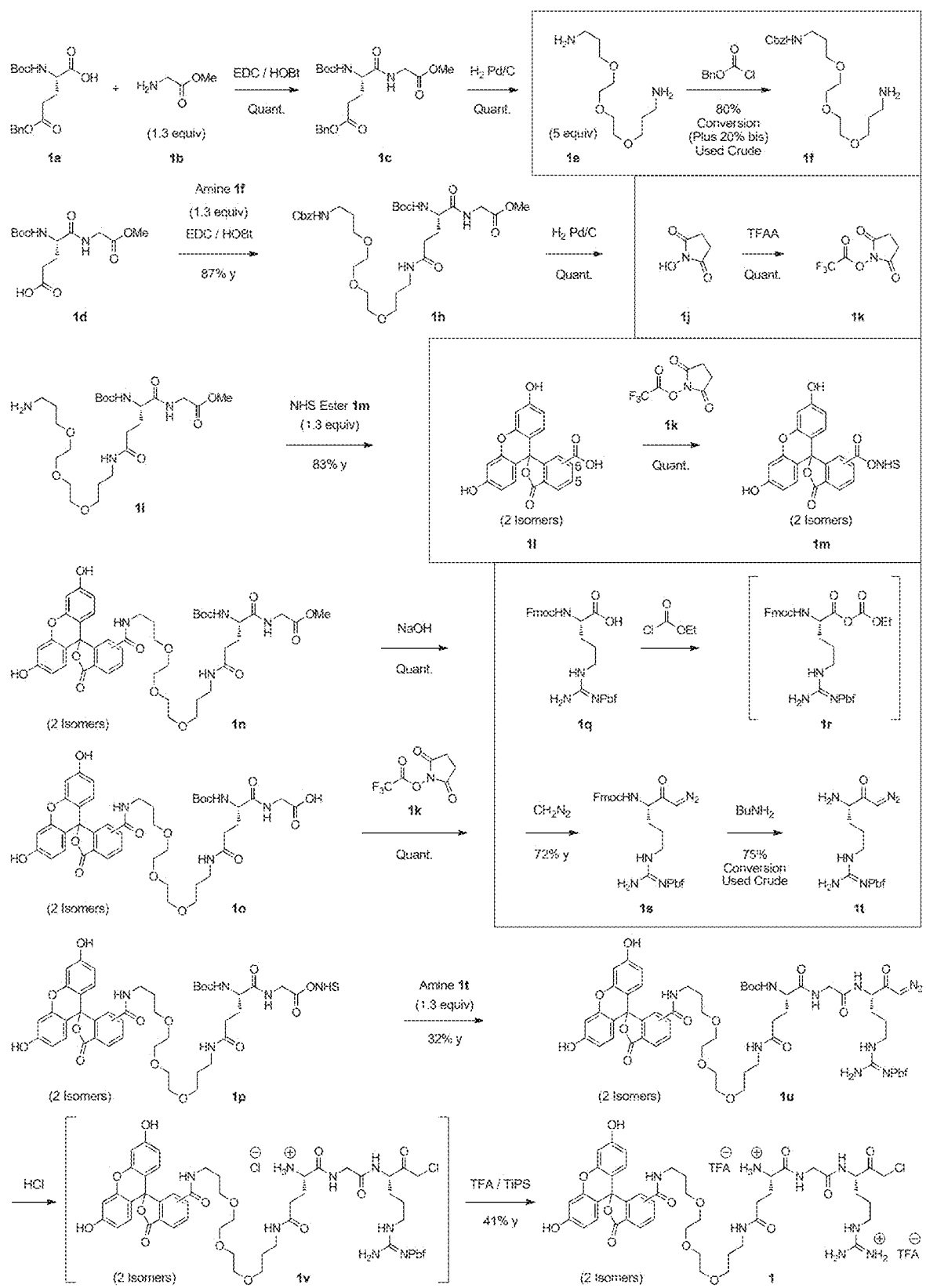
FIG. 6 shows a chemical scheme (Scheme I) for the synthesis of compound 1. The experimental details of this synthesis are provided in the examples section of the present application.
Figure 7:
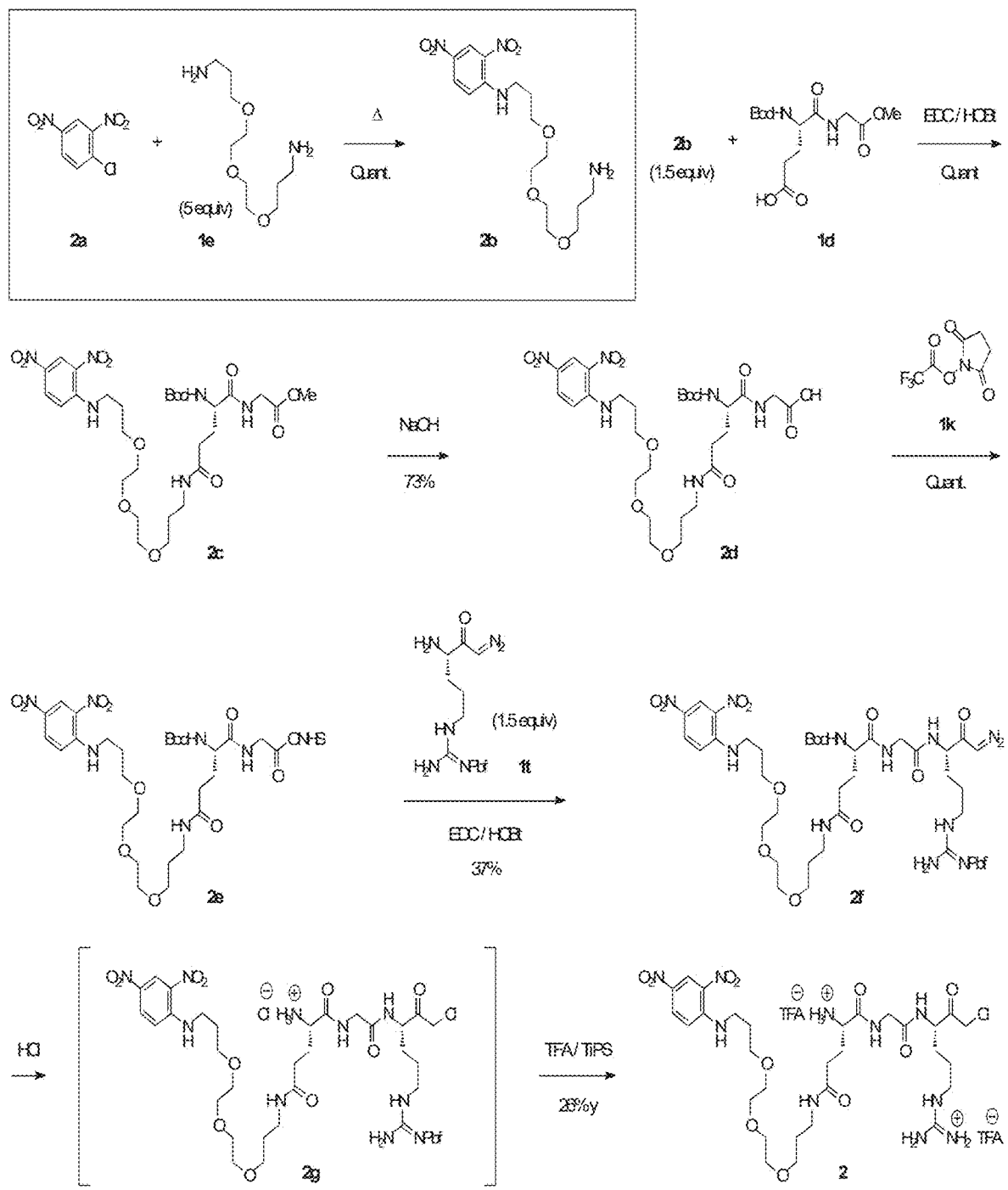
FIG. 7 shows a chemical scheme (Scheme II) for the synthesis of compound 2. The experimental details of this synthesis are provided in the examples section of the present application.

The present compounds are readily synthesized by standard methods which are well known in the art. The chemical synthesis of three exemplary compounds are presented in attached FIGS. 6-8, details of which are set forth in the examples section of the present application. Compound 1 is synthesized pursuant to the multi-step chemical scheme which is presented in FIG. 6 hereof. In short, the carboxylic acid function of a fluorescein compound 11 is reacted with the free amine group of an intermediate compound 1i, which is prepared in a series of steps starting with protected glutamic acid derivative 1a which is condensed onto a free amino group of carboxyl-protected glycine 1b to produce intermediate 1c which is then prepared for further condensation by removing the protecting group from the carboxylic acid of the glutamic acid sidechain (to provide 1d) and condensing the now free carboxylic acid onto the free amine of protected diamino compound 1f to provide intermediate 1h. 1h is prepared for further condensation by removing the blocking group from the primary amine position to provide 1i. Reaction of intermediate 1i with 1m (an activated species of fluorescein) produces condensed compound 1n which is deprotected to provide the free carboxylic acid compound to. Compound 1o is activated 1p and reacted with amine intermediate compound 1t (which is a arginine derivativate as indicated in FIG. 6) to produce compound. Compound 1t is condensed with compound 1p to produce compound 1u which is acidified to produce compound 1v, which is deprotected to provide the di-trifluoroacetate salt compound 1.

Compound 2 is synthesized in a slightly different manner than compound 1, starting from chlorodinitrobenzene 2a (FIG. 7), which is condensed with the diamine 1e to produce DNP-linked intermediate 2b. Intermediate 2b is then condensed with the protected diaminoacid (Ala-Glu) to afford the amine protected intermediate 2c, which is deprotected to afford intermediate 2d. Intermediate 2d is activated (carboxylic acid group) and condensed with the arginine derivative 1t (which was used in the synthesize of compound 1, above) to afford amine-protected intermediate 2f. Removal of the.

amine-protecting group with acid affords intermediate 2g which is deprotected to provide the di-trifluoroacetate salt compound 2.

Compound 3, also synthesized is related to compound 1, except the chloromethyl ketone group is an unreactive methyl ketone group. Arginine derivative 3f is synthesized in a series of steps from protected arginine starting material 3a. Compound 3f is condensed with compound 1p (Scheme I, FIG. 6) to produce the protected compound 3g, which is deprotected to provide final compound 3. Final compound 3 is a non-irreversible bound compound which also may function as an anticancer agent pursuant to the present invention, although in a manner which is not as effective as for compounds 1 and 2.

Alternative methods for synthesizing compounds may be modified from the synthetic steps which are presented herein or are otherwise well known in the art. Most of the chemistry associated with obtaining the present compounds relates to condensation reactions to introduce linkers onto $U_k$MB groups and/or $A_B$M groups. The $U_k$MB groups and/or $A_B$M groups may be readily obtained and derivatized to provide a nucleophilic group (oxygen, nitrogen, sulfur, deprotonated carbon) for condensing with an electrophilic group such as a carboxylic acid group, an epoxide, or a haloalkyl group, etc). Additionally, chemical synthetic steps may be utilized and/or modified from published patent applications, including WO 2009/139863, published Nov. 19, 2009, WO 2011/046946, published Apr. 21, 2011 and WO 2012/068366, published May 24, 2012, relevant portions of which are incorporated by reference herein.

While specific analogs have been shown and described, the present invention is not limited to these specific analogs and other antibody recruiting compounds that can function as the antibody binding moiety connected by a linker to a $U_k$BM urokinase-type plasminogenic activator on cancer cell surfaces, would fall within the scope of the present invention. All of these compounds can be formulated into pharmaceutical compositions as otherwise described herein and used in the methods which are presented.

Pharmaceutical compositions comprising combinations of an effective amount of at least one bifunctional compound according to the present invention, and optionally, one or more of the compounds otherwise described herein, all in effective amounts, in combination with a pharmaceutically effective amount of a carrier, additive or excipient, represents a further aspect of the present invention. In a particularly preferred pharmaceutical composition according to the present invention, one or more precursor compounds which comprise an AbM moiety and linker group as described herein are allowed to "react" or bind to urokinase (the higher molecular weight form of uPA comprising two polypeptide chains linked by a disulfide bridge) to form a urokinase-type plaminogen activity uPA-precursor complex (the precursor compound is preferably covalently bound to uPA, as discussed hereinabove). This uPA-precursor complex is formulated as a pharmaceutical composition as otherwise described herein and administered to a patient or subject in the treatment of cancer, including metastatic cancer as otherwise described herein. In preferred aspects of the present invention which relates to uPA-precursor complex, the complex is formed by reacting or exposing uPA in buffer solution to a precursor compound as otherwise described herein to produce the uPA-precursor complex, which may be used directly or further formulated with at least one additional pharmaceutically acceptable carrier, additive or excipient.

Although a number of methods may be used to produce ARM-U (i.e., uPA-precursor complex compounds) according to the present invention generally by reacting a precursor compound as otherwise described herein with urokinase in an aqueous solvent such as buffer and/or a buffer/saline solution and optionally a small amount of another solvent at a temperature (generally, at a temperature so as not to denature or otherwise deactive the uPA protein or have the precursor rendered inactive by reacting with water) and for a time sufficient to form the ARM-U compound, a preferred method is that which provides ARM-U pursuant to the following methodology. In this preferred approach the uPA is dissolved in water and/or a buffer (e.g. HEPES/saline or other buffer system) and subsequently the precursor compound is added to the uPA and allowed to react. After a sufficient period of time (which can range from a few minutes to several hours or more), the ARM-U compound which forms can be used directly or formulated into a number of pharmaceutical compositions. Various concentrations of the final ARM-U compound may be formed and formulated accordingly.

Once formed, the ARM-U compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the topical cream or lotion may be used prophylatically to prevent infection when applied topically in areas prone toward virus infection. In additional aspects, the compounds according to the present invention may be coated onto the inner surface of a condom and utilized to reduce the likelihood of infection during sexual activity.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other bifunctional compound according to the present invention or other anti-cancer agent which may be used to treat cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of the ARM-U compound according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating cancer and/or secondary effects of cancer or ameliorate the secondary effects and conditions associated with cancer, including metastasis of cancer. This treatment can also be administered in conjunction with other conventional cancer therapies.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agent, anti-HIV agents, antibiotics, antifungals, anti-inflammatories, or antiviral compounds. In certain preferred aspects of the invention, one or more ARM-U compounds according to the present invention are coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

ARM-U Design, Synthesis, and Evaluation

Figure 2:
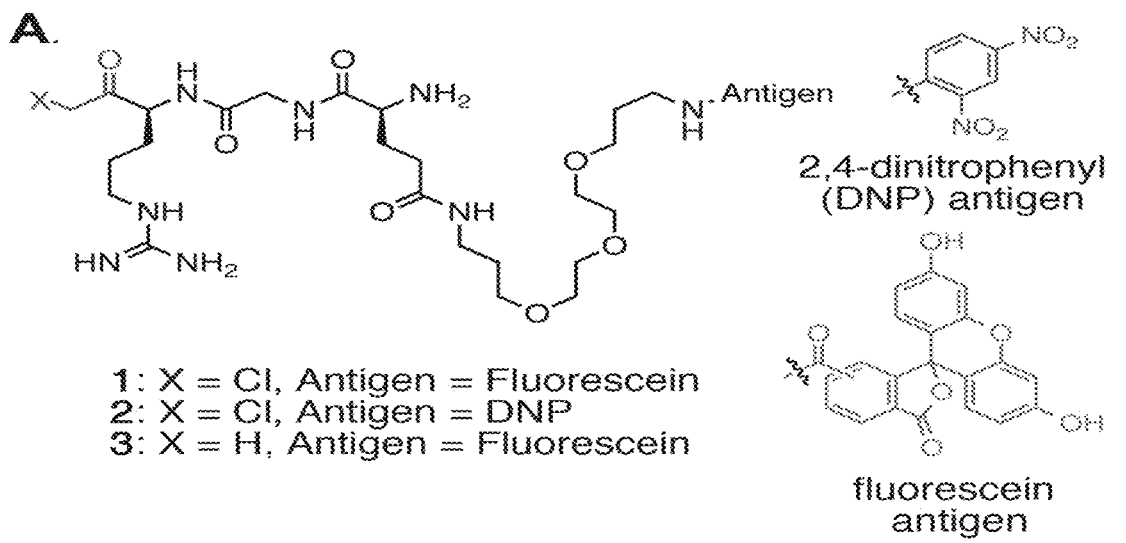
FIG. 2 (A) shows chemical structures of bifunctional small molecules described herein. (B) shows the X-ray crystal structure of covalent adduct 5, which is formed from the interaction of uPA and chloromethyl ketone 4 (PDB ID: 1LMW).[xxxv] The inhibitor is shown in stick representation with grey Cα atoms, and the protein is depicted as a turquoise surface.
Figure 2:
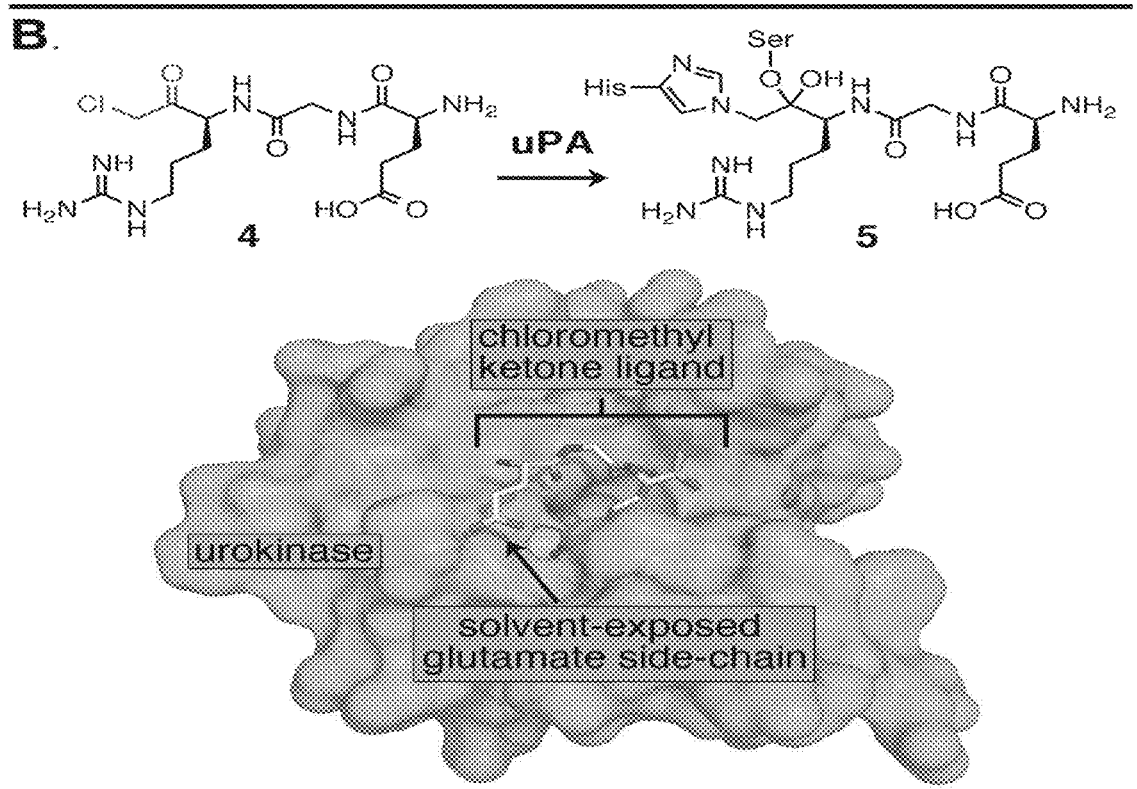

With the goal of preparing ARM-U by simultaneously inactivating uPA's catalytic activity and site-specifically attaching an antibody-recruiting hapten to the protein, we designed chloromethyl ketones 1 and 2 (FIG. 2A). These molecules were inspired by tripeptide 4, which has been shown to covalently inhibit several serine proteases including uPA.[xxxiv,xxxv,xxxvi] Analysis of a published crystal structure of uPA bound to chloromethyl ketone inhibitor 4 (FIG. 2B)[xxxv] suggested to us that the glutamic acid side chain of the inhibitor would remain solvent-exposed following covalent binding and would therefore serve as an ideal site to attach an antibody-recruiting motif. Thus, we prepared chloromethyl ketones 1 and 2, which incorporate ethylene glycol-derived linkers to connect either fluorescein or DNP to the chloromethyl ketone tripeptide. Methyl ketone 3 cannot covalently bind uPA because it lacks the electrophilic chloromethyl group found in 1 and 2, with 3 therefore serving as a negative control (although it is a non-covalent inhibitor of uPA).

Figure 3:
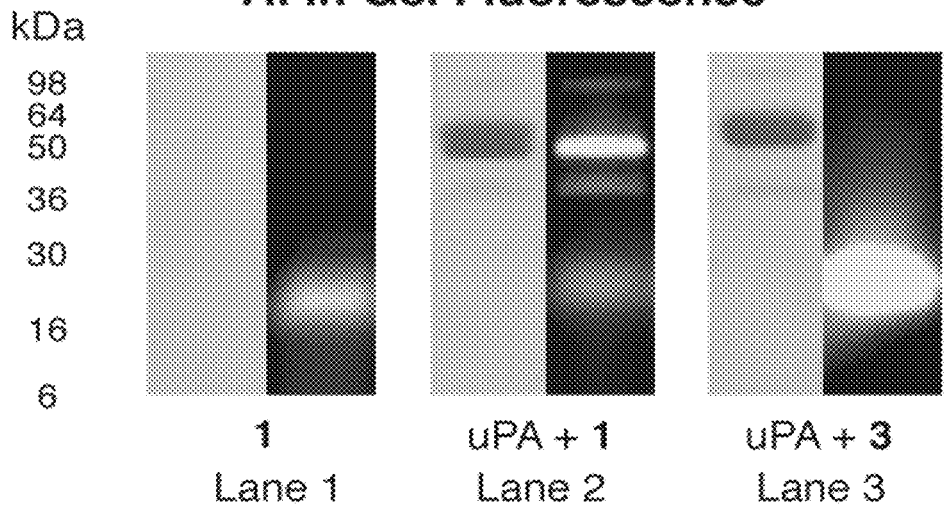
FIG. 3 (A) shows in-gel fluorescence (488 nm excitation, 532 nm emission, right) and Coomassie stain (left) analyses of mixtures of compound 1 (15 µM), uPA (10 µM), and compound 3 (60 µM). (B) Flow cytometry measurements of ARM-U$_{Fluor}$ binding to HT-29 cells compared to L-uPA$_{Fluor}$ as a negative control. Data points represent average values from triplicate experiments ±standard deviation.
Figure 3:
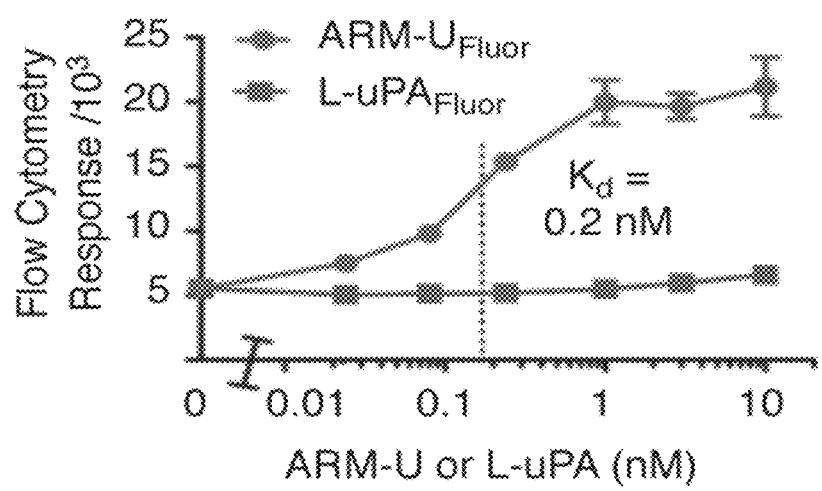

The inventors initially evaluated the reaction between uPA and compound 1 (to form ARM-U$_{Fluor}$) by measuring uPA-mediated hydrolysis of a known fluorogenic substrate (Cbz-Gly-Gly-Arg-7-amino-4-methylcoumarin).[xxxvii] This analysis (Supplementary Figure S1) reveals a 97% reduction in uPA activity versus buffer-treated uPA, which suggests that compound 1 virtually quantitatively functionalizes uPA's active site during the 1-hour, ambient-temperature incubation. We further evaluated ARM-U$_{Fluor}$ by SDS-PAGE with in-gel fluorescence detection[xxxvi] (FIG. 3A and Supplementary Figure S2). Incubating uPA with 1.5 equivalents of compound 1 (lane 2) substantially increases the fluorescence intensity of the protein's band at 54 kDa. Incubating uPA with higher concentrations of 1 (up to 12 equivalents) does not substantially further increase the amount of fluorescence observed in this band (Supplementary Figure S3), which suggests that 1 attaches only to a single site on uPA. Furthermore, treating uPA with compound 3, which cannot covalently bind the protein (6 equiv, lane 3), does not lead to observable fluorescence changes in uPA's band, which implies that a covalent bonding event is necessary for complex formation with uPA. Taken together, these data suggest that compound 1 forms a 1:1 covalent complex with uPA at the enzyme's active site and provides ARM-U$_{Fluor}$ as a chemically defined, homogeneous reagent. The antibody-recruiting complex ARM-U$_{DNP}$ was prepared analogously to ARM-U$_{Flour}$ by simply replacing chloromethyl ketone 1 with compound 2.

To demonstrate that ARM-U$_{Fluor}$ can bind anti-fluorescein antibodies, we employed an ELISA protocol.[xxxviii] ELISA wells were coated with anti-uPA antibody, treated with ARM-U$_{Fluor}$ (or uPA as a negative control), treated with anti-fluorescein antibody, and analyzed with alkaline-phosphatase-conjugated secondary antibody. Data from these experiments (Supplementary Figure S6) indicate that anti-fluorescein antibody exhibits concentration-depending binding to ARM-U$_{Fluor}$ with a K$_d$ of approximately 200 µM. These results indicate that both ends of bifunctional small molecule 1 can interact simultaneously with their respective protein targets (uPA and antibody).

The inventors next evaluated ARM-U$_{Fluor}$-mediated ternary complex formation on the surface of HT-29 human colonic adenocarcinoma cells, which have been reported to express approximately 1.4×10$^5$ molecules of uPAR per cell.[xxxix] Incubation of HT-29 cells with ARM-U$_{Fluor}$, followed by anti-fluorescein antibody and fluorescently labeled secondary antibody, gives rise to a concentration-dependent, saturable binding interaction (FIG. 3B). These data indicate a K$_d$ for the ARM-U$_{Fluor}$-uPAR interaction of approximately 200 µM, which is consistent with previously reported values for the uPA-uPAR interaction.[iv] A bifunctional construct (L-uPA$_{Fluor}$) formed from 1 and low-molecular-weight uPA, which lacks the uPAR-binding domain,[iv] shows negligible cell-binding ability under identical experimental conditions. Furthermore, pre-treatment of HT-29 cells with an anti-uPAR antibody that blocks the uPA binding site completely negates the cellular binding of ARM-U$_{Fluor}$ (Supplementary Figure S9). These data support that ARM-U$_{Fluor}$ specifically targets cells via interactions with uPAR. Furthermore, these observations are consistent with our hypothesis that modifying uPA's active site should not perturb its receptor-binding ability because uPA's receptor-binding and catalytic domains reside on opposite ends of the protein.

ARM-U Mediated Cell Killing

The inventors next evaluated the ability of ARM-U-templated ternary complexes to induce immune-mediated responses against uPAR-expressing target cells. We first studied antibody-dependent cellular phagocytosis (ADCP) using a two-color flow cytometry protocol.[xl] Here we measured ARM-U-dependent phagocytosis of both HT-29 cells and A172 human glioblastoma cells (which have been reported to express approximately 1.0×10$^6$ molecules of uPAR per cell)[xxxix] by IFN-γ-activated U937 effector cells.[xli] In this ADCP assay, target and effector cells are labeled with different fluorescent cell-membrane dyes and then incubated together with ARM-U$_{DNP}$ and anti-DNP antibodies. Cell mixtures are then analyzed by two-color flow cytometry, and phagocytosed cells are identified as those showing fluorescence from both target and effector cells. As previously described, these double-positive cells represent phagocytic events rather than cell-cell aggregates.[xl]

Figure 4:
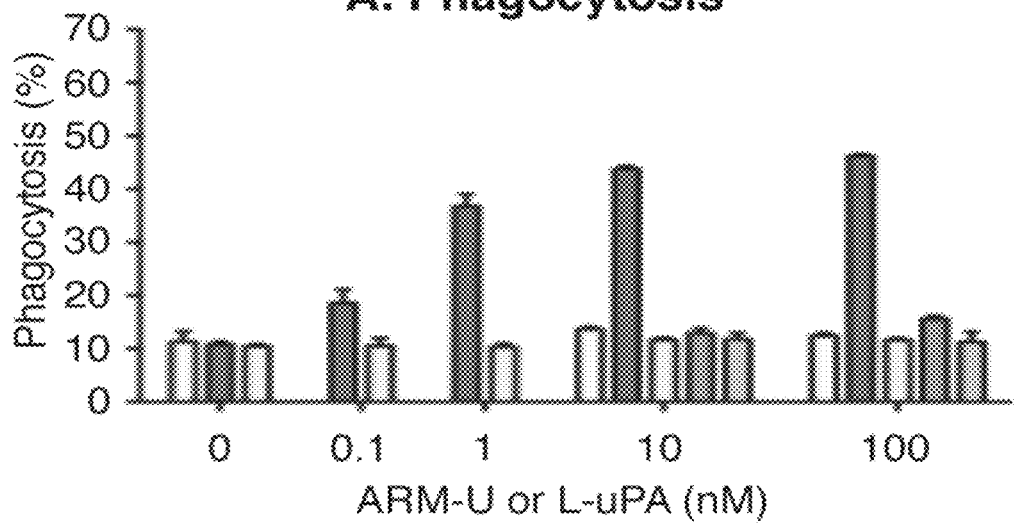
FIG. 4 (A) shows antibody-dependent phagocytosis of A172 cells by IFN-γ-primed U937 cells (16:1 effector: target). Antibody concentrations=10 µg/mL. Data points represent average values from triplicate experiments ±standard deviation. (B) Antibody-dependent cellular cytotoxicity, as measured by the Roche xCelligence System, of A172 cells by freshly isolated PBMCs (60:1 effector:target). Antibody concentration=27 µg/mL. At 3 h, the specific cytotoxicity was calculated as the specific decrease in cell index compared to cells treated with only anti-DNP antibody and PBMCs. Data points represent average values of triplicate experiments ±standard deviation.
Figure 4:
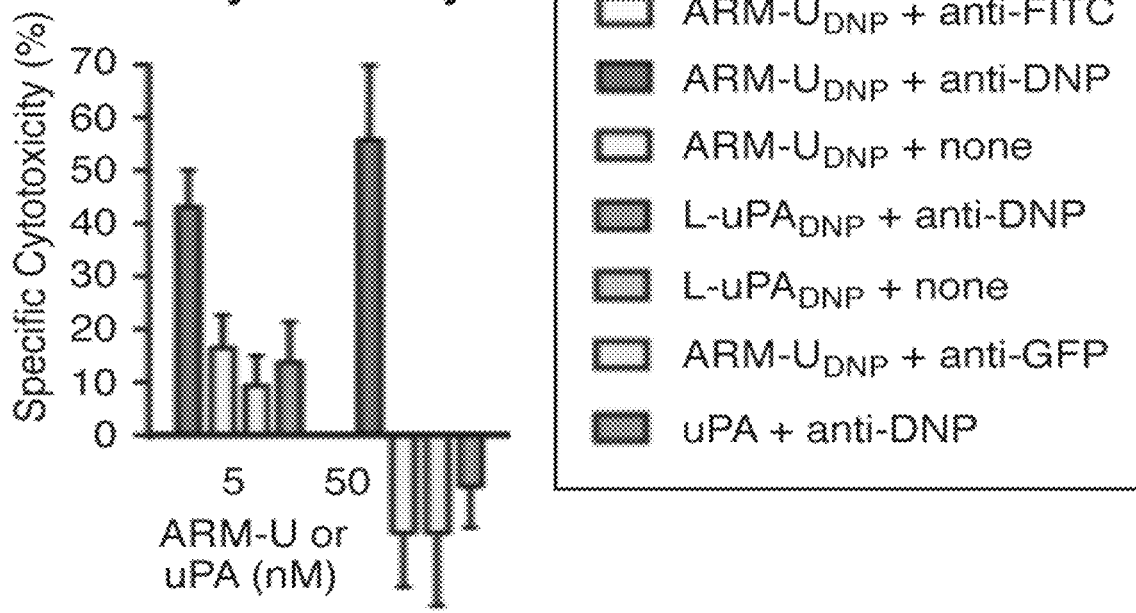
Figure 5:
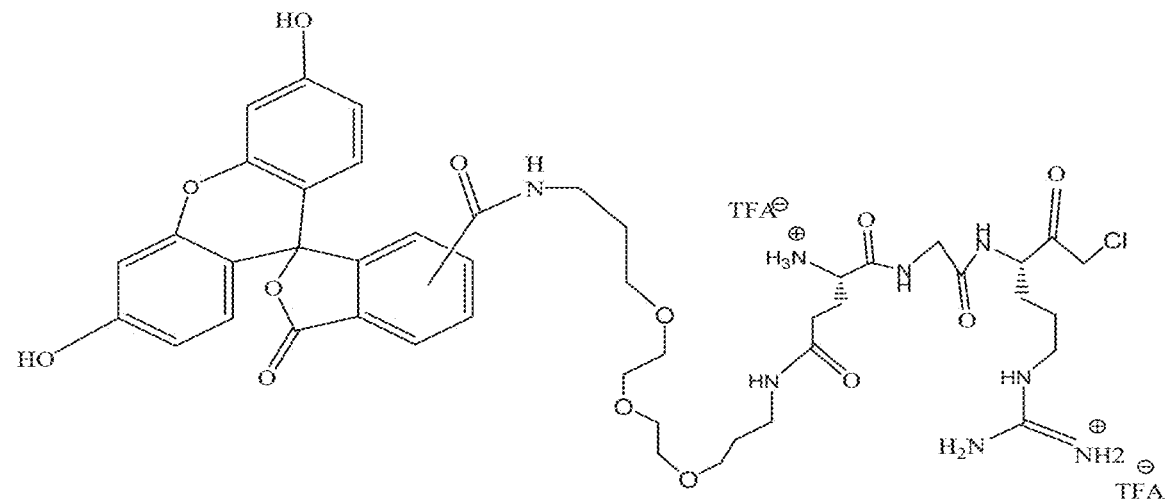
FIG. 5 shows exemplary compounds 1, 2 and 3, detailed synthetic procedures for which are set forth in the attached examples sections.
Figure 5:
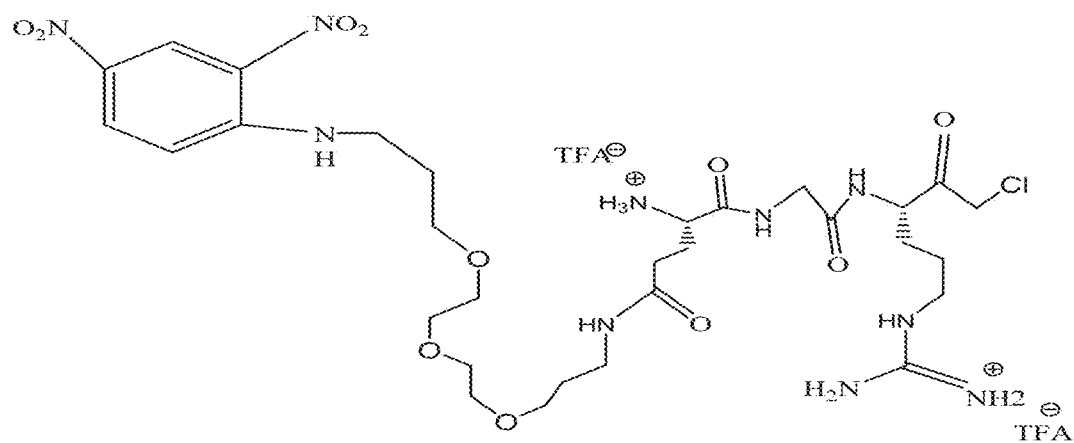
Figure 5:
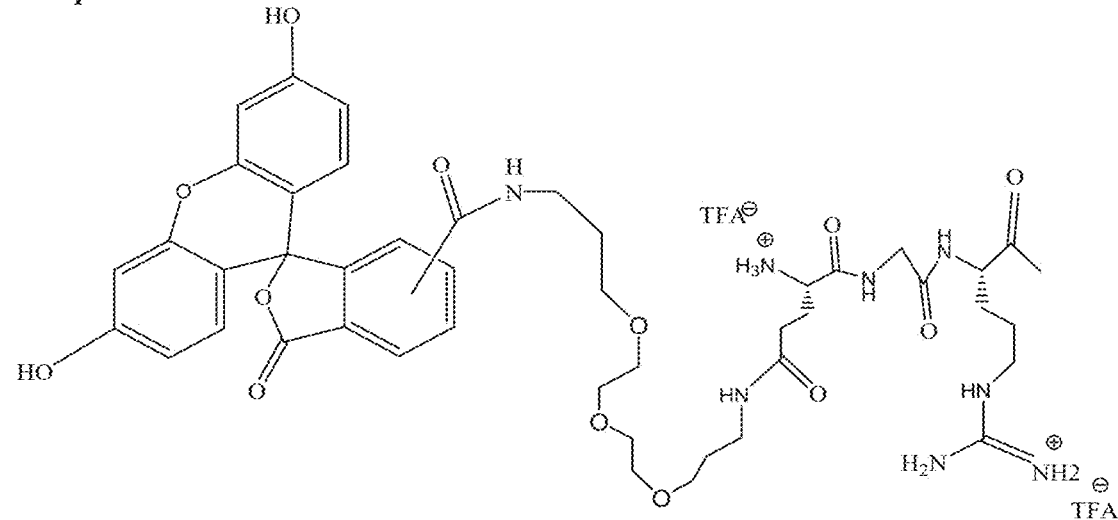

As illustrated in FIG. 4A, phagocytosis of A172 cells increases as a function of ARM-U$_{DNP}$ concentration (dark blue bars), and significant levels of phagocytosis are observed at ARM-U$_{DNP}$ concentrations as low as 0.1 nM. At 10 nM ARM-U$_{DNP}$, the level of observed phagocytosis is similar to that observed after non-specifically labeling the target cells with high levels of antigen (trinitrophenyl sulfonic acid incubation, Supplementary Figure S10), which indicates the high efficiency of ARM-U-mediated phagocytosis. Equivalently high levels of phagocytosis are observed when the pure anti-DNP antibody is replaced with serum from rabbits that had been immunized against the DNP hapten (Supplementary Figure S11). These results support the potential for ARM-U compounds to direct immune responses using serum as an antibody source without co-administration of purified antibodies. Indeed, the effect of antibody-recruiting molecules in hapten-immunized animal models has been studied.[xlii] In negative control experiments, an isotype-matched anti-fluorescein antibody (yellow bars), which does not bind DNP, was not found to promote phagocytosis, even at high ARM-U$_{DNP}$ concentrations. Furthermore, the adduct between low molecular weight uPA and compound 2 (L-uPA$_{DNP}$, red bars), which cannot bind uPAR, was also unable to promote phagocytosis even in the presence of anti-DNP antibody. In analogous assays (Supplementary Figure S10), the combination of ARM-U$_{Fluor}$ and anti-fluorescein antibody produces high levels of phagocytosis, underscoring the requirement for a matched antigen-antibody combination. ARM-U was also capable of mediating the phagocytic uptake of HT-29 cells (Supplementary Figure S11), albeit at slightly lower levels than for A172 cells, likely due to the slightly lower levels uPAR expression on the former cell line.[xxxix] Taken together, these data suggest that the observed phagocytosis is dependent upon ternary complexes formed between uPAR, ARM-U, and epitope-matched antibody on target cell surfaces.

We next studied the ability of ARM-U to induce antibody-dependent cellular cytotoxicity (ADCC). To this end, we utilized the Roche xCelligence System, which uses electrical impedance to measure the adhesion of live cells to gold electrodes in culture wells ("cell index"). Detachment of dying cells from these wells leads to a corresponding decrease in impedance through the gold electrodes, which has been used to measure cell death.[xliii,xliv] Treatment of A172 target cells with ARM-U$_{DNP}$, anti-DNP antibody, and freshly isolated human peripheral blood mononuclear cells (PBMCs) leads to profound time-dependent decreases in cell index that are indicative of ADCC (Supplementary Figure S12). Indeed, concentrations of ARM-U$_{DNP}$ as low as 5 nM led to substantial levels of cellular cytotoxicity in the presence of anti-DNP antibody (FIG. 4B, dark blue bars). Control conditions employing isotype-matched anti-green-fluorescence-protein antibody (green bars), unmodified uPA (tan bars), or omitting antibody altogether (light blue bars), indicated no decreases in cell viability. Additional control experiments conducted in the absence of PBMCs revealed no antibody-dependent cytotoxic effects (Supplementary Figures S14, S15). Together, these data suggest that ARM-U$_{DNP}$, effector cells, and anti-DNP antibody are required for cytotoxic effects. In light of the importance of ADCC in mediating the effects of monoclonal-antibody-based cancer therapeutics,[xiv] these data support a strong therapeutic potential for the proposed strategy.

DISCUSSION

In the present application, the inventors report a novel strategy for converting a cancer-promoting enzyme (uPA) into a synthetic construct (ARM-Us) capable of targeting cancer cells for immune-mediated destruction. Since the urokinase receptor is significantly upregulated on many types of cancer cells, especially the most invasive ones, ARM-U constructs have the potential to target a wide array of clinically relevant malignancies including those of the breast, colon, pancreas, and ovaries. Indeed, uPA and uPAR expression are well-documented markers for cancer aggressiveness and poor clinical outcome, and therapeutic-targeting strategies against these proteins have shown great promise.

The reported strategy has the potential to carry a number of advantages versus available anti-cancer therapeutics. For example, ARM-U reagents are formed by site-specifically modifying an endogenous human protein, these constructs are expected to be less likely to produce anaphylactoid or immunological side effects versus non-native proteins or their conjugates. Indeed, the catalytic domain of uPA (low-molecular-weight urokinase, trade name Abbokinase®) is already FDA-approved as a safe treatment for deep vein thrombosis and pulmonary embolism. Additionally, because uPAR is only expressed at low levels on healthy tissues, "off-target" cytotoxic effects should be minimal.[xxxvii]

Exploiting endogenous immunological mechanisms to selectively attack and eliminate cancer cells represents a relatively new strategy that has led to numerous developments in recent years. These successes range from Provenge®, an autologous cellular immunotherapy for prostate cancer treatment, to a variety of therapeutic antibodies. Despite these successes, only a few examples of small-molecule-based anti-cancer immunotherapeutics have been disclosed.[xxxviii,xxxix,xxx,xxxi,xxxii] The approach reported here differs from these prior strategies in that it exploits a naturally-occurring, high-affinity protein-protein interaction to target cancer cells, and it has the potential for efficacy in treating many types of invasive cancer cells due to the broadly upregulated uPAR marker. Finally, by enhancing trafficking of cancer-associated antigens through immune cells, ARM-Us have the potential to give rise to long-lasting immunity.[xxix] Although we focus here on targeting one cancer marker (uPAR) using a single endogenous antibody population (anti-DNP), one might envision ARM constructs that target various cancer-associated surface proteins. Thus, this general strategy holds promise for treating a wide range of human cancers and other diseases.

EXAMPLES

Detailed descriptions of materials and experimental procedures can be found in the examples which appear below.
Materials and Chemical Synthesis Organic chemicals were purchased from Sigma-Aldrich or Advanced ChemTech. High and low molecular weight human urokinase proteins were purchased from American Research Products or Innovative Research. Antibody reagents were purchased from Invitrogen or Rockland. HT-29, A172, and U937 cells were purchased from ATCC, grown according to the supplier's instructions, and used within 6 months of resuscitation. Molecules 1-3 were synthesized using standard organic chemistry procedures and characterized by standard techniques including $^1$H- and $^{13}$C-NMR spectroscopy, infrared (IR) spectroscopy, and mass spectrometry. Molecules 1-3 were purified to analytical purity using by preparative reverse phase HPLC.
Enzymatic Analysis uPA (10 µM) was incubated with either compound 1 (15 µM) or buffer at ambient temperature for 1 h and then diluted to 20 nM with a solution of Cbz-Gly-Gly-Arg-7-amino-4-methylcoumarin (96 QM). Fluorescence (330 nm absorbance, 460 nm emission) was monitored at 1 minute intervals. Initial rates of enzymatic hydrolysis were calculated from the increase in fluorescence signal using the first five data points.
SDS-PAGE Compound 1 (15 uM), compound 3 (60 uM), or buffer was mixed with uPA (10 uM) or buffer at ambient temperature for 1 h. Mixtures were loaded onto a 15% Tris-HCl SDS-PAGE gel, separated by electrophoresis, and visualized first by fluorescence (Typhoon Trio Variable Mode Imager, 488 nm excitation, 532 nm emission) and then by Coomassie stain.
ELISA The wells of a 96-well polystyrene plate were coated with rabbit IgG anti-human-uPA, treated either with ARM-U$_{Fluor}$ or uPA, treated with goat IgG anti-fluorescein, and treated with rabbit anti-goat-IgG conjugated to alkaline phosphatase. After addition of para-nitrophenyl phosphate, the rate of nitrophenol liberation was measured at 405 nm using a Synergy 2 Multimode Microplate Reader.
Flow Cytometry HT-29 cells were treated with ARM-U$_{Fluor}$ or the negative control L-uPA$_{Fluor}$, treated with rabbit anti-fluorescein IgG, and treated with with Alexa Fluor® 488-conjugated donkey anti-rabbit-IgG. Cells were analyzed by flow cytometry (FL-1 channel) on an Accuri C6 flow cytometer. No fluorescent signal above background was observed upon omission of the secondary antibody, indicating that the fluorescein moiety does not substantially contribute to observed fluorescent signal.
ADCP Assay Effector cells (U937) were treated with IFN-☐ for 2 days, then labeled with DiD, an FL-4 channel fluorophore. Target cells (A172 or HT-29) were labeled with DiO, an FL-1 channel fluorophore, then treated with ARM-U$_{DNP}$, ARM-U$_{Fluor}$, L-uPA$_{DNP}$, L-uPA$_{Fluor}$, trinitrophenyl sulphonic acid (TNP-SO$_3$H), or fluorocein isothiocyanate (FITC). Target and effector cells were mixed (16:1 effector:target), and antibody (10 ☐g/mL) was added. After 1 h at 37° C., the mixtures were analyzed by two-color flow cytometry. Effector cells that had performed phagocytosis were identified as those with strong signals in both the FL-1 and FL-4 fluorescence channels. Literature precedent supports that these double positive signals represent phagocytosis events rather than cell-cell aggregates.[xl] Percent phagocytosis is calculated using the following equation: Phagocytosis (%)=100× (double positive cells)/[(remaining target cells)+(double positive cells)].
ADCC Assay A172 cells were seeded into the analysis chamber of the Roche xCelligence System. After 12 hours, ARM-U$_{DNP}$ (5 or 50 nM), uPA, or buffer was added. Rabbit anti-DNP IgG (27 µg/mL), rabbit anti-green-fluorescence-protein (GFP) IgG, or buffer was also added simultaneously. Freshly isolated human peripheral blood mononuclear cells (60:1 effector:target) were then added. The xCelligence System's output is termed the "cell index" and is a function of the electrical impedance through gold electrodes on the surfaces of culture plates. All cell indices were normalized to 1.0 immediately following effector cell addition and were measured every 2 minutes. Normal growth is defined as that shown by target cells treated with anti-DNP antibody and effector cells, but no uPA or ARM-U. Specific cytotoxicity is calculated using the following equation: Specific cytotoxicity (%)=100−100×(cell index)/(normal growth cell index).
Detailed Chemical Synthesis
General Procedures Column chromatography was performed with 60 Å 40-63 µm silia-P flash silica gel. Solvents for reactions (acetonitrile, DMF, DCM, ether, THF, and toluene) were dried using a Glass Contour purification system. Other solvents were used as received. Bases (triethylamine, Hünig's base) were dried by distillation from calcium hydride. Chemicals were purchased from Aldrich or Advanced ChemTech and used as received unless noted otherwise. NMR Spectra were measured in CDCl$_3$ at ambient temperature unless otherwise noted. $^1$H NMR spectra were recorded on either a 500 or 400 MHz Bruker spectrometer. Chemical shifts are reported in ppm (δ) relative to tetramethylsilane using the solvent as a reference (CDCl$_3$=7.26 ppm, DMSO-d$_6$=2.49 ppm, D$_2$O=4.80 ppm, CD$_3$OD=3.30). The following is an example data point: chemical shift (multiplicity [s=singlet, d=doublet, t=triplet, q=quartet, pent=pentet, sext=sextet, sept=septet, oct=octet, m=multiplet, br=broad, and combinations thereof], coupling constants [Hz], integration, assignment [if any]). $^{13}$C NMR spectra were recorded on a 500 MHz (125 MHz) Bruker spectrometer with complete proton decoupling. Chemical shifts are reported in ppm (δ) relative to tetramethylsilane using the solvent or MeOH as a reference (CDCl$_3$=77.0 ppm, DMSO-d$_6$=39.5 ppm, CD$_3$OD=49.0 ppm, MeOH=49.5). $^{19}$F NMR spectra were recorded on a 400 MHz (375 MHz) Bruker spectrometer without proton decoupling. Chemical shifts are reported in ppm (δ) relative to trichlorofluoromethane. IR spectra were recorded on a Nicolet 6700 FT-IR spectrometer with OMNIC software, using a thin film from solution evaporation. Spectra are partially reported ($v_{max}$, cm$^{-1}$). HRMS was performed at The Keck Center at the Yale Medical School. Unless otherwise noted, data were obtained by positive mode electrospray ionization. TLC was performed on 60 Å F$_{254}$ precoated silica gel plates. Samples were visualized by either ultraviolet irradiation, potassium permanganate staining, or cerium ammonium molybdenate staining. LC/MS were run on a Waters Acquity LC system using an Acquity UPLC BEH C$_{18}$ column, a gradient of 20-100% (over 3 min) MeCN in water+0.1% formic acid, and a flow of 0.8 mL/min. Yield refers to isolated material.

Standard Synthetic Procedures

Hydrogenolysis Into a reaction vessel were added the starting benzyl ester or benzyloxycarbamate and methanol or 2-propanol (0.2 M, methanol generally gives better solubility and reactivity, but sometimes produces a methyl ester byproduct). Pd/C (10%, approximately 50-100 mg/mmol substrate) was added into another flask. The palladium-containing flask was capped with a septum and flushed with nitrogen. Methanol or isopropanol (equal to previous volume) was added by syringe, the flask was uncapped, and the slurry was transferred to the substrate solution. The mixture was capped and flushed with nitrogen (5 min). A hydrogen-filled balloon was attached such that its needle remained submerged, the flask was flushed briefly with hydrogen (30-60 sec), and the reaction was stirred at ambient temperature under the balloon's pressure (3 h). The balloon was removed, the flask was flushed with nitrogen, the mixture was filtered through Celite, and volatiles were removed under reduced pressure. Due to cleanliness of the reaction, the crude product was usually not purified further.

2. Synthetic Procedures

Scheme S1

Scheme S1, presented in FIG. 6, shows the synthetic strategy used to access compound (1).

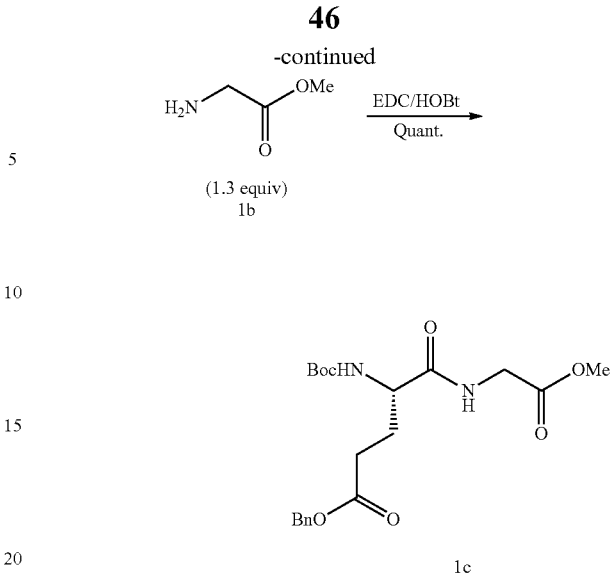

Synthesis of amide 1c Into a flask were added Boc-Glu(Bn)-OH (1a, 4.50 g, 13.4 mmol, 1 equiv), H-Gly-OMe hydrochloride (1b, 2.18 g, 17.4 mmol, 1.3 equiv), EDC hydrochloride (3.34 g, 17.4 mmol, 1.3 equiv), HOBt hydrate (2.66 g, 17.4 mmol, 1.3 equiv), DCM (67 mL, 0.2 M), DMF (30 mL, 0.4 M), and TEA (2.60 mL, 18.8 mmol, 1.4 equiv). The crude mixture was stirred (8 h) diluted with EtOAc (80 mL), washed with a 1:1:1 mixture of sodium bicarbonate (saturated), sodium carbonate (10%), and brine (120 mL), washed with sodium chloride (50% saturated, 2×80 mL), washed with a 1:1 mixture of citric acid (10%) and brine (60 mL), and dried with sodium sulfate. Volatiles were removed under reduced pressure to yield nearly pure amide 1c (quantitative), half of which was used directly in the next step. For analysis, an aliquot was purified by column chromatography (40 mL silica gel, [4:3] EtOAc/hexane). $^1$H NMR signals were assigned by $^1$H-$^1$H COSY.

$^1$H NMR (CDCl$_3$, 400 MHz) δ7.37-7.32 (m 5H, Bn), 6.82-6.73 (brs, 1H, Gly-NH), 5.32 (d, J=7.7 Hz, 1H, Boc-NH), 5.13 (s, 2H, Bn), 4.25 (q, J=7.0 Hz, 1H, Glu-α), 4.05 (dd, J$_1$=18.2 Hz, J$_2$=5.5 Hz, 1H, Gly-α), 3.99 (dd, J$_1$=18.3 Hz, J$_2$=5.5 Hz, 1H, Gly-α), 3.74 (s, 3H, OMe), 2.62-2.45 (m, 2H, Glu-γ), 2.22-2.12 (m, 1H, Glu-β), 2.01-1.91 (m, 1H, Glu-β), 1.43 (s, 9H, Boc); $^{13}$C NMR (CDCl$_3$, 125 MHz) δ173.06, 171.91, 155.64, 135.66, 128.48, 128.19, 128.14, 80.02, 66.44, 53.40, 52.23, 41.03, 30.28, 28.21, 27.84; IR (film, cm$^{-1}$) 1733, 1711, 1662, 1515, 1368, 1210, 1155, 730, 698; HRMS calculated for [C$_{20}$H$_{28}$N$_2$O$_7$H]$^+$, requires m/z=409.1969, found m/z=409.1967 (ESI); TLC (4:3) EtOAc/hexane, UV/permanganate, R$_f$=0.29.

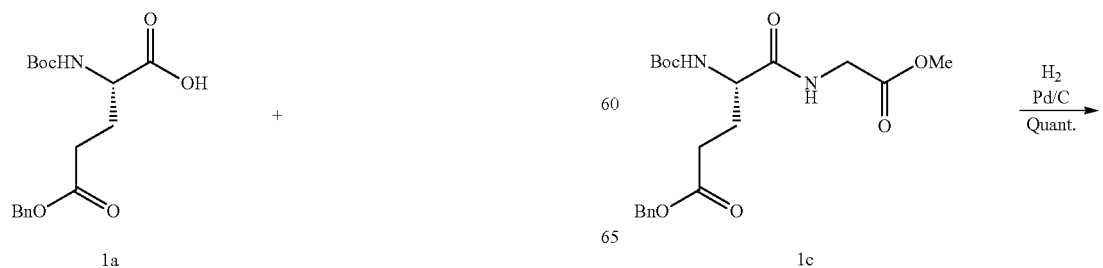

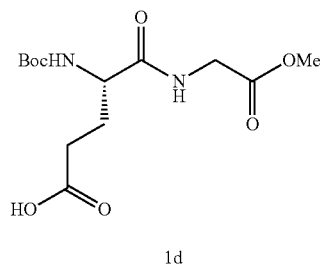

1d

Synthesis of acid 1c The standard hydrogenolysis was followed using crude peptide 1c (half, 6.7 mmol, 1.0 equiv), Pd/C (10%, 335 mg, 50 mg/mmol substrate), and MeOH (67 mL, 0.1 M) for 3 h to yield nearly pure acid 1d (quantitative), which was used directly in the next step. For analysis, an aliquot was purified by column chromatography (40 mL silica gel, [11:9:1] DCM/EtOAc/AcOH). $^1$H NMR signals were assigned by $^1$H-$^1$H COSY.

$^1$H NMR (DMSO-$d_6$, 500 MHz) δ8.23 (t, J=5.7 Hz, 1H, Gly-NH), 6.94 (d, J=9.3 Hz, 1H, Boc-NH), 3.98-3.92 (m, 1H, Glu-α), 3.88 (dd, $J_1$=17.4 Hz, $J_2$=6.0 Hz, 1H, Gly-α), 3.77 (dd, $J_1$=17.5 Hz, $J_2$=7.8 Hz, 1H, Gly-α), 3.61 (s, 3H, OMe), 2.30-2.22 (m, 2H, Glu-γ), 1.89-1.81 (m, 1H, Glu-β), 1.75-1.65 (m, 1H, Glu-β), 1.37 (s, 9H, Boc); $^{13}$C NMR (DMSO-$d_6$, 125 MHz) 3174.06, 172.29, 170.25, 155.29, 78.13, 53.41, 51.67, 40.57, 30.10, 28.18, 27.28; IR (film, cm$^{-1}$) 3318, 2974, 1708, 1667, 1516, 1246, 1213, 1160; HRMS calculated for $[C_{13}H_{22}N_2O_7H]^+$, requires m/z=319.1500, found m/z=319.1499 (ESI); TLC (11:9:1) DCM/EtOAc/AcOH, permanganate (faint), $R_f$=0.35.

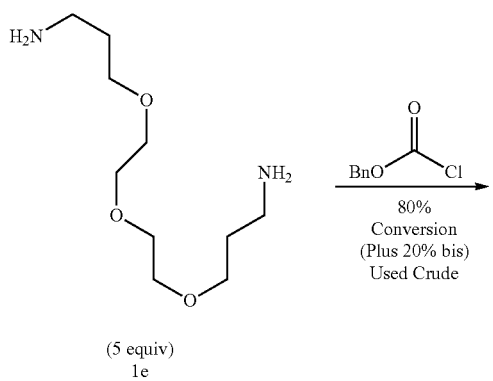

(5 equiv)
1e

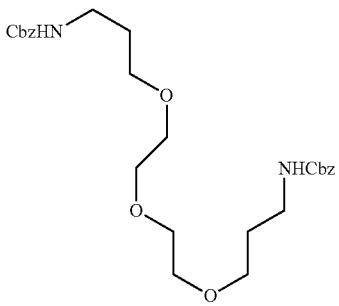

1g

Synthesis of carbamate 1e[1] Into a flask were added THF (200 mL, 0.1 M), 4,7,10-trioxa-1,13-tridecanediamine (1e, 22.0 mL, 100 mmol, 5 equiv), triethylamine (2.77 mL, 20.0 mmol, 1.0 equiv), and MeOH (70 mL, 0.3 M). The flask was fitted with an addition funnel, maintained under a nitrogen atmosphere, and cooled in an ice bath (0° C.). Benzyl chloroformate (2.84 mL, 20.0 mmol, 1 equiv) was dissolved in THF (100 mL, 0.2 M) and added dropwise (over 45 min) to the reaction mixture. The reaction was allowed to warm to ambient temperature and stirred (30 min). Volatiles were removed under reduced pressure. The crude mixture was diluted with brine (200 mL) and sodium carbonate (10% aqueous, 40 mL), extracted with ether (150+2×100 mL), washed with brine (100 mL), and dried with sodium sulfate. Volatiles were removed under reduced pressure, to yield a mixture (approximately 4:1) of monocarbamate 1f and dicarbonate 1g, which was used directly for the next step. Product analysis is consistent with reported data.[1]

[1] Carbamate-formation procedure and compound data from: Harris, T. D., Kalogeropoulos, S., Nguyen, T., Dwyer, G., Edwards, D. S., Liu, S., Bartis, J., Ellars, C., Onthank, D., Yalamanchili, P., Heminway, S., Robinson, S., Lazewatsky, J., Barrett, J. (2006) *Bioconj. Chem.* 17, 1294.

Crude monocarbamate 1f: $^1$H NMR (CDCl$_3$, 500 MHz) δ7.36-7.28 (m 5H, Bn), 5.58-5.52 (brs, 1H, NHZ), 5.09 (s, 2H, Bn), 3.65-3.45 (m, 12H, 6×CH$_2$—O), 3.33-3.27 (m, 2H, CH$_2$—NHZ), 2.77 (t, J=6.8 Hz, 2H, CH$_2$—NH$_2$), 1.80-1.66 (m, 4H, 2×C—CH$_2$—C).

Crude dicarbamate 1g: $^1$H NMR (CDCl$_3$, 500 MHz) δ7.36-7.28 (m 10H, 2×Bn), 5.36-5.30 (brs, 2H, 2×NHZ), 5.09 (s, 4H, 2×Bn), 3.65-3.45 (m, 12H, 6×CH$_2$—O), 3.33-3.27 (m, 4H, 2×CH$_2$—NHZ), 1.80-1.66 (m, 4H, 2×C—CH$_2$—C).

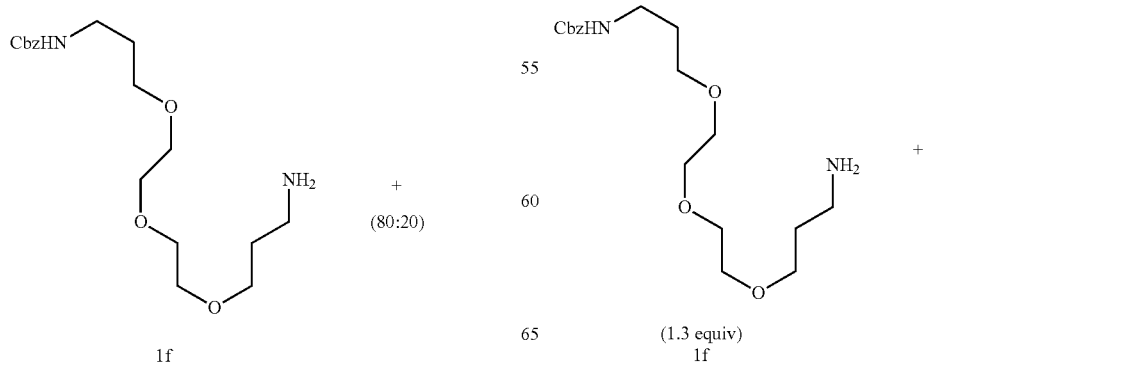

(80:20)

1f (1.3 equiv)
1f

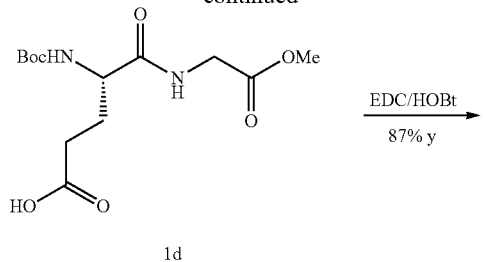

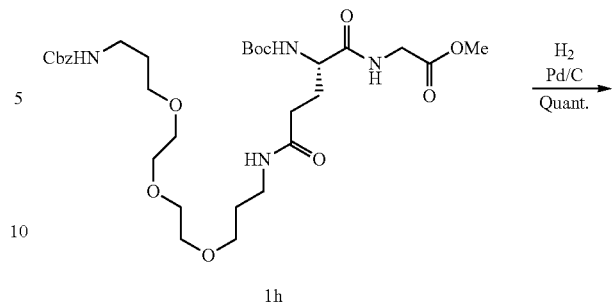

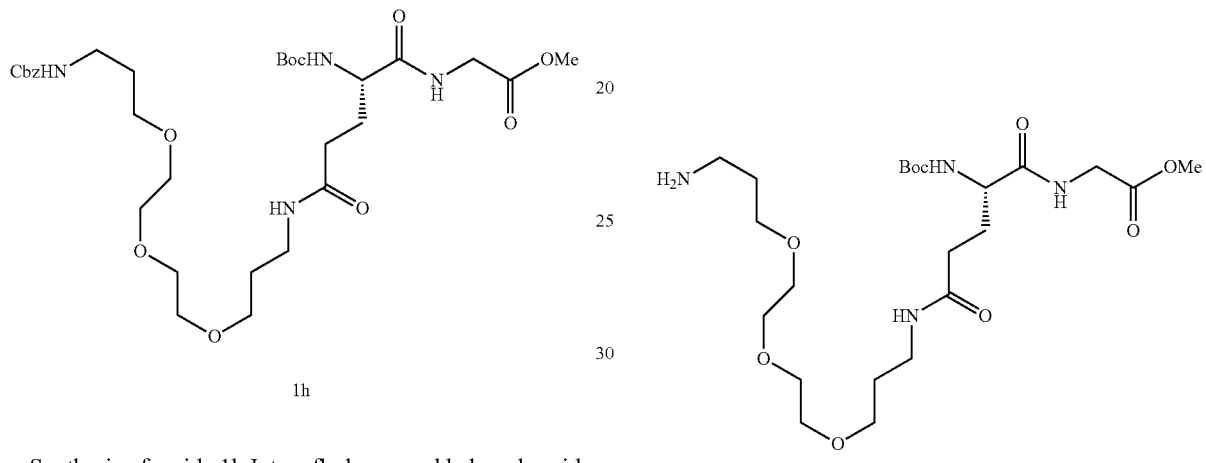

Synthesis of amide 1h Into a flask were added crude acid 1d (6.70 mmol, 1 equiv), crude amine 1f (8.71 mmol, 1.3 equiv), EDC hydrochloride (1.67 g, 8.71 mmol, 1.3 equiv), HOBt hydrate (1.33 g, 8.71 mmol, 1.3 equiv), and DCM (35 mL, 0.2 M). The crude mixture was stirred (15 h) diluted with DCM (40 mL), washed with a mixture (1:1, 50 mL) of sodium bicarbonate (saturated) and sodium carbonate (10%), washed with a mixture (1:1, 50 mL) of citric acid (10%) and brine (60 mL), and dried with sodium sulfate. Volatiles were removed under reduced pressure, and the crude mixture was purified by column chromatography (250 mL silica gel, [4:1 to 1:1] DCM/acetone) to yield amide 1h (3.82 g, 5.84 mmol, 87% yield from glutamic acid 1a). $^1$H NMR signals were assigned by $^1$H-$^1$H COSY.

$^1$H NMR (DMSO-$d_6$, 500 MHz) δ8.20 (t, J=6.0 Hz, 1H, Gly-NH), 7.74 (t, J=5.8 Hz, 1H, Glu-γ-NH), 7.38-7.28 (m 5H, Bn), 7.20 (t, J=5.6 Hz, 1H, Cbz-NH), 6.88 (d, J=8.0 Hz, 1H, Boc-NH), 4.99 (s, 2H, Bn), 3.95-3.90 (m, 1H, Glu-α), 3.87 (dd, $J_1$=17.2 Hz, $J_2$=3.8 Hz, 1H, Gly-α), 3.79 (dd, $J_1$=17.7 Hz, $J_2$=6.0 Hz, 1H, Gly-α), 3.61 (s, 3H, OMe), 3.51-3.42 (m, 8H, 4×CH$_2$—O), 3.37 (q, J=6.0 Hz, 4H, 2×CH$_2$—C—C—N), 3.08-3.00 (m, 4H, 2×CH$_2$—NHCO), 2.14-2.07 (m, 2H, Glu-γ), 1.90-1.80 (m, 1H, Glu-β), 1.73-1.65 (m, 1H, Glu-β), 1.64-1.55 (m, 4H, 2×C—CH$_2$—C), 1.37 (s, 9H, Boc); $^{13}$C NMR (DMSO-$d_6$, 125 MHz) δ172.41, 171.53, 170.24, 156.10, 155.24, 137.27, 128.33, 127.75, 127.72, 78.09, 69.76, 69.55, 68.09, 67.95, 65.14, 53.81, 51.65, 40.56, 37.64, 35.82, 31.77, 29.64, 29.35, 28.18, 28.01; IR (film, cm$^{-1}$) 3315, 2935, 2867, 1700, 1656, 1529, 1248; HRMS calculated for [C$_{31}$H$_{50}$N$_4$O$_{11}$H]$^+$, requires m/z=655.3549, found m/z=655.3513 (ESI); TLC (1:1) DCM/acetone, permanganate, $R_f$=0.32.

Synthesis of amine 1i The standard hydrogenolysis was followed using carbamate 1h (1.31 g, 2.00 mmol, 1 equiv, methanol azeotrope to remove any remaining acetone), Pd/C (10%, 160 mg, 80 mg/mmol substrate), and MeOH (20 mL, 0.1 M) for 2.5 h to yield nearly pure amine 1i (quantitative), which was used directly in the next step. $^1$H NMR signals were assigned by $^1$H-$^1$H COSY.

Crude Amine 1i: $^1$H NMR (DMSO-$d_6$, 500 MHz. major signals) δ 8.22 (t, J=7.6 Hz, 1H, Gly-NH), 7.80-7.67 (m, 1H, Glu-γ-NH), 6.90 (d, J=8.2 Hz, 1H, Boc-NH), 3.95-3.88 (m, 1H, Glu-α), 3.87 (dd, $J_1$=17.6 Hz, $J_2$=5.3 Hz, 1H, Gly-α), 3.79 (dd, $J_1$=17.4 Hz, $J_2$=5.6 Hz, 1H, Gly-α), 3.61 (s, 3H, OMe), 3.52-3.35 (m, 12H, 6×CH$_2$—O), 3.05 (q, J=6.3 Hz, 2H, CH$_2$—NHCO), 2.56 (t, J=6.8 Hz, 2H, CH$_2$—NH$_2$), 2.15-2.05 (m, 2H, Glu-γ), 1.90-1.80 (m, 1H, Glu-β), 1.73-1.64 (m, 1H, Glu-β), 1.64-1.52 (m, 4H, 2×C—CH$_2$—C), 1.37 (s, 9H, Boc); $^{13}$C NMR (DMSO-$d_6$, 125 MHz, major signals) δ 172.35, 171.46, 170.19, 155.18, 78.02, 69.78, 69.76, 69.52, 69.49, 68.42, 68.06, 53.77, 51.61, 40.52, 38.71, 35.78, 33.09, 31.73, 29.33, 28.15; IR (film, cm-1) 3305, 2933, 2872, 1658, 1524, 1160, 1095; HRMS calculated for [C$_{23}$H$_{44}$N$_4$O$_9$H]$^+$, requires m/z=521.3181, found m/z=521.3172 (ESI). LC/MS elutes at 0.65 min, calculated for [C$_{23}$H$_{44}$N$_4$O$_9$H]$^+$, requires m/z=521.32, found m/z=521.22 (ESI).

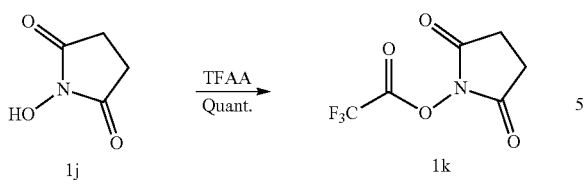

Synthesis of trifluoroacetate 1k[2] Into a flame-dried flask backfilled with argon were added N-hydroxysuccinimide (2.30 g, 20.0 mmol, 1 equiv) and THF (40 mL, 0.5 M, producing a cloudy solution). The flask was capped with a rubber septum and maintained in an ambient temperature water bath. Trifluoroacetic anhydride (5.68 mL, 40.0 mmol, 2 equiv) was added by syringe dropwise (over 5 min). The mixture was stirred (2 h) and diluted with toluene (20 mL). Volatiles were removed under reduced pressure (3×20 mL toluene azeotrope) to yield mostly pure trifluoroacetate 1k (quantitative, as fluffy white solid), which was used directly for the next step. Acetate 1k is somewhat moisture sensitive, so it was used within a few hours of its synthesis.

[2] a) Procedure from: Dey, S., Pappin, J. C., Purkayastha, S., Pillai, S., Coull, J. M. U.S. Patent 2005/0148771, Jul. 7, 2005. b) also see: Sadakibara, S., Inukai, N. (1964) *Bull. Chem. Soc. Jap.* 37, 1231.

Crude 1k: $^1$H NMR (CDCl$_3$, 400 MHz, major signal) δ 2.91 (s, 4H); $^{13}$C NMR (CDCl$_3$, 125 MHz, major signals) δ 167.14, 153.66 (q, J=46.0 Hz), 113.87 (q, J=286.1 Hz), 25.51; $^{19}$F NMR (CDCl$_3$, 375 MHz, major signal) δ −72.69.

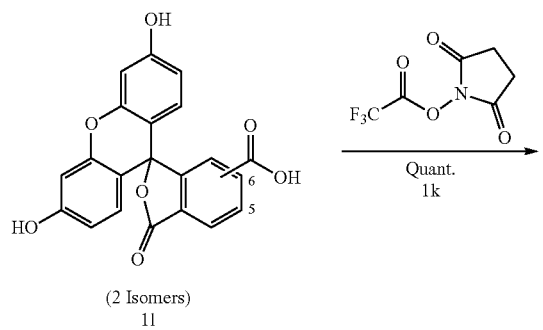

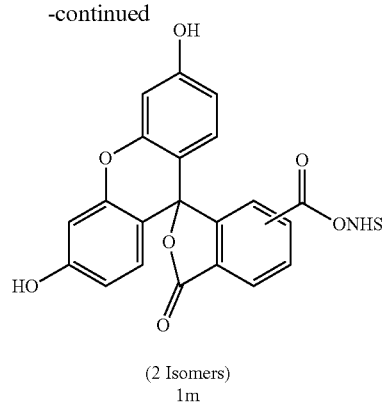

(2 Isomers)
1m

Synthesis of succinimide 1m Crude trifluoroacetate 1k (20.0 mmol, 5 equiv) was placed in a flask. The flask was backfilled with argon, capped with a rubber septum, and maintained under an argon atmosphere. To the flask were added THF (15 mL, 0.2 M) and 5(6)-carboxyfluorescein (1l, 1.13 g, 3.00 mmol, 1 equiv, 1:1 mixture of two isomers, producing a suspension). Pyridine (1.69 mL, 21.0 mmol, 7 equiv) was added by syringe dropwise (over 3 min, slightly exothermic). The mixture was stirred in the dark (3 h, producing a homogeneous solution), quenched with water (5 mL, 5 min), and diluted with DCM (45 mL) and water (50 mL). The organic phase was isolated, the aqueous phase was further extracted with a mixture of DCM and THF (3:1, 25 mL), and the combined organic phases were washed with sodium bisulfate (0.1 M aqueous, 40 mL) and dried with sodium sulfate. Volatiles were removed under reduced pressure to yield nearly pure succinimide 1m (1:1 mixture of isomers, quantitative), which was used directly for the next step. Compound analysis is consistent with commercially available material.[3]

[3] 5(6)-Carboxyfluorescein N-hydroxysuccinimide ester can be purchased from Sigma-Aldrich Crude ester 1m: $^1$H NMR (DMSO-d$_6$, 500 MHz, major signals) δ 10.18 (s, 1H, 2×OH), 10.17 (s, 1H, 2×OH), 8.52 (dd, J$_1$=1.5 Hz, J$_2$=0.5 Hz, 0.5H), 8.41 (dd, J$_1$=8.1 Hz, J$_2$=1.6 Hz, 0.5H), 8.37 (dd, 1=8.1 Hz, J$_2$=1.5 Hz, 0.5H), 8.24 (dd, J$_1$=8.0 Hz, J$_2$=0.7 Hz, 0.5H), 7.90 (dd, J$_1$=1.4 Hz, J$_2$=0.7 Hz, 0.5H), 7.54 (dd, J$_1$=8.1 Hz, J$_2$=0.7 Hz, 0.5H), 6.70-6.63 (m, 4H), 6.56-6.52 (m, 2H), 2.95-2.90 (brs, 2H), 2.88-2.84 (brs, 2H).

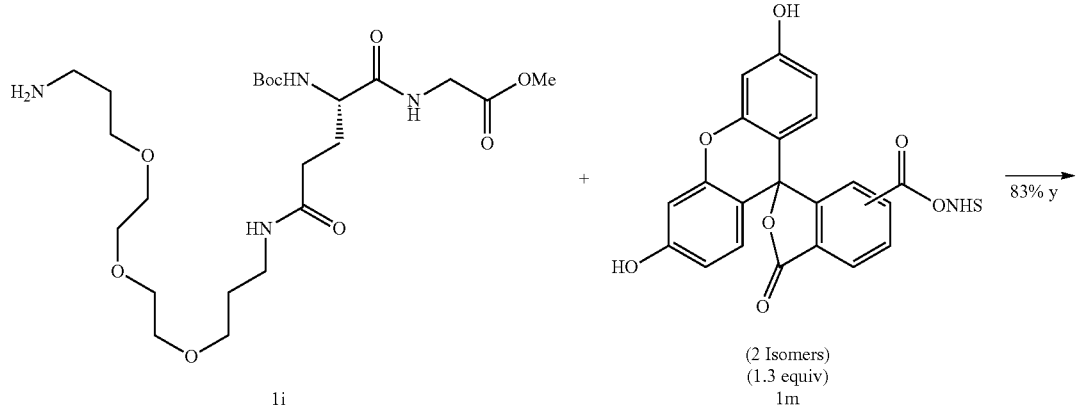

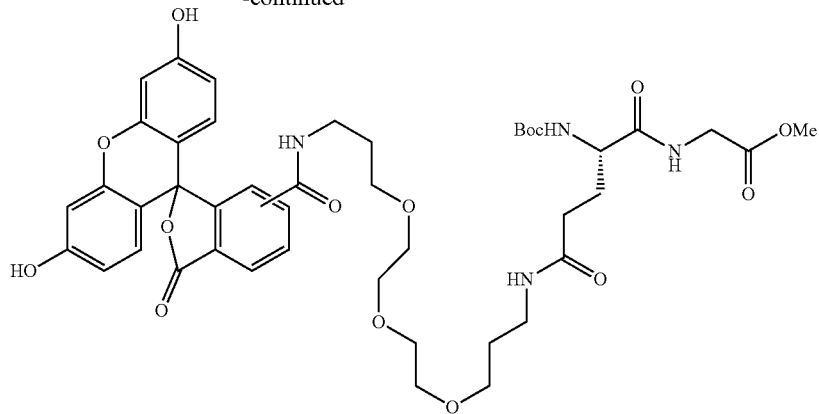

(2 Isomers)
1n

Synthesis of amide 1n Into a flask were added crude amine 1i (0.76 mmol, 1 equiv), DCM (8 mL, 0.1M) and a solution of crude ester 1m (1.0 mmol, 1.3 equiv) in THF (8 mL, 0.1 M). The mixture was stirred in the dark (slightly exothermic, changing from yellow to red, 17 h). As analysis showed only partial consumption of starting materials, Hünig's base (170 µL, 1.00 mmol, 1.3 equiv) was added, and the mixture was stirred (additional 3 h). Analysis showed nearly full consumption of amine 1i. The reaction was quenched by adding butylamine (0.2 mL, 2 mmol, 3 equiv, stirred 1 h) and diluted with THF (20 mL), DCM (40 mL), and citric acid (5% aqueous, 40 mL). The organic phase was isolated, the aqueous phase was further extracted with a mixture of DCM and THF (3:1, 40 mL), and the combined organic phases were dried with sodium sulfate. Volatiles were removed under reduced pressure, and the crude material was purified by column chromatography (60 mL silica gel, [1:1 to 5:1] acetone/EtOAc) to yield amide 1n (1:1 mixture of isomers, 552 mg, 629 mmol, 83% yield from benzyloxy carbamate 1h). $^1$H NMR signals were assigned by $^1$H-$^1$H COSY.

$^1$H NMR (CD$_3$OD, 500 MHz) δ 8.42-8.40 (m, 0.5H, Ar), 8.19 (dd, $J_1$=8.0 Hz, $J_2$=1.6 Hz, 0.5H, Ar), 8.12 (dd, $J_1$=8.1 Hz, $J_2$=1.4 Hz, 0.5H, Ar), 8.05 (dd, $J_1$=8.1 Hz, $J_2$=0.5 Hz, 0.5H, Ar), 7.64-7.63 (m, 0.5H, Ar), 7.29 (dd, $J_1$=8.1 Hz, $J_2$=1.3 Hz, 0.5H, Ar), 6.68-6.50 (m, 6H, Ar), 4.10-4.05 (m, 1H, Glu-α), 3.98 (d, J=17.6 Hz, 1H, Gly-ax), 3.89 (d, J=17.7 Hz, 1H, Gly-α), 3.70-3.35 (m, 17H, OMe, 6×CH$_2$—O, CH$_2$—NHCO), 3.25-3.15 (m, 2H, CH2-NHCOAr), 2.29 (q, J=7.7 Hz, 2H, Glu-γ), 2.10-2.00 (m, 1H, Glu-β), 1.93-1.83 (m, 2H, Glu-β, C—CH$_2$—C), 1.77 (pent, J=6.3 Hz, 1H, C—CH$_2$—C), 1.70 (pent, J=6.5 Hz, 1H, C—CH$_2$—C), 1.65 (pent, J=6.5 Hz, 1H, C—CH$_2$—C), 1.43 (s, 9H, Boc); $^{13}$C NMR (CD$_3$OD, 125 MHz) δ175.04, 174.89, 171.60, 170.53, 168.12, 167.84, 161.29, 157.68, 153.95, 153.93, 142.38, 137.91, 135.50, 130.40, 130.31, 130.25, 130.13, 128.54, 126.14, 125.66, 124.77, 123.88, 113.70, 110.88, 110.82, 103.63, 103.61, 80.72, 71.47, 71.45, 71.24, 71.15, 71.13, 71.04, 70.89, 70.22, 70.15, 69.86, 69.79, 55.42, 52.63, 41.82, 39.07, 38.96, 37.90, 37.85, 30.30, 30.28, 30.03, 29.36, 28.71, 26.26; IR (film, cm$^{-1}$) 1751, 1632, 1617, 1447, 1245, 1215, 1179, 1107; HRMS calculated for [C$_{44}$H$_{54}$N$_4$O$_{15}$H]$^+$, requires m/z=879.3658, found m/z=879.3667 (ESI); TLC (6:1) acetone/EtOAc, yellow, R$_f$=0.50.

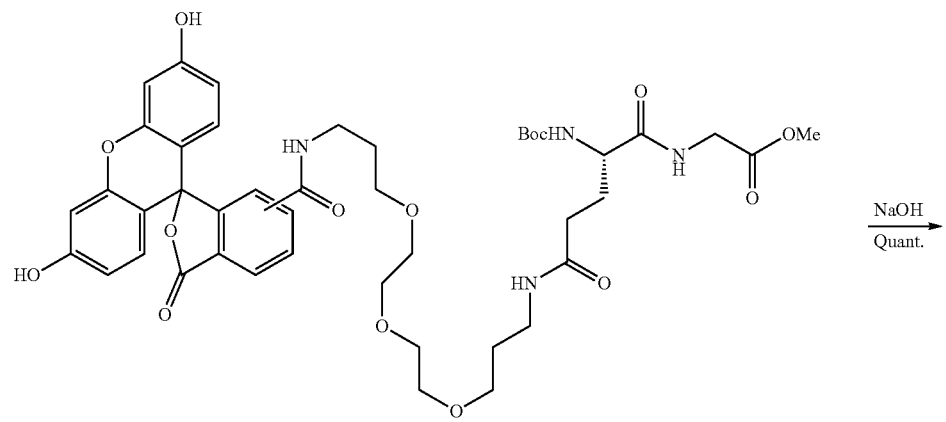

(2 Isomers)
1n

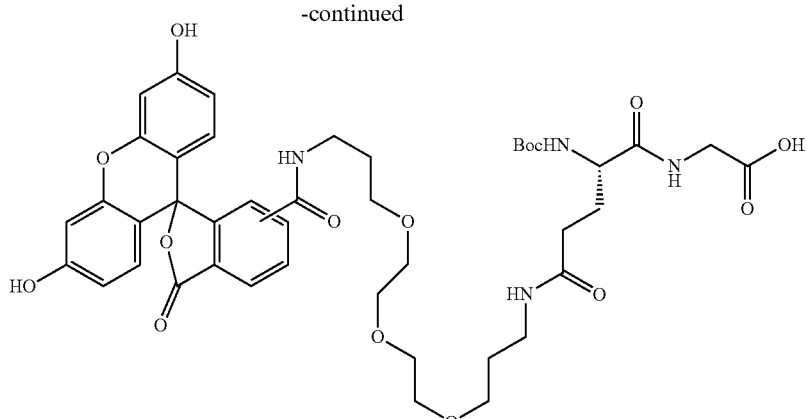

(2 Isomers)
1o

Synthesis of acid 1o Into a flask were added ester 1n (832 mg, 0.948 mmol, 1 equiv), dioxane (10 mL, 0.1 M), water (4 mL), and sodium hydroxide (1 M aqueous, 6 mL, 6 mmol, 6 equiv). The mixture was stirred in the dark (4 h) and neutralized with hydrochloric acid (2 M aqueous, until the color changed from brown to pale orange, approximately pH 4). Volatiles were removed by lyophilization to yield mostly pure acid 1o, which was used directly for the next step.

$^1$H NMR (CD$_3$OD, 500 MHz, major signals) δ 8.42 (d, J=1.9 Hz, 0.5H, Ar), 8.05 (d, J=8.9 Hz, 0.511, Ar), 8.02 (dd, J$_1$=8.2 Hz, J$_2$=1.6 Hz, 0.5H, Ar), 7.97 (dd, J$_1$=7.8 Hz, J$_2$=1.9 Hz, 0.511, Ar), 7.66 (d, J=1.3 Hz, 0.5H, Ar), 7.31 (d, J=7.9 Hz, 0.5H, Ar), 7.05-7.00 (m, 2H, Ar), 6.55-6.50 (m, 4H, Ar), 4.08-4.02 (m, 1H, Glu-α), 3.75-3.72 (m, 2H, Gly-α), 3.70-3.40 (m, 14H, 6×CH$_2$—O, CH$_2$—NHCO), 3.27-3.18 (m, 2H, CH2-NHCOAr), 2.27 (q, J=7.4 Hz, 2H, Glu-γ), 2.12-2.00 (m, 1H, Glu-β), 1.96-1.83 (m, 3H, Glu-β, C—CH$_2$—C), 1.77-1.68 (m, 2H, C—CH$_2$—C), 1.43 (s, 9H, Boc); LC/MS elutes at 0.89 min, calculated for [C$_{43}$H$_{52}$N$_4$O$_{15}$H]$^+$, requires m/z=865.35, found m/z=865.35 (ESI).

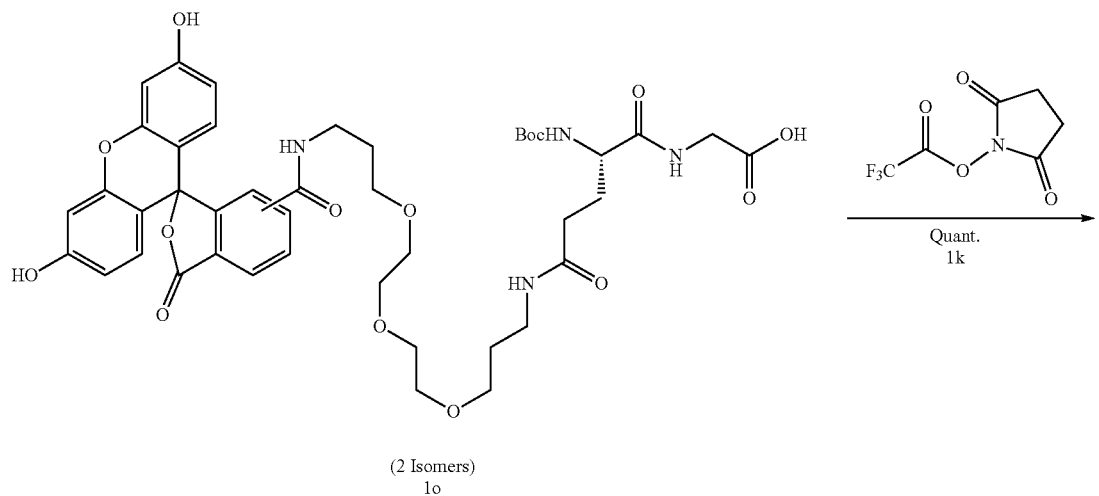

(2 Isomers)
1o

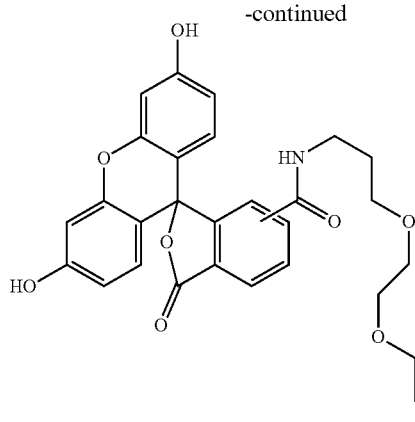

(2 Isomers)
1p

Synthesis of ester 1p Into a flask were added crude acid to (0.948 mmol, 1 equiv), THF (20 mL, 0.05 M, producing a suspension), pyridine (398 µL, 4.93 mmol, 5.2 equiv), and trifluoroacetate 1k (1.00 g, 4.74 mmol, 5 equiv). The suspension was maintained under an argon atmosphere, stirred in the dark (2 h, mostly dissolving and showing full conversion by LC/MS), quenched with water (10 mL, 3 min), and diluted with additional water (30 mL) and DCM (40 mL). The organic phase was isolated and the aqueous phase was further extracted with a mixture of DCM and THF (2:1, 30 mL). The combined organic phases were washed with sodium bisulfate (0.1 M, 60 mL) and dried with sodium sulfate. Volatiles were removed under reduced pressure to yield mostly pure ester 1p (quantitative), which was used directly for the next step. Ester 1p decomposes on silica gel.

$^1$H NMR (CD$_3$OD, 500 MHz, major signals) δ 8.41 (s, 0.5H, Ar), 8.19 (d, J=8.4 Hz, 0.5H, Ar), 8.14 (d, J=8.5 Hz, 0.5H, Ar), 8.07 (d, J=9.0 Hz, 0.5H, Ar), 7.64 (s, 0.5H, Ar), 7.30 (d, J=8.6 Hz, 0.5H, Ar), 6.70-6.67 (m, 2H, Ar), 6.64-6.51 (m, 4H, Ar), 4.36 (d, J=18.5 Hz, 1H, Gly-α), 4.26 (d, J=17.9 Hz, 1H, Gly-α), 4.10-4.04 (m, 1H, Glu-α), 3.67-3.35 (m, 14H, 6×CH$_2$—O, CH$_2$NHCO), 3.25-3.15 (m, 2H, CH2-NHCOAr), 2.81 (s, 4H, NHS), 2.27 (q, J=8.8 Hz, 2H, Glu-γ), 2.09-1.97 (m, 1H, Glu-β), 1.95-1.62 (m, 5H, Glu-β, 2×C—CH$_2$—C), 1.41 (s, 9H, Boc); LC/MS elutes at 1.03 min, calculated for [C$_{47}$H$_{55}$N$_5$O$_{17}$H]$^+$, requires m/z=962.37, found m/z=962.32 (ESI).

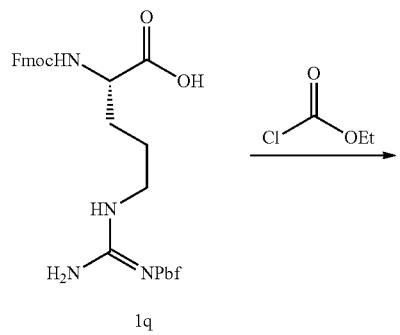

1q

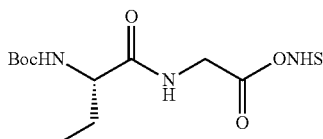

-continued

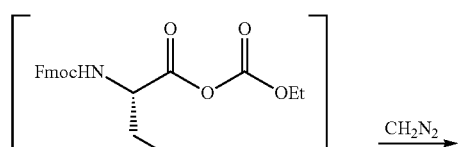

1r

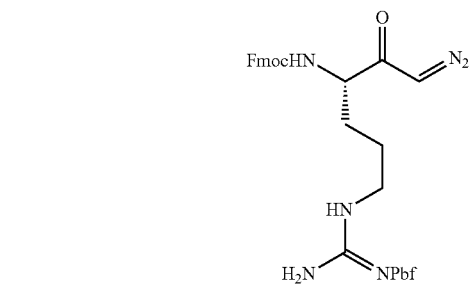

1s

Synthesis of ketone 1s[4] Into a flame-dried flask backfilled with argon was added Fmoc-Arg(Pbf)-OH (1q, 1.95 g, 3.0 mmol, 1 equiv). The flask was capped with a septum and maintained under an argon atmosphere. THF (15 mL, 0.2 M) was added, and the flask was cooled in a water/methanol/dry ice bath (−30° C.). N-Methylmorpholine (395 µL, 3.60 mmol, 1.2 equiv) was added, and the flask was allowed to equilibrate (10 min). Ethyl chloroformate (317 µL, 3.30 mmol, 1.1 equiv) was added dropwise by syringe (producing precipitate). The mixture was stirred (1 h), quickly filtered into a fire-polished, argon-filled, −30° C. flask, and chased with cold THF (15 mL). The filtrate was maintained at −30° C., and used directly for the next step. Mixed anhydride 1r decomposes if it is allowed to warm to ambient temperature.

[4] Procedure modified from and compound data from: Rueping, M., Mahajan, Y. R., Jaun, B., Seebach, D. (2004) *Chem. Eur. J.* 10, 1607.

Diazomethane was generated in specially prepared fire-polished glassware behind a strong blast shield. Extra caution was used while working with this explosive and toxic gas. Potassium hydroxide (1.01 g, 18.0 mmol, 6 equiv) was dissolved in water (5 mL, exothermic) and poured into the reaction chamber. To the hydroxide solution were added diethylene glycol ethyl ether (10 mL) and ether (10 mL, producing a biphasic mixture). No stirbar was used. The reaction chamber was flushed with argon. The attached cold finger was cooled with a mixture of iPrOH and dry ice. The anhydride-containing flask (−30° C.) was used as the collection flask, and the vent was passed through a bubbler filled with acetic acid. Diazald (1.93 g, 9.00 mmol, 3 equiv) was dissolved in ether (20 mL) and added to the addition funnel. The reaction chamber was warmed in an oil bath (65° C., oil level at ether-water interface). As the ether began to distill, the Diazald solution was added dropwise (over 20 min) to maintain a constant amount of ether in the reaction chamber. Within a few minutes the distillate became yellow. The Diazald solution was chased with ether (2×5 mL, after which the distillate had returned to colorless). The oil bath was removed, and the system was maintained under argon (1 h). The cold bath (−30° C.) was exchanged for an ice bath (0° C., additional 2 h). The glassware was removed from the collection flask. The reaction was quenched with acetic acid (dropwise from a blunt plastic syringe until bubbling ceased), diluted with a mixture (1:1, 40 mL) of sodium bicarbonate (saturated aqueous) and brine, extracted with ether (50 mL), washed with ammonium chloride (50% saturated aqueous), and dried with sodium sulfate. Volatiles were removed under reduced pressure, and the crude material was purified by column chromatography (100 mL silica gel, [1:1 to 2:1] EtOAc/DCM) to yield ketone 1s (1.45 g, 2.15 mmol, 72% yield). Ketone 1s is stable for at least several months at −20° C.

Compound analysis is consistent with published data.[4] $^{1}$H NMR (CDCl$_3$, 500 MHz) δ7.74 (d, J=7.6 Hz, 2H, Fmoc), 7.56 (d, J=7.7 Hz, 2H, Fmoc), 7.37 (t, J=7.4 Hz, 2H, Fmoc), 7.28-7.25 (m, 2H, Fmoc), 6.15-5.95 (brm, 3H, 3×guan-NH), 5.86 (d, J=8.2 Hz, 1H, Fmoc-NH), 5.55-5.50 (brs, 1H, CH=N$_2$), 4.43-4.35 (m, 2H, Fmoc), 4.22-4.12 (m, 2H, Fmoc, Arg-α), 3.32-3.15 (m, 2H, Arg-δ), 2.91 (s, 2H, Pbf), 2.58 (s, 3H, Pbf), 2.50 (s, 3H, Pbf), 2.07 (s, 3H, Pbf), 1.85-1.77 (m, 1H, Arg-β/γ), 1.65-1.50 (m, 3H, Arg-β/γ), 1.43 (s, 6H, Pbf); TLC (3:2) EtOAc/DCM, UV/permanganate, R$_f$=0.22.

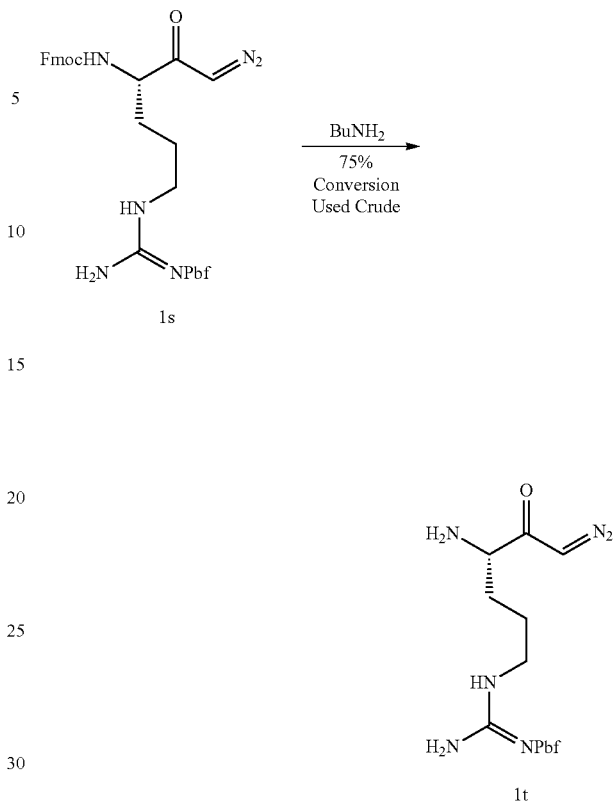

Synthesis of amine 1t Into a flask were added carbamate 1s (323 mg, 0.480 mmol, 1 equiv) and DCM (13 mL, 0.04 M). The mixture was capped with a rubber septum, flushed with argon, and cooled in an ice bath (0° C.). Butylamine (1 mL, 10 mmol, 20 equiv) was added. The mixture was stirred (5 min), transferred into a cold room (−4° C.), stirred (14 h), and diluted with cold toluene (10 mL). Volatiles were removed under reduced pressure (2×toluene azeotrope), and the crude material (approximately 75% conversion) was used directly in the next step. Retention of stereochemistry was shown by coupling crude amine 1t to each enantiomer of Boc-Phe-ONHS; the two diastereomeric products are readily distinguishable by $^{1}$H NMR, and each reaction produced product with a diastereomeric ratio of >20:1. Several other Fmoc deprotection conditions produced significant amounts of epimerization of the Arg stereocenter or decomposition.

Crude amine 1t: $^{1}$H NMR (CD$_3$OD, 500 MHz) δ4.06-4.02 (m, 1H, Arg-α), 3.20-3.14 (m, 2H, Arg-δ), 2.99 (s, 2H, Pbf), 2.56 (s, 3H, Pbf), 2.50 (s, 3H, Pbf), 2.07 (s, 3H, Pbf), 1.76-1.68 (m, 1H, Arg-β/γ), 1.66-1.50 (m, 3H, Arg-β/γ), 1.44 (s, 6H, Pbf); LC/MS elutes at 0.73 min, calculated for [C$_{20}$H$_{30}$N$_6$O$_4$SH]$^{+}$, requires m/z=451.56, found m/z=451.06 (ESI).

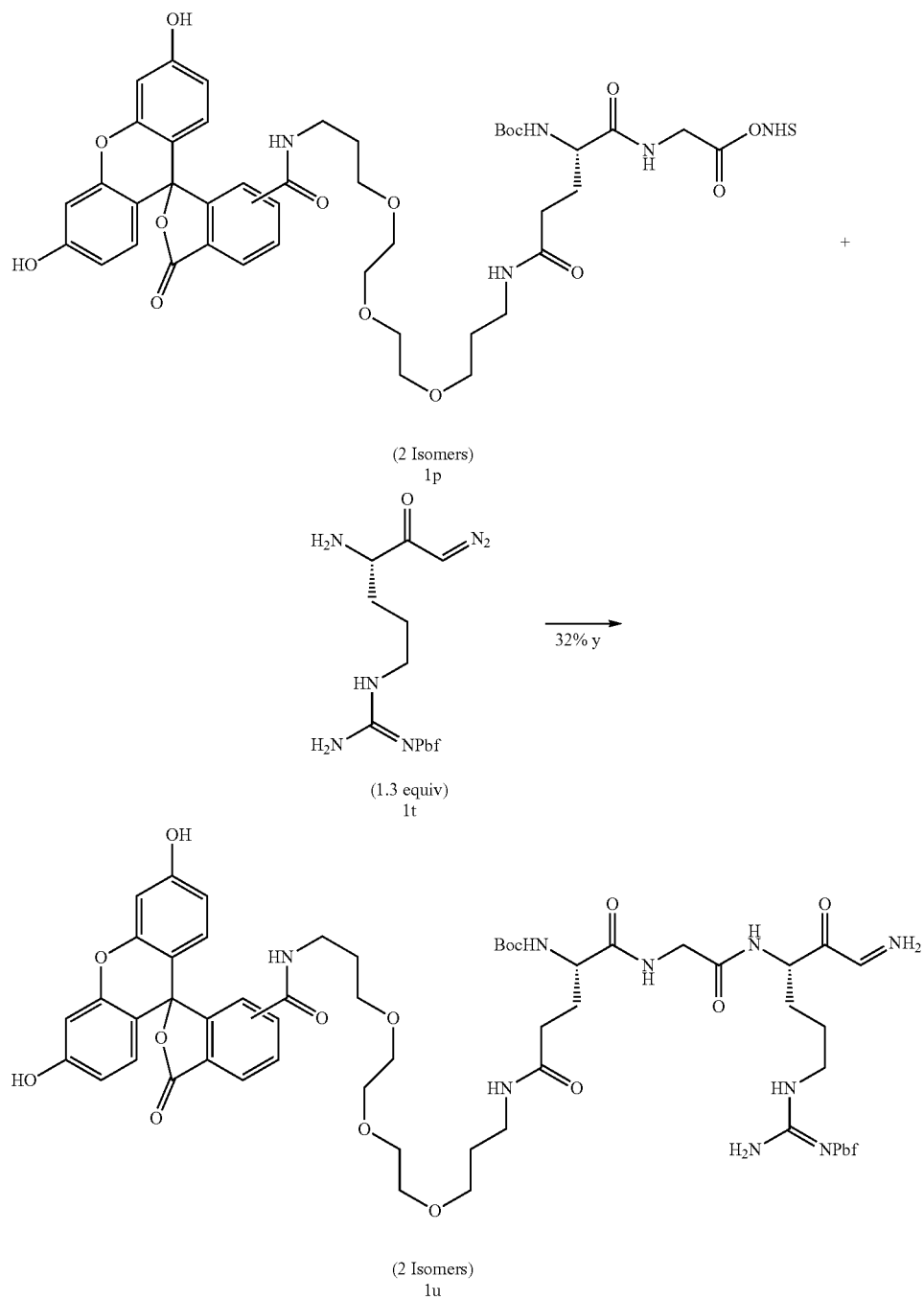

Synthesis of peptide 1u Into a flask were added crude amine 1t (0.48 mmol, 1.3 equiv, approximately 75% pure), THF (5 mL, 0.1 M), crude NHS ester 1p (0.38 mmol, 1 equiv), Hunig's base (125 µL, 0.72 mmol, 1.9 equiv, causing precipitation), and DMF (0.3 mL, redissolving the precipitate). The mixture was stirred in the dark (3 h), quenched with methanol (0.5 mL, 30 min), diluted with DCM (40 mL) and THF (5 mL), washed with sodium bisulfate (0.1 M aqueous, 40 mL), and dried with sodium sulfate. Volatiles were removed under reduced pressure, and the crude material was passed through a silica gel column (50 mL silica gel, 1:1 DCM/acetone+7-16% MeOH). The product streaked through the column and did not elute cleanly. Product-containing fractions (>90% pure, 156 mg, 0.120 mmol, 32% yield, 1:1 mixture of isomers at fluorescein) were collected and used directly for the next step. Diazomethyl ketone 1u is not stable to acidic HPLC conditions (1:1 water/MeCN+ 0.1% TFA causes full decomposition within 15 h). $^1$H NMR signals were assigned by $^1$H-$^1$H COSY and by comparison to signals from the starting materials. $^{13}$C NMR signals were assigned by $^1$H-$^{13}$C HMQC.

$^1$H NMR (CD$_3$OD, 500 MHz, major signals) δ 8.46 (s, 0.5H, fluor), 8.20 (d, J=7.9 Hz, 0.5H, fluor), 8.14 (d, J=8.0 Hz, 0.5H, fluor), 8.07 (d, J=7.9 Hz, 0.5H, fluor), 7.68 (s, 0.5H, fluor), 7.31 (d, J=7.9 Hz, 0.5H, fluor), 6.72-6.64 (m, 4H, phenol), 6.58-6.54 (m, 2H, phenol), 6.00 (s, 1H, CH=N$_2$), 4.38-4.30 (brs, 11H, Arg-α), 4.06-4.00 (m, 1H, Glu-α), 3.91 (s, 2H, Gly-α), 3.66-3.12 (m, 18H, 6×CH$_2$—O, Arg-δ, 2×CH$_2$—NH), 2.97 (s, 2H, Pbf), 2.58 (s, 3H, Pbf), 2.51 (s, 3H, Pbf), 2.31 (d, J=7.4 Hz, 2H, Glu-γ), 2.06 (s, 3H, Pbf), 1.99-1.47 (m, 10H, Glu-β, Arg-β, Arg-γ, 2×C—CH2-C), 1.43 (s, 6H, Pbf), 1.40 (s, 9H, Boc); $^{13}$C NMR (CD$_3$OD, 125 MHz, major signals) δ 196.25, 175.22, 174.73, 174.72, 171.63, 170.70, 168.07, 167.79, 162.77, 159.74, 157.95, 157.90, 154.40, 141.65, 139.26, 137.73, 134.85, 134.29, 133.40, 130.52, 130.33, 126.66, 126.17, 125.96, 125.31, 124.49, 118.35, 114.64, 114.55, 111.41, 111.29, 103.68, 87.61, 80.84, 71.36, 71.17, 71.15, 71.09, 71.04, 70.96, 70.83, 70.14, 70.08, 69.72, 57.76, 55.91, 54.79, 43.88, 43.69, 41.31, 38.98, 38.88, 37.84, 37.80, 33.11, 30.28, 30.24, 30.02, 29.41, 28.74, 28.72, 26.78, 19.64, 18.44, 12.57; IR (film, cm$^{-1}$) 3342, 2972, 2928, 2874, 2442, 1642, 1610, 1450, 1428, 1109, 1084, 974; HRMS calculated for [C$_{63}$H$_{80}$N$_{10}$O$_{18}$SH]$^+$, requires m/z=1297.5446, found m/z=1297.5412 (ESI); TLC (1:1) DCM/acetone+10% MeOH, UV/permanganate, R$_f$=0.38 (streaks); LC/MS elutes at 1.46 min, calculated for [C$_{63}$H$_{80}$N$_{10}$O$_{18}$SH]$^+$, requires m/z=1297.54, found m/z=1297.16 (ESI).

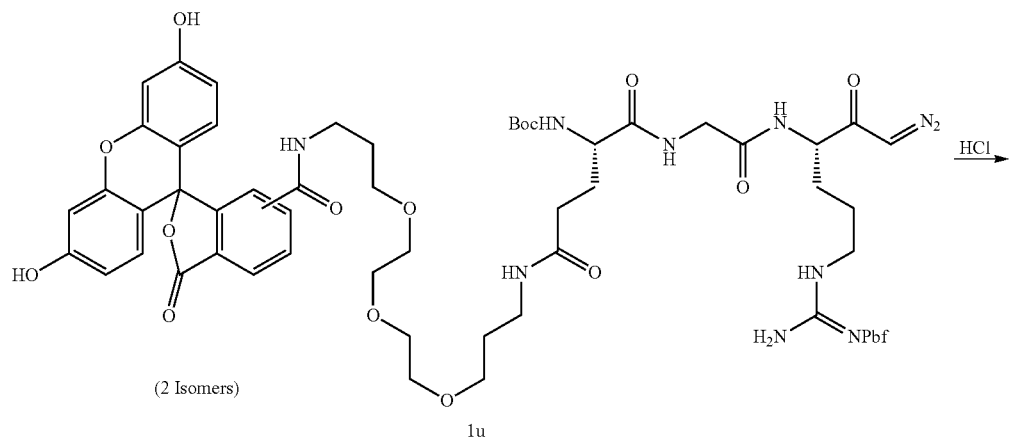

(2 Isomers)

1u

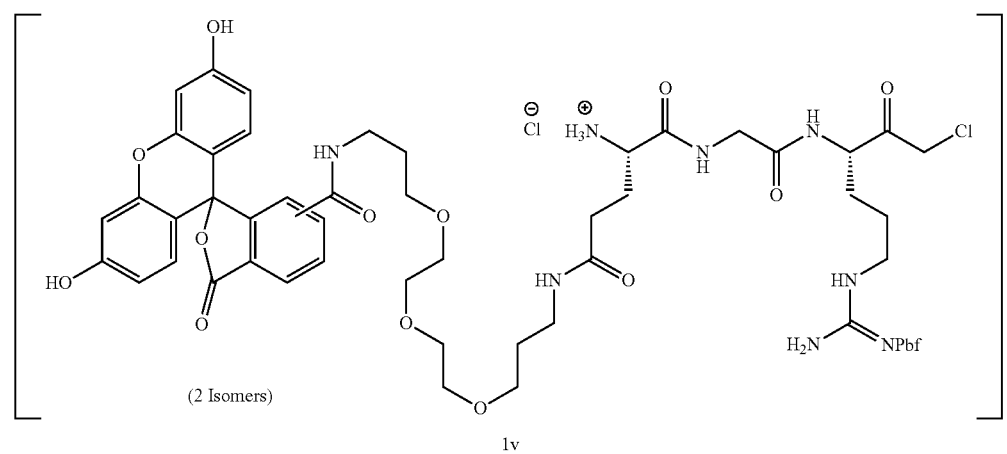

(2 Isomers)

1v

Synthesis of chloromethyl ketone 1v Into a flask were added mostly pure diazomethyl ketone 1u (0.120 mmol, 1 equiv) and THF (3 mL, 0.04 M, producing a nearly homogeneous solution). The flask was capped with a rubber septum and vented with a needle, and hydrochloric acid (4.0 M in dioxane, 3 mL, 0.04 M in substrate) was added by syringe (producing a clumpy goo). The mixture was stirred (1 h) in the dark and diluted with toluene (4 mL). Volatiles were removed under reduced pressure (3×toluene azeotrope). Analysis by LC/MS showed chloromethyl ketone 1v as the major product, and the crude mixture was used directly for the next step.

LC/MS elutes at 1.14 min, calculated for [C$_{58}$H$_{73}$C$_1$N$_8$O$_{16}$SH]$^+$, requires m/z=1205.46, found m/z=1205.34 (ESI).

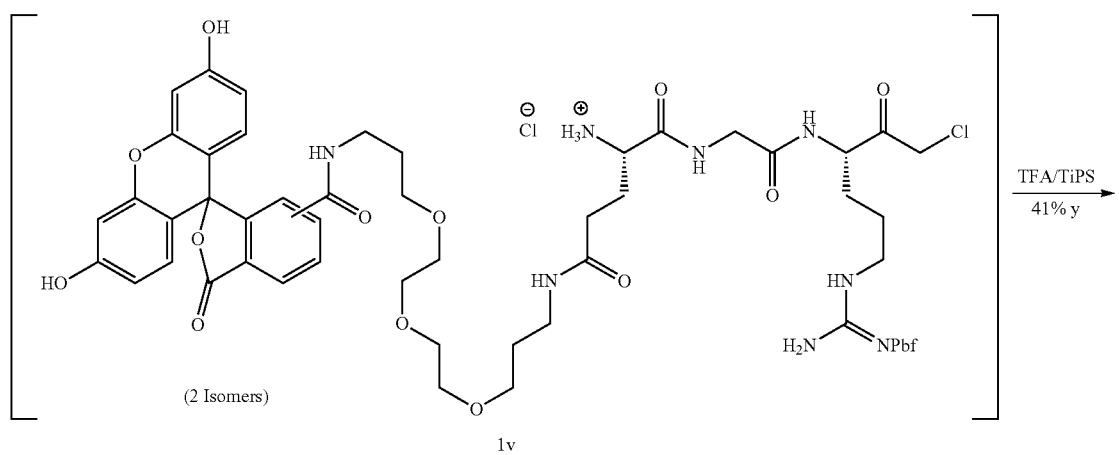

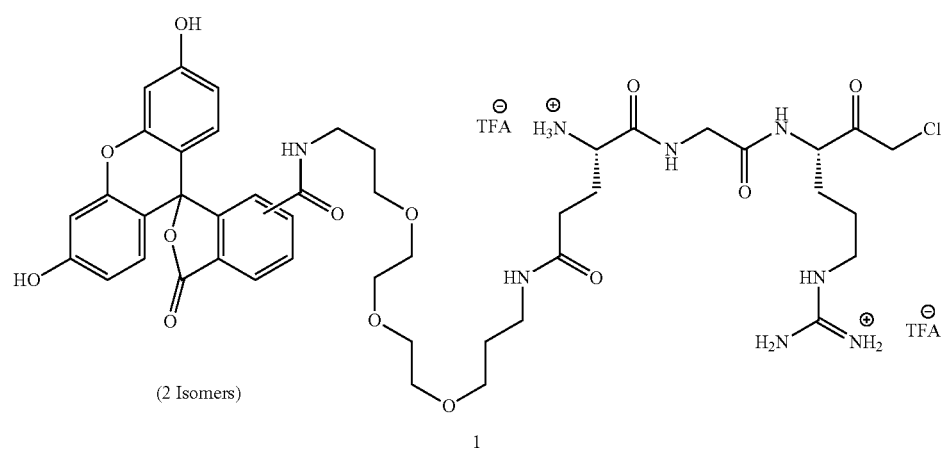

Synthesis of guanidinium 1 Into a flask were added crude peptide 1v (0.120 mmol, 1 equiv), and a mixture of TFA, TiPS, and water (38:1:1, 2 mL, 0.06 M, producing a homogeneous solution). The mixture was stirred in the dark (1.5 h) and diluted with toluene (3 mL). Volatiles were removed under reduced pressure (2×toluene azeotrope). The crude mixture was dissolved in water (2 mL) and washed with EtOAc (2×2 mL). The aqueous phase was purified by semi-preparative RP-HPLC ($C_{18}$ column, water+0.1% TFA with 15-35% MeCN over 30 min, product isomers elute at 14.5 and 15.4 min) to yield pure guanidinium 1 (58 mg, 0.049 mmol, 41% yield) as a mixture (approximately 1:1) of regioisomers at fluorescein and as a yellow solid. The regioisomeric ratio was measured by $^1$H NMR. $^1$H NMR signals were assigned by $^1$H-$^1$H COSY. Material was stored at −20° C. as a stock solution in water, and is stable for at least several months.

$^1$H NMR ($D_2O$, 500 MHz) δ 8.47 (d, J=4.9 Hz, 0.5H, fluor), 8.19-8.15 (m, 0.5H, fluor), 8.06-7.98 (m, 1H, fluor), 7.47 (s, 0.5H, fluor), 7.22 (t, J=7.5 Hz, 0.5H, fluor), 7.03-6.67 (m, 6H, 2×phenol), 4.55-4.43 (m, 3H, Arg-α, $CH_2$—Cl), 4.10-3.93 (m, 3H, Glu-α, Gly-α), 3.62-3.08 (m, 18H, 6×$CH_2$—O, Arg-δ, 2×$CH_2$—NHCO), 2.43-2.32 (m, 2H, Glu-γ), 2.17-2.10 (m, 2H, Glu-β), 1.92-1.44 (m, 8H, Arg-β, Arg-γ, 2×C—$CH_2$—C); $^{13}$C NMR ($D_2O$+1.5% MeOH, 125 MHz) 3203.95, 174.27, 171.40, 170.35, 168.79, 168.48, 167.50, 166.82, 163.3 (q, J=35.5 Hz), 157.32, 156.94, 141.92, 140.51, 139.19, 136.76, 132.89, 131.91, 131.69, 130.32, 130.04, 129.87, 129.31, 128.92, 127.16, 118.50, 116.9 (q, J=291.7 Hz), 114.81, 114.72, 114.37, 103.17, 70.21, 70.05, 69.91, 69.87, 69.39, 69.21, 68.94, 57.44, 53.15, 47.30, 42.73, 41.06, 38.19, 37.10, 37.36, 28.82, 27.30, 27.23, 24.93; IR (film, cm$^{-1}$) 3285, 1671, 1638, 1201, 1180, 1127; HRMS calculated for $[C_{45}H_{57}ClN_8O_{13}H]^+$, requires m/z=953.3806, found m/z=953.3774 (ESI); RP-HPLC $C_{18}$ column, 15-35% MeCN in water+0.1% TFA, flow=1.0 mL/min, monitored at 214 nm, isomers elute overlapping at 14.6 and 15.4 min.

Scheme S2

Scheme S2, FIG. 6, shows the synthetic strategy used to access compound 2.

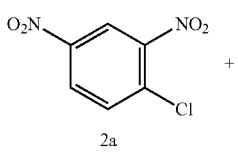

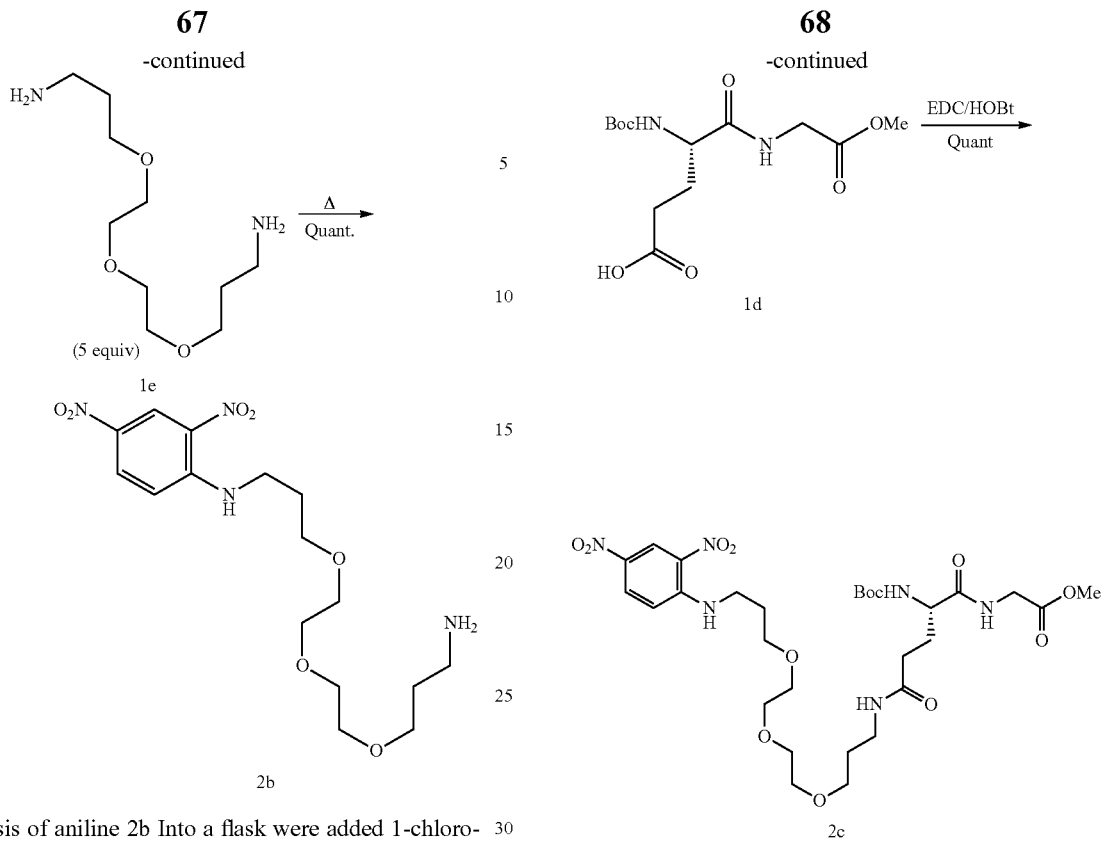

Synthesis of aniline 2b Into a flask were added 1-chloro-2,4-dinitrobenzene (2, 4.05 g, 20.0 mmol, 1 equiv), 4,7,10-trioxa-1,13-tridecanediame (1e, 22.0 mL, 100 mmol, 5 equiv), and ethanol (100 mL, 0.2 M). The mixture was heated to reflux (2 h, changing from yellow to red), concentrated under reduced pressure, diluted with water (100 mL), brine (100 mL), and sodium bicarbonate (saturated aqueous, 50 mL), extracted with DCM (150+50 mL), washed with sodium chloride (50% saturated, 2×100 mL), and dried with sodium sulfate. Volatiles were removed under reduced pressure to yield mostly pure aniline 2b, which was used directly in the next step.

$^1$H NMR (CDCl$_3$, 500 MHz) δ9.14 (s, 1H, Ar), 8.92 (s, 1H, Ar—NH), 8.27 (d, J=11.6 Hz, 1H, Ar), 6.97 (d, J=10.5 Hz, 1H, Ar), 3.78-3.51 (m, 14H, 6×CH$_2$—O, CH$_2$—NHAr), 2.78 (t, J=8.3 Hz, 2H, CH$_2$—NH$_2$), 2.08-2.00 (m, 2H, C—CH$_2$C), 1.68-1.76 (m, 2H, C—CH$_2$C), 1.42-1.00 (brs, 2H, NH$_2$); LC/MS elutes at 0.61 min, calculated for [C$_{16}$H$_{26}$N$_4$O$_7$H]$^+$, requires m/z=387.19, found m/z=387.13 (ESI).

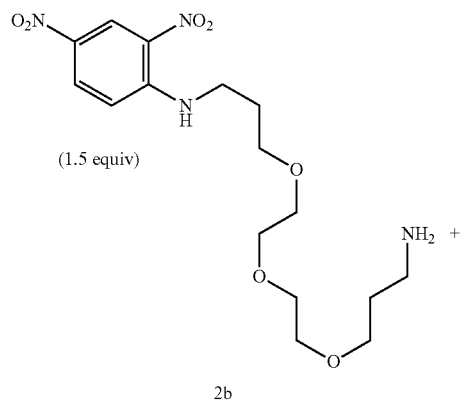

(1.5 equiv)

2b

Synthesis of amide 2c Into a flask were added crude acid 1d (1.57 g, 4.93 mmol, 1 equiv), crude amine 2b (2.85 g, 7.39 mmol, 1.5 equiv), EDC hydrochloride (1.14 g, 5.92 mmol, 1.2 equiv), HOBt hydrate (904 mg, 5.91 mmol, 1.2 equiv), and DCM (49 mL, 0.1 M). The mixture was stirred (15 h), diluted with DCM (50 mL), washed with a mixture (1:1:1, 60 mL) of water, brine, and sodium bicarbonate (saturated aqueous) and with a mixture (1:1:1, 60 mL) of citric acid (10% aqueous), water, and brine, and dried with sodium sulfate. Volatiles were removed under reduced pressure, and the crude material was purified by column chromatography (120 mL silica gel, [4:1 to 1:1] DCM/acetone) to yield amide 2c (3.39 g, quantitative). $^1$H NMR signals were assigned by $^1$H-$^1$H COSY and by comparison to signals from the starting materials.

$^1$H NMR (CDCl$_3$, 400 MHz) δ9.13 (d, J=2.7 Hz, 1H, Ar), 8.92 (t, J=4.7 Hz, 1H, NH—Ar), 8.26 (dd, J$_1$=5.6 Hz, J$_2$=2.7 Hz, 1H, Ar), 7.50-7.40 (brs, 1H, Gly-NH), 6.97 (d, J=9.6 Hz, 1H, Ar), 6.56 (t, J=6.2 Hz, 1H, NH-Glu-γ), 5.82 (d, J=6.9 Hz, 1H, NH-Boc), 4.20 (q, J=6.9 Hz, 1H, Glu-α), 4.10 (dd, J$_1$=18.0 Hz, J$_2$=6.0 Hz, 1H, Gly-α), 3.98 (dd, J$_1$=18.3 Hz, J$_2$=5.2 Hz, 1H, Gly-α), 3.72 (s, 3H, OMe), 3.71-3.52 (m, 14H, 6×CH$_2$—O, CH$_2$—NHAr), 3.35 (q, J=6.0 Hz, 2H, CH$_2$—NH), 2.42-2.32 (m, 2H, Glu-γ), 2.07-1.98 (m, 4H, Glu-β, C—CH$_2$—C), 1.81-1.73 (m, 2H, C—CH$_2$—C), 1.42 (s, 9H, Boc); $^{13}$C NMR (CDCl$_3$, 125 MHz) (172.61, 172.15, 170.12, 155.64, 148.30, 135.38, 130.14, 130.10, 124.12, 113.85, 79.64, 70.48, 70.34, 70.26, 69.92, 69.73, 69.09, 53.64, 52.10, 41.82, 40.92, 37.83, 32.33, 28.88, 28.75, 28.48, 28.17; IR (film, cm$^{-1}$) 3326, 2929, 2872, 1659, 1618, 1523, 1336; HRMS calculated for [C$_{29}$H$_{45}$N$_6$O$_{13}$H]$^+$, requires m/z=687.3196, found m/z=687.3195 (ESI); TLC (3:2) DCM/acetone, yellow, R$_f$=0.38.

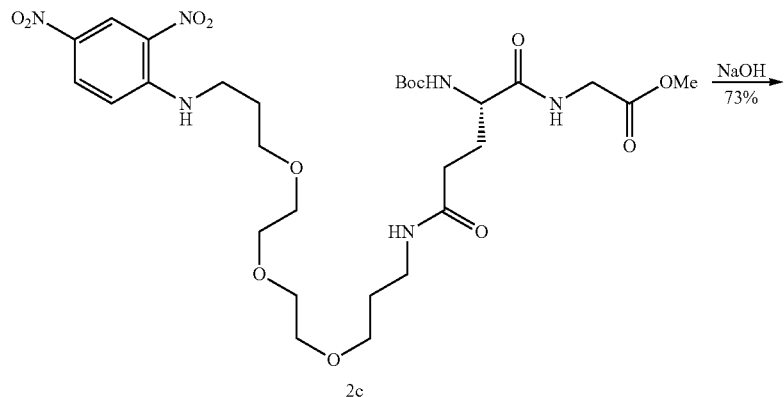

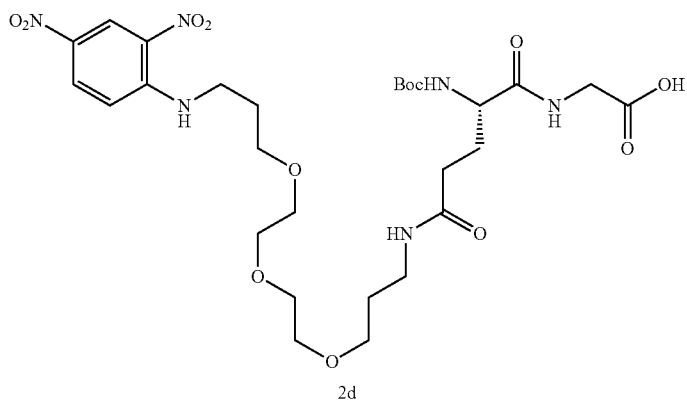

Synthesis of acid 2d Into a flask were added ester 2c (641 mg, 0.934 mmol, 1 equiv), dioxane (9 mL, 0.1 M), water (3.4 mL), and sodium hydroxide (1 M, 5.6 mL, 5.6 mmol, 6 equiv). The mixture was stirred (2 h), cooled in an ice bath (0° C.), neutralized with sodium bisulfate (2 M, approximately 3 mL, until the mixture became dark brown, approximately pH 6) and sodium bicarbonate (saturated aqueous, 0.5 mL, to pH 7, becoming red). Volatiles were removed by lyophilization. The crude mixture was mixed with DCM (25 mL), insolubles were removed by vacuum filtration, and the red filtrate was collected. Volatiles were removed under reduced pressure to yield nearly pure amide 2d (459 mg, 0.683 mmol, 73% yield from Boc-Glu(Bn)-OH), which was used directly for the next step.

$^1$H NMR (CD$_3$OD, 400 MHz) δ9.03 (d, J=1.8 Hz, 1H, Ar), 8.29 (dd, J$_1$=10.2 Hz, J$_2$=1.7 Hz, 1H, Ar), 7.20 (d, J=10.4 Hz, 1H, Ar), 4.05 (t, J=7.8 Hz, 1H, Glu-α), 3.77 (d, J=18.3 Hz, 1H, Gly-α), 3.71 (d, J=16.6 Hz, 1H, Gly-α), 3.68-3.54 (m, 12H, 6×CH2-O), 3.41 (t, J=6.2 Hz, 2H, CH$_2$—NHAr), 3.22 (t, J=7.7 Hz, 2H, CH$_2$—NH), 2.26 (t, J=7.7 Hz, 2H, Glu-γ), 2.10-1.84 (m, 4H, Glu-β, C—CH$_2$—C), 1.73 (quint, J=6.5 Hz, 2H, C—CH$_2$C), 1.43 (s, 9H, Boc); LC/MS elutes at 1.22 min, calculated for [C$_{28}$H$_{44}$N$_6$O$_{13}$H]$^+$, requires m/z=673.30, found m/z=673.28 (ESI).

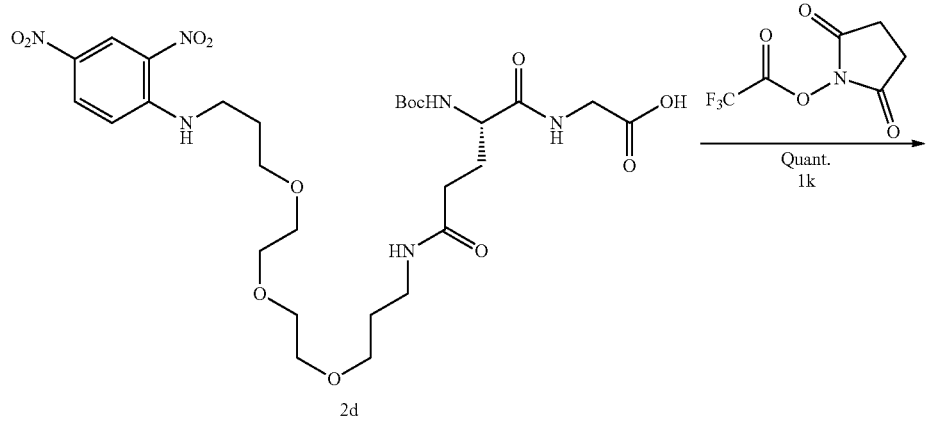

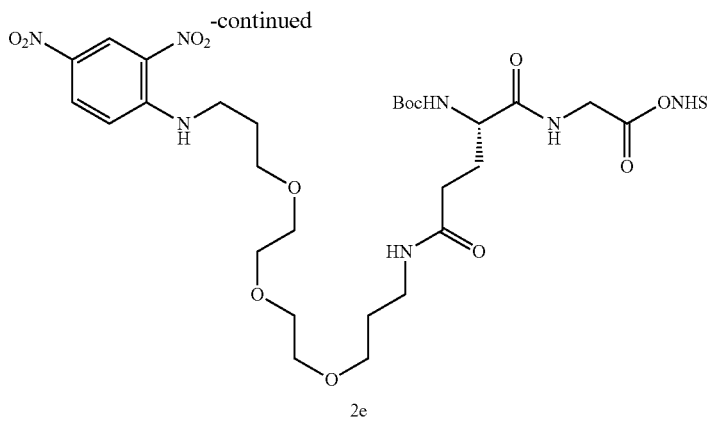

2e

Synthesis of ester 2e Into a dried flask flushed with argon were added crude acid 2d (1.82 mmol, 1 equiv), THF (18 mL, 0.1 M), pyridine (622 μL, 8.19 mmol, 4.5 equiv), and trifluoroacetate 1k (1.54 g, 7.28 mmol, 4 equiv). The mixture was maintained under an argon atmosphere, stirred in the dark (3 h), quenched with water (5 mL, 5 min), and diluted with additional water (35 mL) and DCM (40 mL). The organic phase was isolated and the aqueous phase was further extracted with a mixture (2:1, 20 mL) of DCM and THF. The combined organic phases were washed with a mixture (1:1, 40 mL) of citric acid (10% aqueous) and brine and dried with sodium sulfate. Volatiles were removed under reduced pressure to yield mostly pure ester 2e (quantitative), which was used directly for the next step. Ester 2e decomposes on silica gel.

$^1$H NMR (CDCl$_3$, 500 MHz) δ9.12 (d, J=2.6 Hz, 1H, Ar), 8.90 (t, J=5.2 Hz, 1H, NH—Ar), 8.25 (dd, J$_1$=9.6 Hz, J$_2$=2.6 Hz, 1H, Ar), 7.73-7.67 (brs, 1H, Gly-NH), 6.96 (d, J=9.7 Hz, 1H, Ar), 6.88-6.81 (brs, 1H, NH), 5.85 (d, J=6.4 Hz, 1H, Boc-NH), 4.47 (dd, J$_1$=18.2 Hz, J$_2$=6.4 Hz, 1H, Gly-α), 4.32-4.20 (m, 2H, Gly-α, Glu-α), 3.74-3.51 (m, 14H, 6×CH$_2$—O, CH$_2$—NHAr), 3.34 (q, J=6.3 Hz, 2H, CH$_2$—NH), 2.82 (s, 4H, NHS), 2.34 (t, J=6.6 Hz, 2H, Glu-γ), 2.09-1.88 (m, 4H, Glu-β, C—CH$_2$—C), 1.76 (quint, J=6.1 Hz, 2H, C—CH$_2$C), 1.41 (s, 9H, Boc); LC/MS elutes at 1.37 min, calculated for [C$_{32}$H$_{47}$N$_7$O$_{15}$H]$^+$, requires m/z=770.32, found m/z=770.34 (ESI).

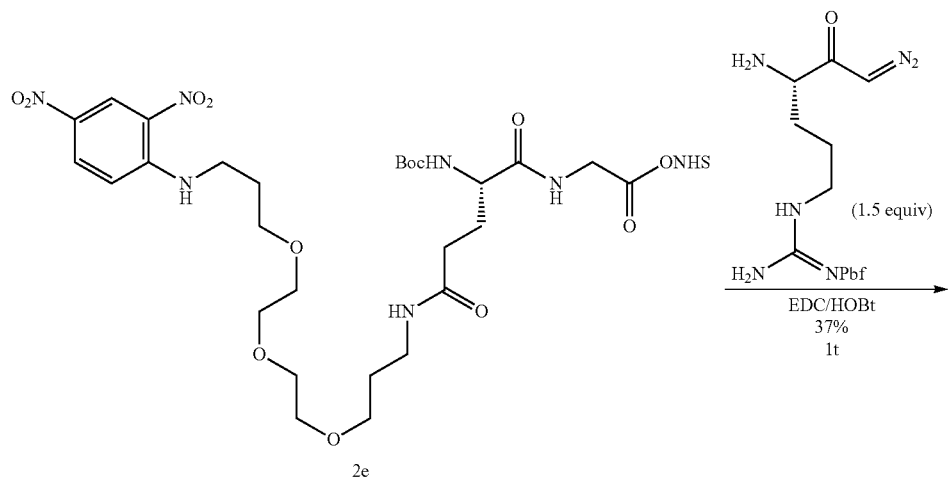

2e

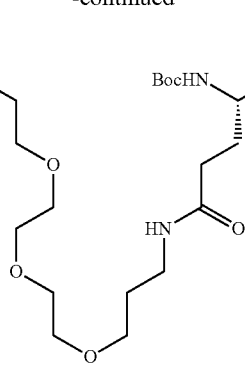

2f

Synthesis of peptide 2f Into a flask were added crude amine 1t (0.48 mmol, 1.2 equiv, approximately 75% pure), THF (5 mL, 0.1 M), crude NHS ester 2e (0.42 mmol, 1 equiv), and Hünig's base (125 μL, 0.72 mmol, 1.7 equiv). The mixture was stirred (3 h), diluted with DCM (40 mL), washed with citric acid (5% aqueous, 40 mL), and dried with sodium sulfate. Volatiles were removed under reduced pressure, and the crude material was purified by column chromatography (50 mL silica gel, 1:1 DCM/acetone+1-5% MeOH) to yield amide 2f (166 mg, 0.150 mmol, 36% yield from methylester 1d) plus additional slightly impure material (107 mg). $^1$H NMR signals were assigned by $^1$H-$^1$H COSY and by comparison to signals from the starting materials.

$^1$H NMR (CDCl$_3$, 400 MHz) δ9.11 (d, J=2.7 Hz, 1H, Ar), 8.93 (t, J=4.9 Hz, 1H, NH—Ar), 8.25 (dd, J$_1$=9.5 Hz, J$_2$=2.8 Hz, 1H, Ar), 7.76 (t, J=6.1 Hz, 1H, Gly-NH), 7.54 (d, J=8.5 Hz, 1H, Arg-NH), 6.98 (d, J=9.6 Hz, 1H, Ar), 6.86 (t, J=5.2 Hz, 1H, Glu-γ-NH), 6.40-6.32 (brs, 2H, 2×Guan-NH), 6.23-6.10 (brs, 2H, Guan-NH, Boc-NH), 5.79-5.71 (brs, 1H, CH=N$_2$), 4.46-4.38 (brs, 1H, Arg-α), 4.13 (q, J=6.4 Hz, 1H, Glu-α), 4.05 (dd, J$_1$=17.0 Hz, J$_2$=5.9 Hz, 1H, Gly-α), 3.90 (dd, J$_1$=16.7 Hz, J$_2$=5.6 Hz, 1H, Gly-α), 3.72-3.50 (m, 14H, 6×CH$_2$—O, CH$_2$—NHAr), 3.30 (q, J=6.2 Hz, 2H, CH$_2$—NH), 3.19 (q, J=5.9 Hz, 2H, Arg-δ), 2.94 (s, 2H, Pbf), 2.56 (s, 3H, Pbf), 2.50 (s, 3H, Pbf), 2.34 (t, J=6.9 Hz, 2H, Glu-γ), 2.08 (s, 3H, Pbf), 2.08-1.99 (m, 4H, Glu-β, C—CH$_2$—C), 1.94-1.82 (m, 1H, Arg-D), 1.75 (quint, J=6.2 Hz, 2H, C—CH$_2$C), 1.70-1.60 (m, 1H, Arg-β), 1.59-1.50 (m, 2H, Arg-γ), 1.45 (s, 6H, Pbf), 1.39 (s, 9H, Boc); $^{13}$C NMR (CDCl$_3$, 125 MHz) δ194.01, 173.25, 172.67, 169.60, 158.50, 156.26, 156.08, 148.29, 137.99, 135.45, 132.80, 131.95, 130.13, 129.97, 124.47, 124.04, 117.28, 113.95, 86.25, 79.92, 70.40, 70.26, 70.18, 69.84, 69.37, 69.14, 56.41, 54.71, 53.92, 43.03, 41.87, 40.33, 37.60, 32.26, 28.79, 28.53, 28.42, 28.40, 28.15, 27.98, 25.29, 19.13, 17.80, 12.30; IR (film, cm$^{-1}$) 3334, 2974, 2925, 2868, 1618, 1544, 1520, 1336, 1099, 903; HRMS calculated for [C$_{48}$H$_{72}$N$_{12}$O$_{16}$SH]$^+$, requires m/z=1105.4983, found m/z=1105.4956 (ESI); TLC (1:1) DCM/acetone+4% MeOH, permanganate, R$_f$=0.23.

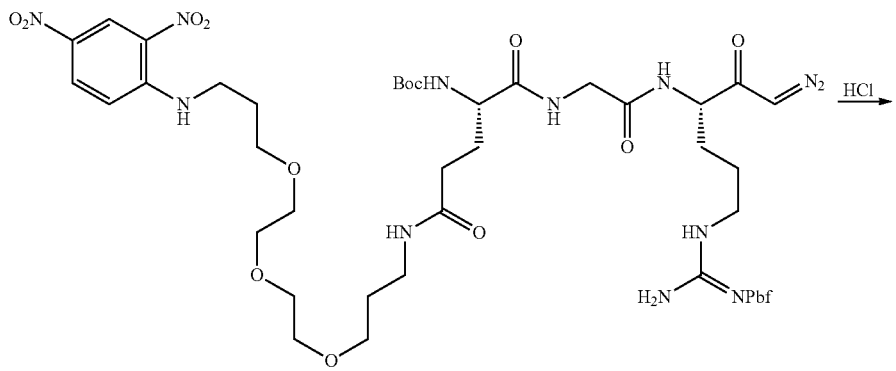

2f

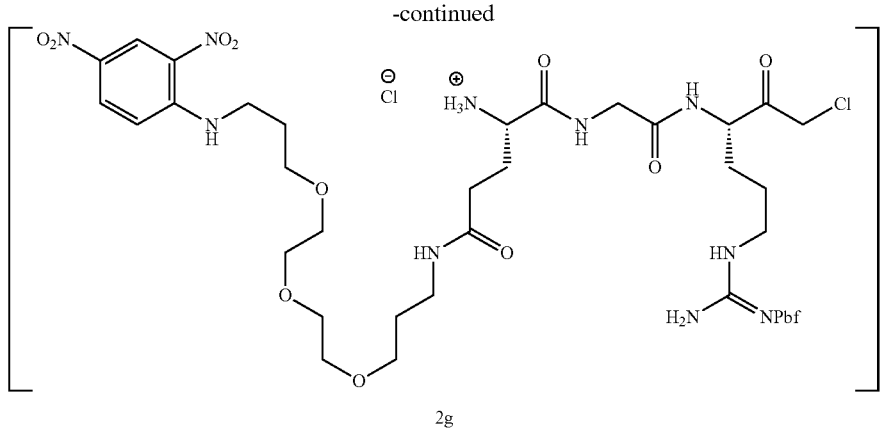

2g

Synthesis of chloromethyl ketone 2g Into a flask were added diazomethyl ketone 2f (166 mg, 0.150 mmol, 1 equiv) and THF (3 mL, 0.05 M). The flask was capped with a rubber septum and vented with a needle, and hydrochloric acid (4.0 M in dioxane, 3 mL, 0.05 M in substrate) was added by syringe. The mixture was stirred (1.5 h) and diluted with toluene (4 mL). Volatiles were removed under reduced pressure (3×toluene azeotrope). Analysis by LC/MS showed chloromethyl ketone 2g as the major product, and the crude mixture was used directly for the next step.

LC/MS elutes at 1.36 min, calculated for $[C_{43}H_{65}ClN_{10}O_{14}SH]^+$, requires m/z=1013.42, found m/z=1013.23 (ESI).

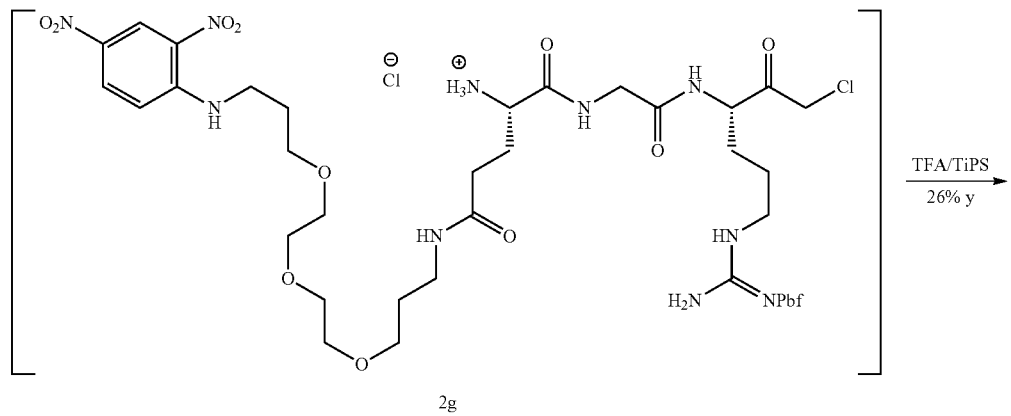

2g $\xrightarrow{\text{TFA/TiPS}}$ 26% y

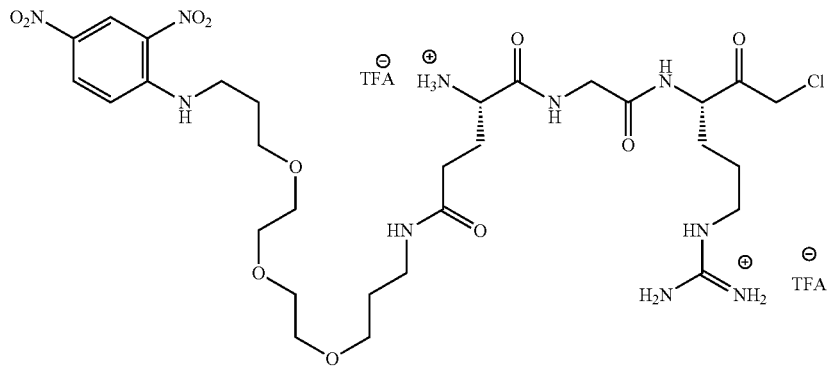

2

Synthesis of guanidinium 2 Into a flask were added crude peptide 2g (0.150 mmol, 1 equiv), and a mixture of TFA, TiPS, and water (38:1:1, 2 mL, 0.07 M). The mixture was stirred (1.5 h) and diluted with toluene (3 mL). Volatiles were removed under reduced pressure (2×toluene azeotrope). The crude mixture was dissolved in water (2 mL) and washed with EtOAc (2×2 mL). The aqueous phase was purified by semi-preparative RP-HPLC ($C_{18}$ column, water+0.1% TFA with 15-35% acetonitrile over 30 min, product elutes at 19.3 min) to yield pure guanidine 2 (38 mg, 0.038 mmol, 26% yield) as a yellow solid. $^1$H NMR signals were assigned by $^1$H-$^1$H COSY. Material was stored at −20° C. as a stock solution in water, and is stable for at least several months.

$^1$H NMR ($D_2O$, 500 MHz) δ 8.73 (dd, $J_1$=15.7 Hz, $J_2$=3.6 Hz, 1H, Ar), 8.09 (dd, $J_1$=9.0 Hz, $J_2$=2.7 Hz, 1H, Ar), 7.00 (dd, $J_1$=9.8 Hz, $J_2$=6.3 Hz, 1H, Ar), 4.48 (dd, $J_1$=9.0 Hz, $J_2$=4.3 Hz, 1H, Arg-α), 4.55 (d, J=17.2 Hz, 1H, $CH_2$—Cl), 4.51 (d, J=17.1 Hz, 1H, CH2-Cl), 4.11-3.95 (m, 3H, Glu-α, Gly-α), 3.68-3.14 (m, 18H, 6×$CH_2$—O, Arg-8, 2×$CH_2$—NH), 2.42-2.36 (m, 2H, Glu-γ), 2.18-2.12 (m, 2H, Glu-β), 1.98-1.91 (m, 3H, Arg-β, Arg-γ, C—$CH_2$—C), 1.74-1.54 (m, 5H, Arg-β, Arg-γ, C—$CH_2$—C); $^{13}$C NMR ($D_2O$+1.5% MeOH, 125 MHz) 3204.06, 174.29, 171.41, 170.36, 163.2 (q, J=35.4 Hz), 157.36, 149.23, 135.36, 130.80, 129.88, 124.71, 116.7 (q, J=291.7 Hz), 115.39, 57.46, 53.16, 47.83, 42.76, 41.69, 41.09, 37.15, 31.36, 28.88, 28.43, 27.32, 27.28, 24.96; IR (film, $cm^{-1}$) 3359, 1662, 1618, 1331, 1172, 1127; HRMS calculated for $[C_{30}H_{49}ClN_{10}O_{11}H]^+$, requires m/z=761.3344, found m/z=761.3324 (ESI); RP-HPLC $C_{18}$ column, 15-35% MeCN in water+0.1% TFA, flow=1.0 mL/min, monitored at 214 nm, elutes at 19.3 min.

Scheme S3

Figure 8:
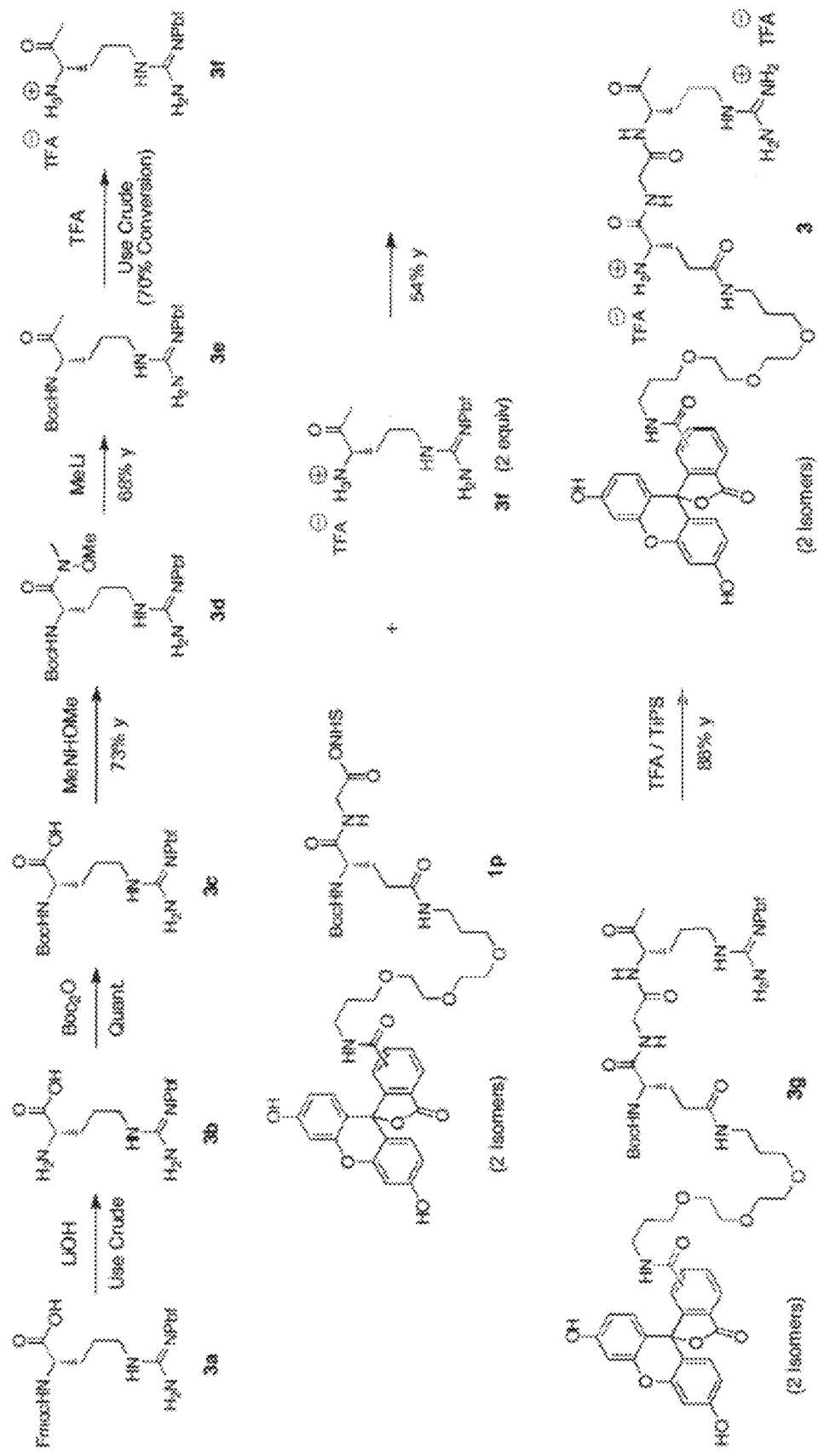
FIG. 8 shows a chemical scheme (Scheme III) for the synthesis of compound 3, which is a version of compound 2 which contains an unreactive methyl ketone group, rather than a chloromethyl ketone group.
Figure 9:
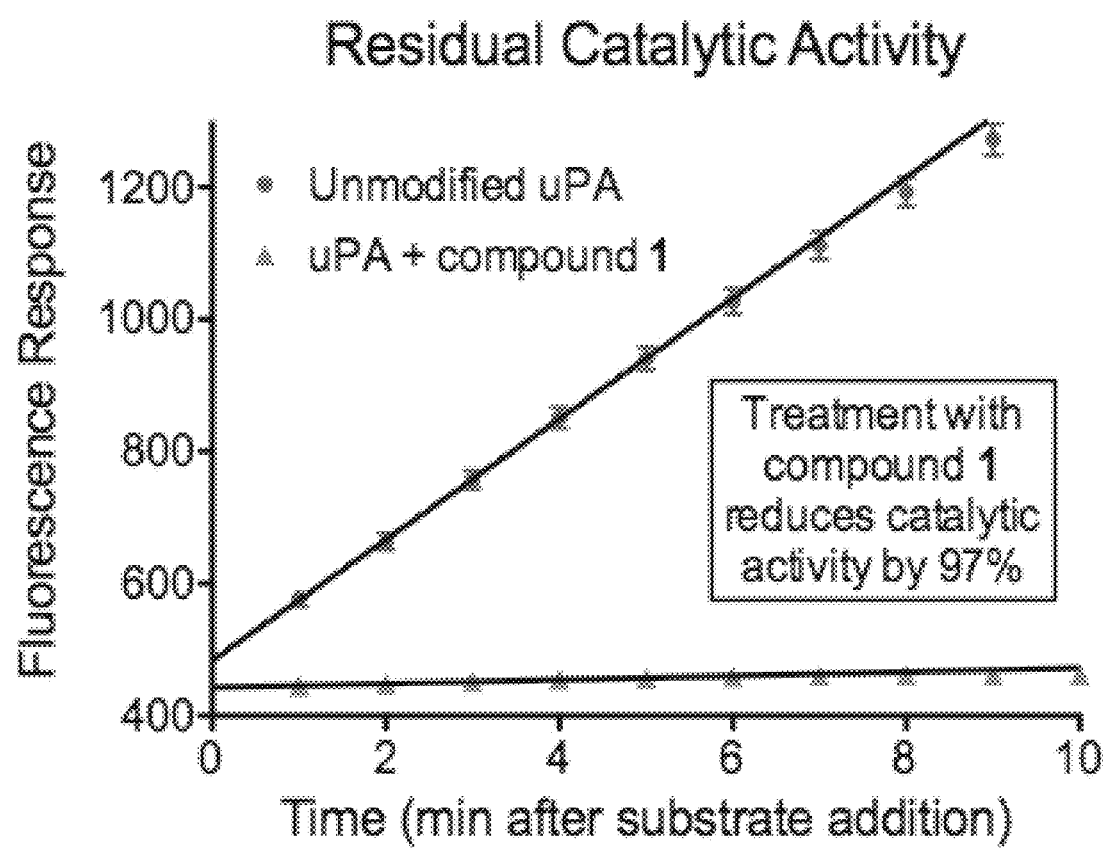
FIG. 9 shows the residual catalytic activity of uPA with or without compound 1 treatment was measured by the increase of fluorescence over time corresponding to enzyme-mediated hydrolysis of Cbz-Gly-Gly-Arg-AMC. Fluorescence Response is measured with 330 nm absorbance and 460 nm emission in an automatic plate reader. Error bars represent the standard deviation of triplicate experiments.
Figure 10:
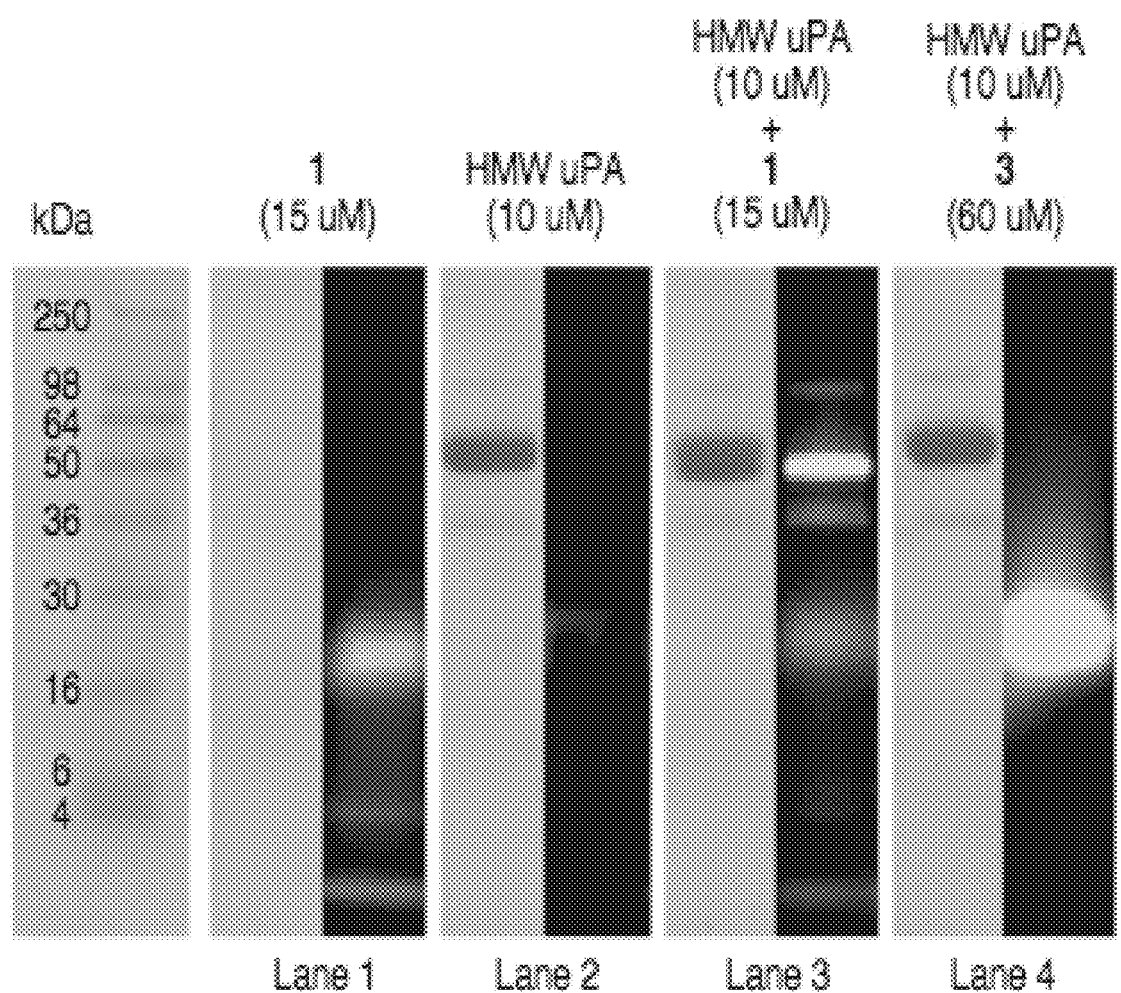
FIG. 10 shows coomassie (purple on white, left) and 488-to-532 nm fluorescence (green on black, right) analysis of uPA bound by compound 1
Figure 11:
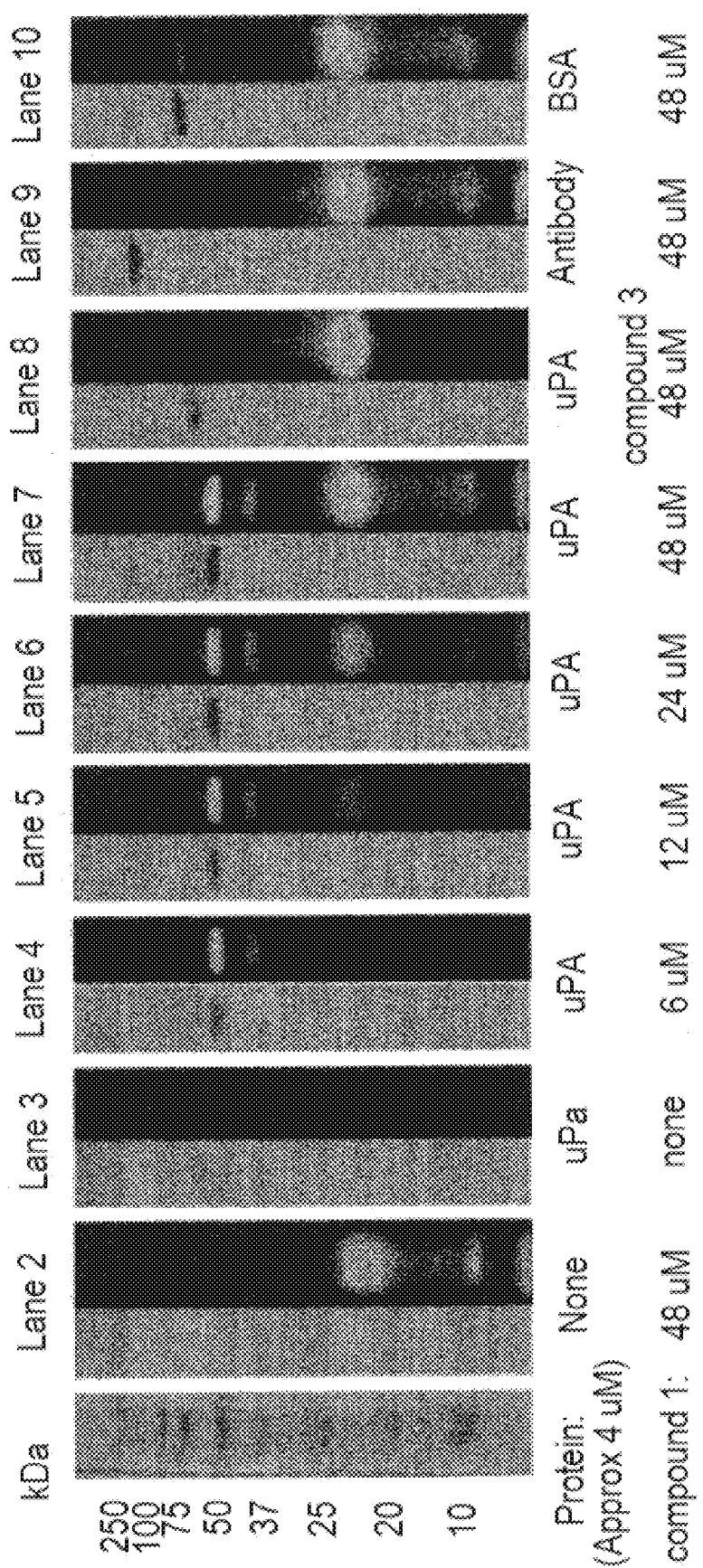
FIG. 11 shows Coomassie (purple on white, left) and 488-to-532 nm fluorescence (green on black, right) analysis of various proteins bound by various concentrations to compound 1.
Figure 12:
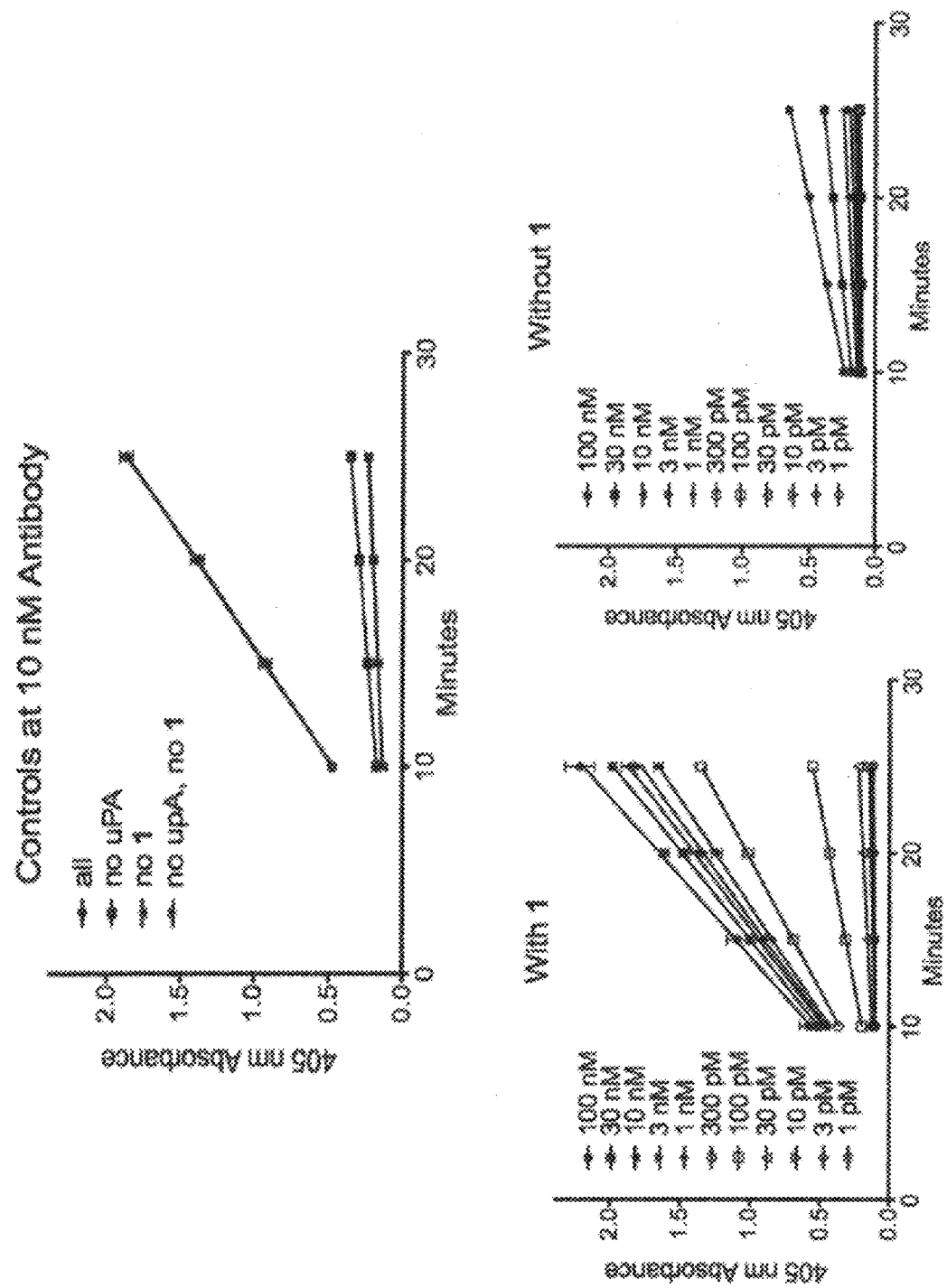
FIG. 12 shows crude data from ELISA analysis of compound 1. Concentrations refer to anti-fluorescein antibody. Error bars represent standard deviations of triplicate experiments. Lines of best fit were calculated (Prism software) by linear regression.
Figure 13:
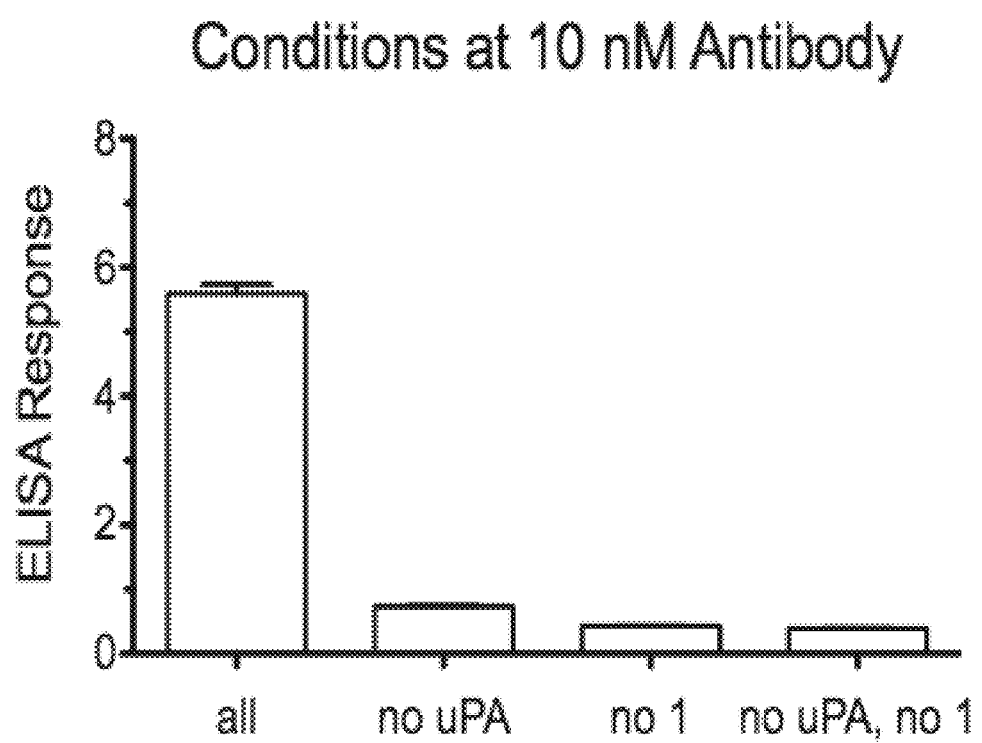
FIG. 13 shows the control conditions for ELISA analysis.
Figure 14:
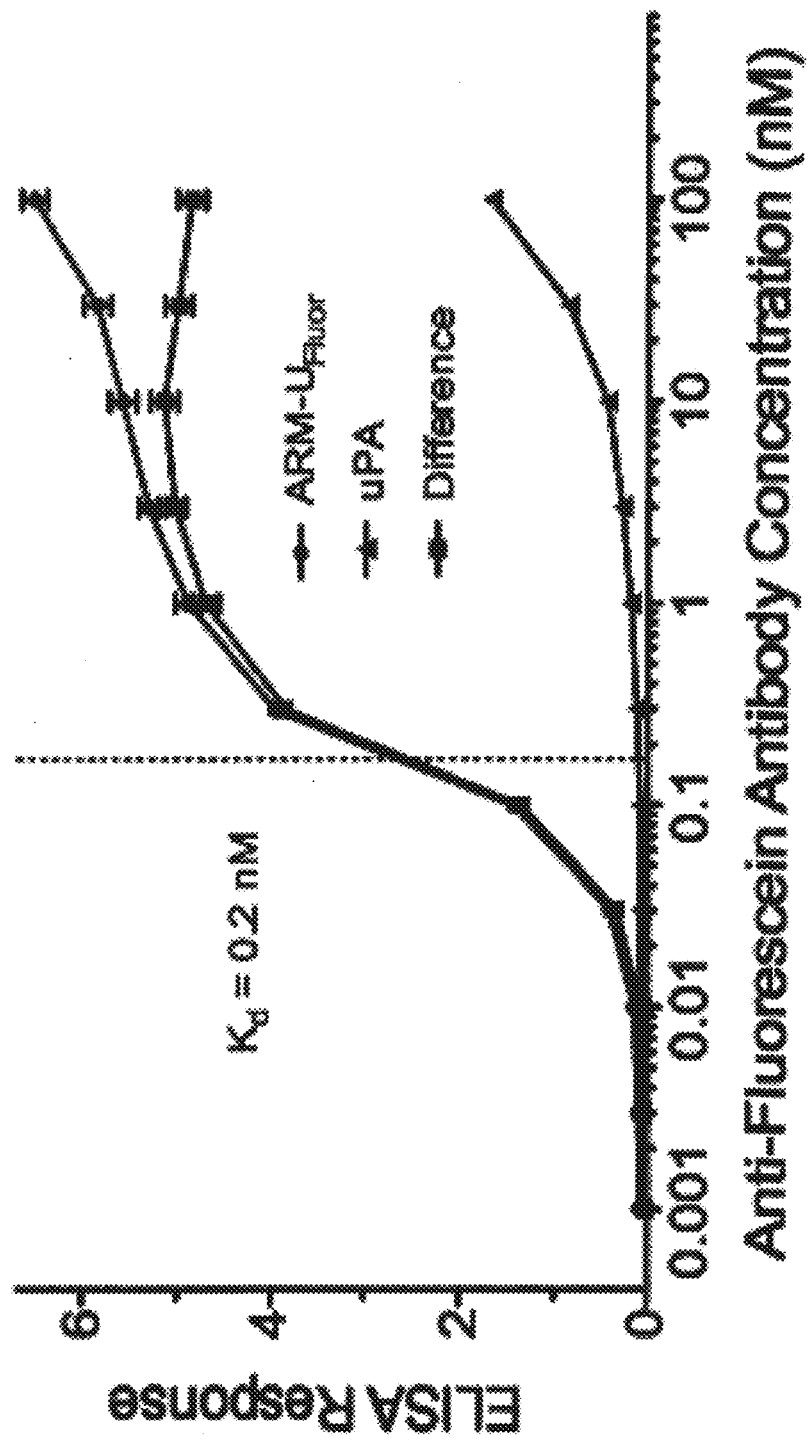
FIG. 14 shows the concentration dependence of the binding between ARM-U$_{Fluor}$ and anti-fluorescein antibody. The ELISA response (rate of change of 405 nm absorbance units per hour) is the slope calculated from linear regression analysis of the absorbance measured over four time points. Error bars represent standard deviations of triplicate experiments. The K$_d$ value was approximated graphically from the background-subtracted curve.
Figure 15:
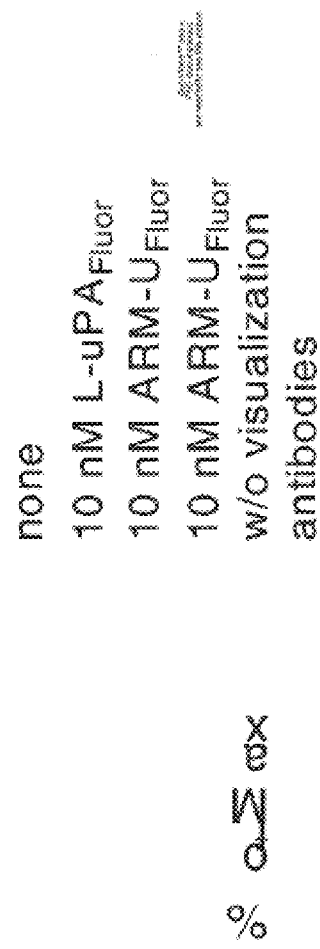
FIG. 15 shows the crude flow cytometry data for some conditions used in the experiments described herein.
Figure 16:
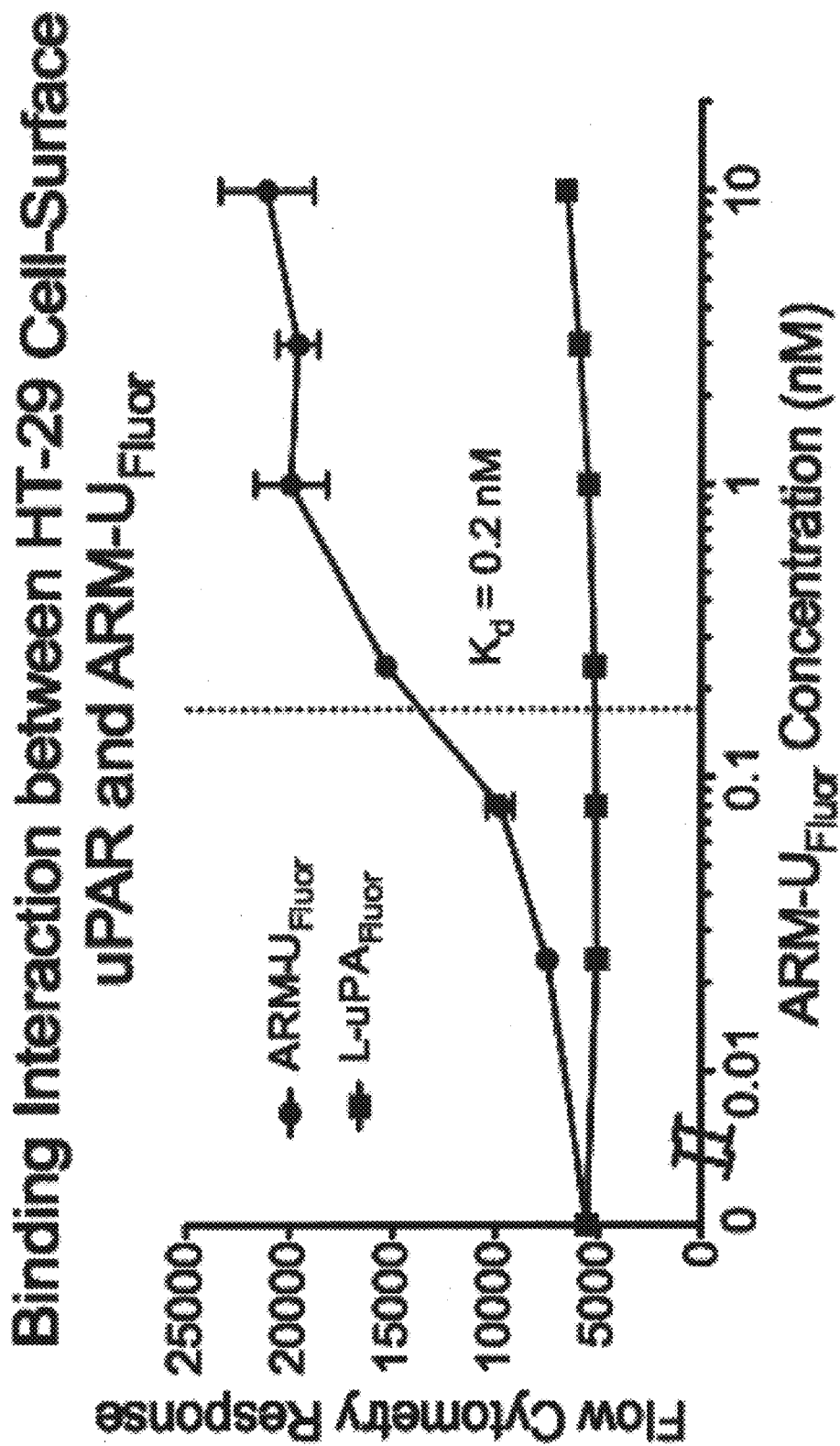
FIG. 16 shows the concentration dependence of the interaction between HT-29 cell surface uPAR and ARM-U$_{Fluor}$. The flow cytometry response represents the geometric mean of the FL-1H channel, which is measured at 488 nm excitation and 530/30 nm emission. Error bars represent the standard deviation of triplicate experiments except those for L-uPA$_{Fluor}$ 0.024 nM through 1 nM. The K$_d$ value was approximated graphically.
Figure 17:
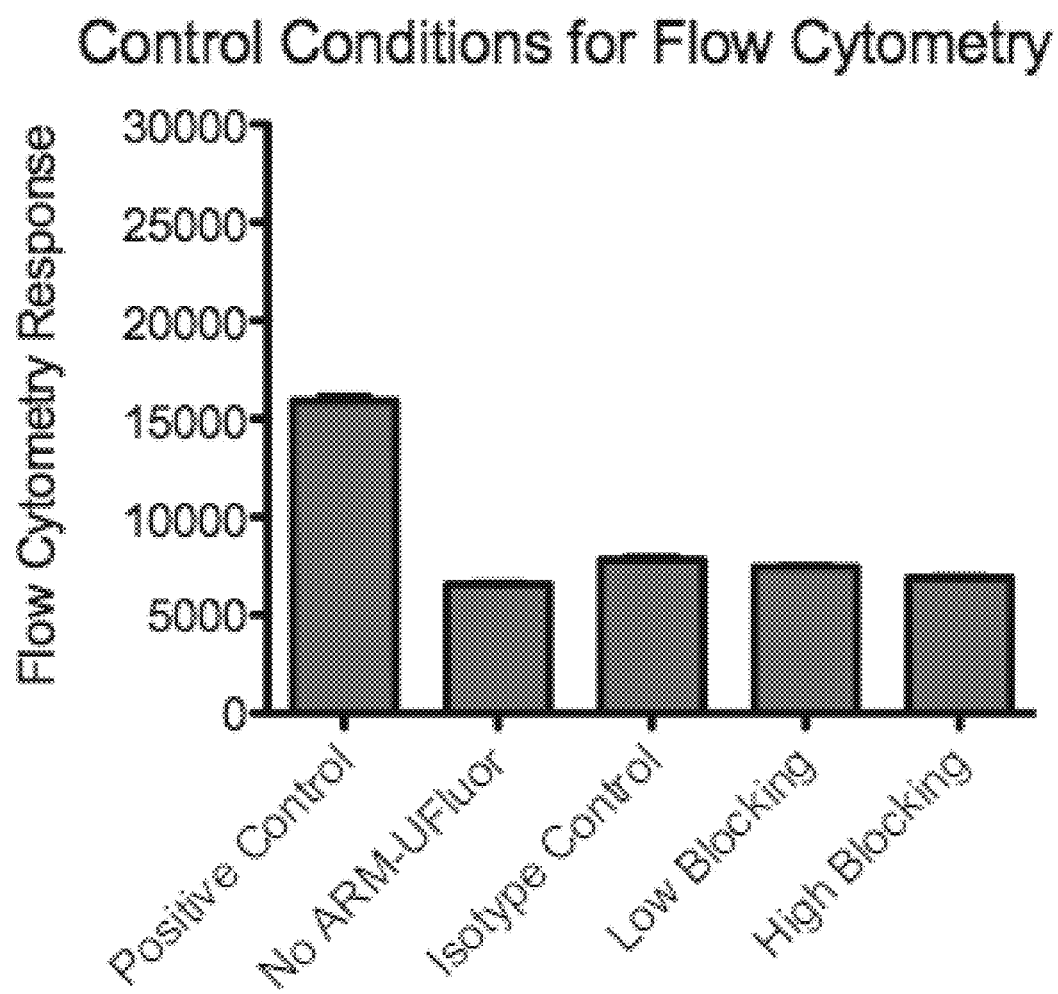
FIG. 17 shows Control conditions that show the specificity of ARM-U$_{Fluor}$ binding to surface uPAR. The flow cytometry response represents the geometric mean of the FL-1H channel, which is measured at 488 nm excitation and 530/30 nm emission. Error bars represent the standard deviation of triplicate experiments.
Figure 18A:
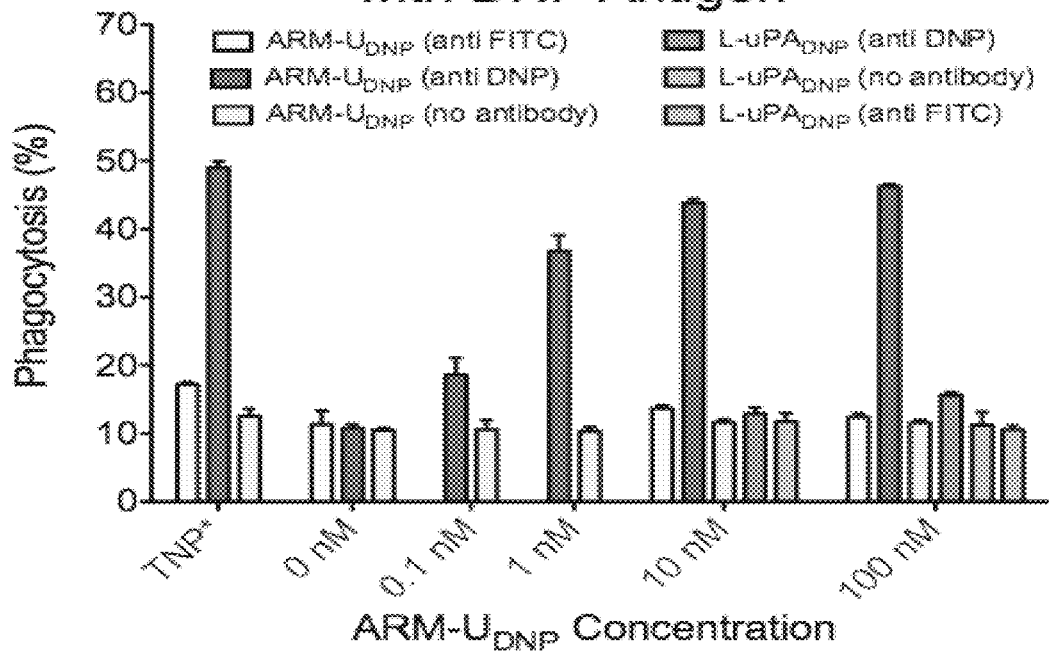
FIGS. 18A-18D shows antibody-dependent cellular phagocytosis of A172 cancer cells directed by ARM-U$_{DNP}$ (18A), A172 cancer cells directed by ARM-U$_{Fluor}$ (18B), HT29 cancer cells directed by ARM-U$_{DNP}$ (18C), and HT29 cancer cells directed by ARM-U$_{Fluor}$ (18D). Error bars represent standard deviations of triplicate experiments. * TNP and FITC conditions represents treating the target cells with either 2, 4, 6-trinitrophenylsulfonic acid (340µM) or fluorescein isothiocyanate (2.6 nM). * 1.0 rather than 1.5 equiv of compound 2 was used in the experiments with HT-29 cells.
Figure 18B:
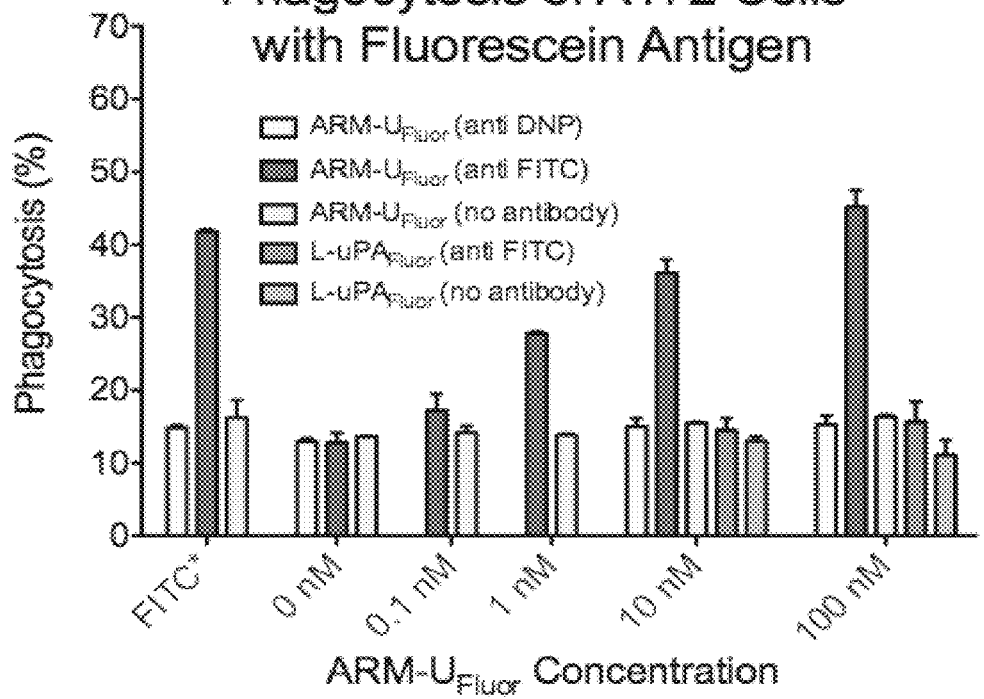
Figure 18C:
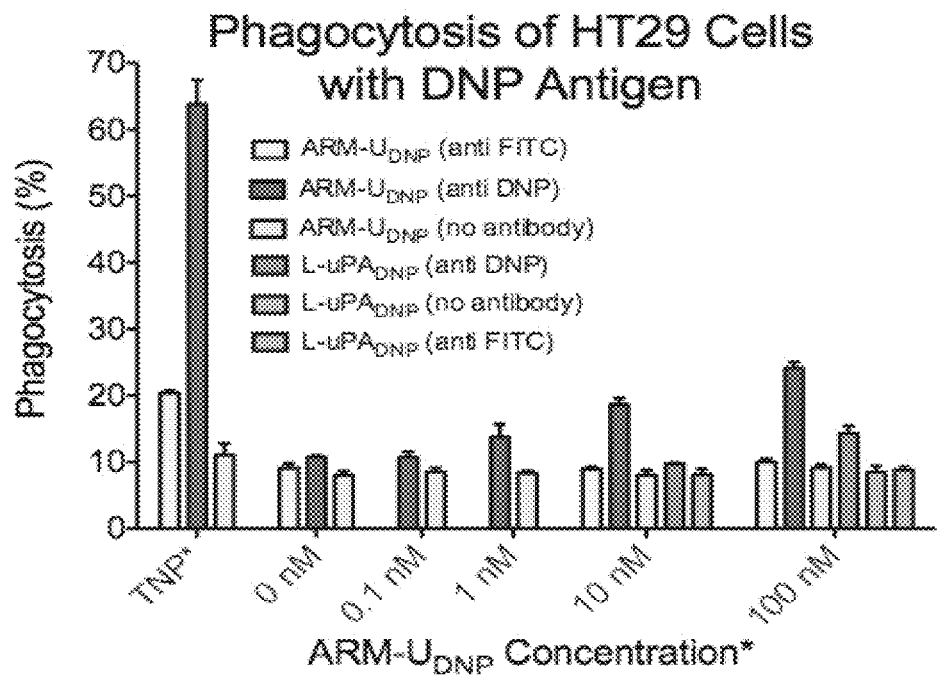
Figure 18D:
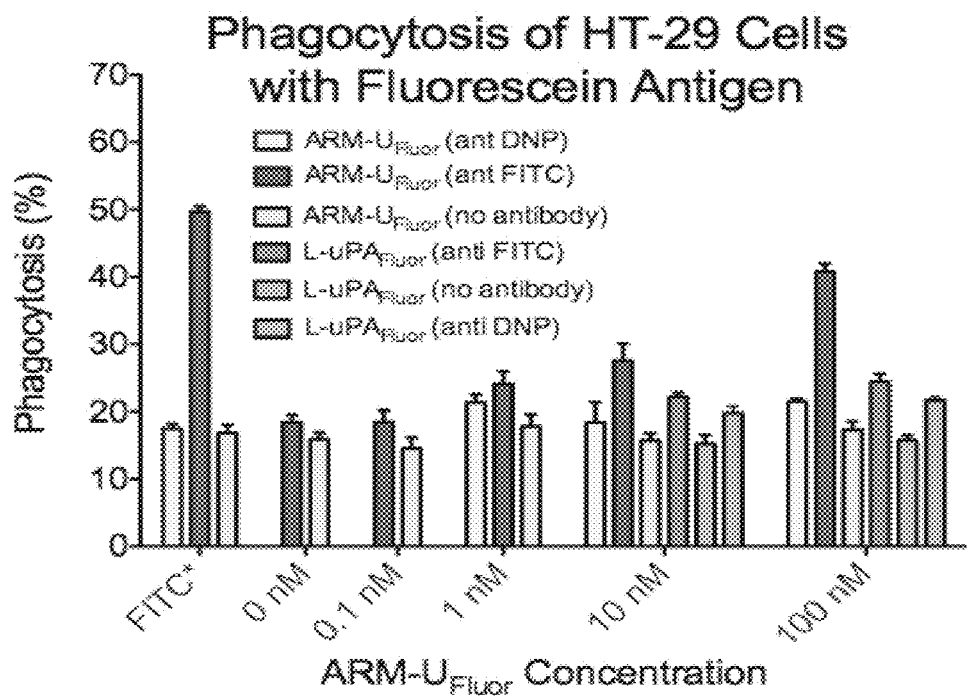
Figure 19:
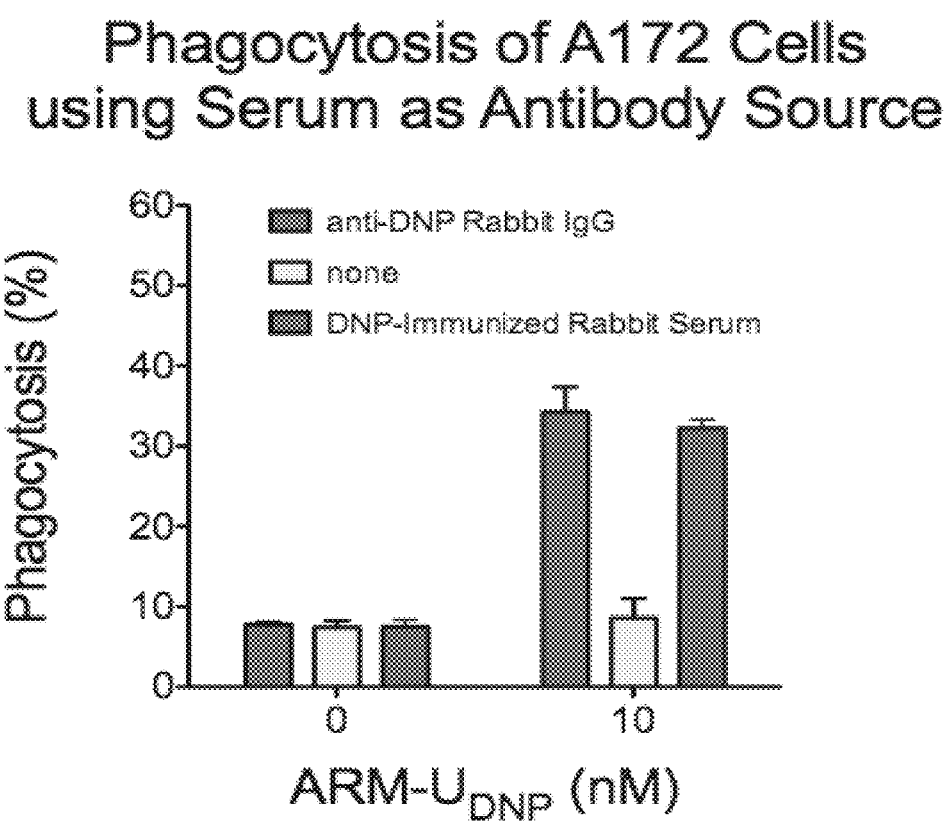
FIG. 19 shows Antibody-dependent cellular phagocytosis of A172 cells directed by ARM-U$_{DNP}$. Final serum concentration=0.5%. Final anti-DNP concentration=10 µg/mL. Error bars represent standard deviations of triplicate experiments.
Figure 20:
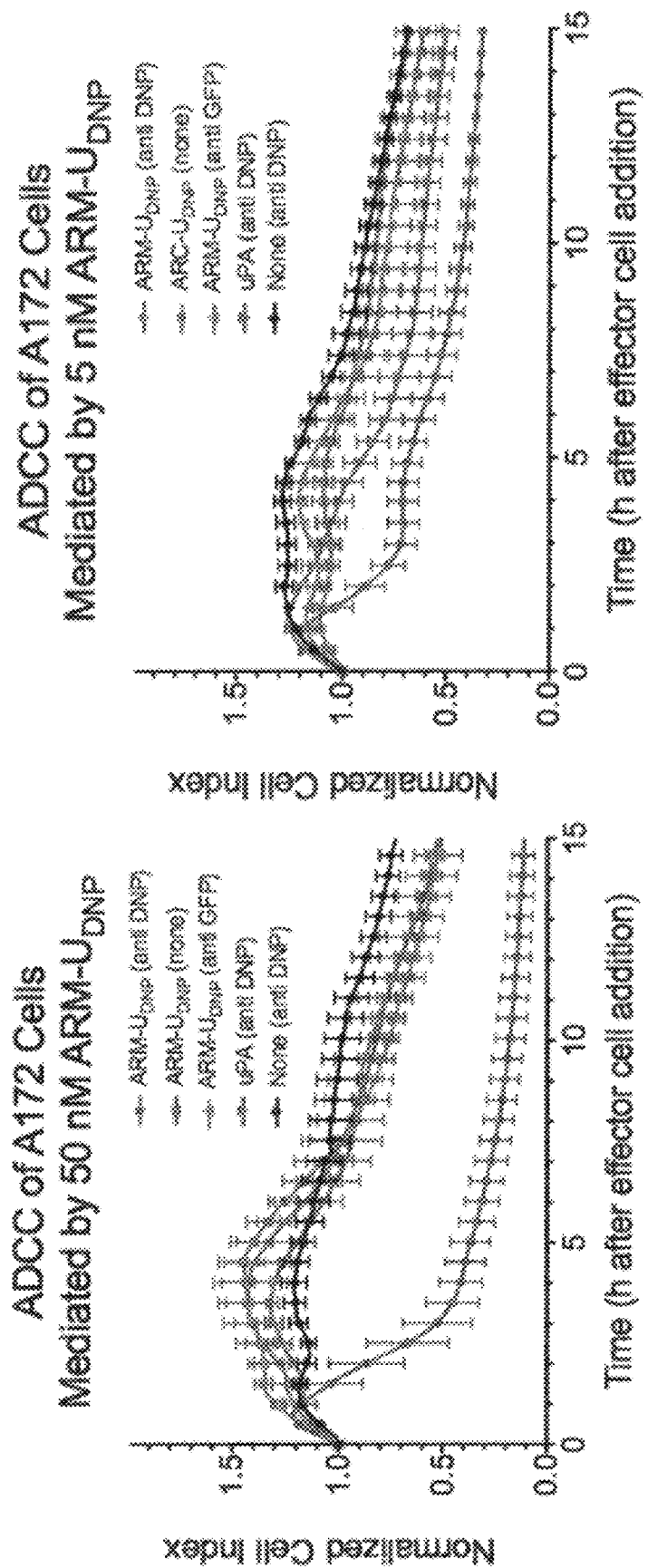
FIG. 20 shows the antibody-dependent cellular cytotoxicity of A172 cancer cells directed by ARM-U$_{DNP}$. A. 50 nM and B 4 nM. Cell index values were normalized immediately after effector cell addition. Error bars represent standard deviations of triplicate experiments.
Figure 21:
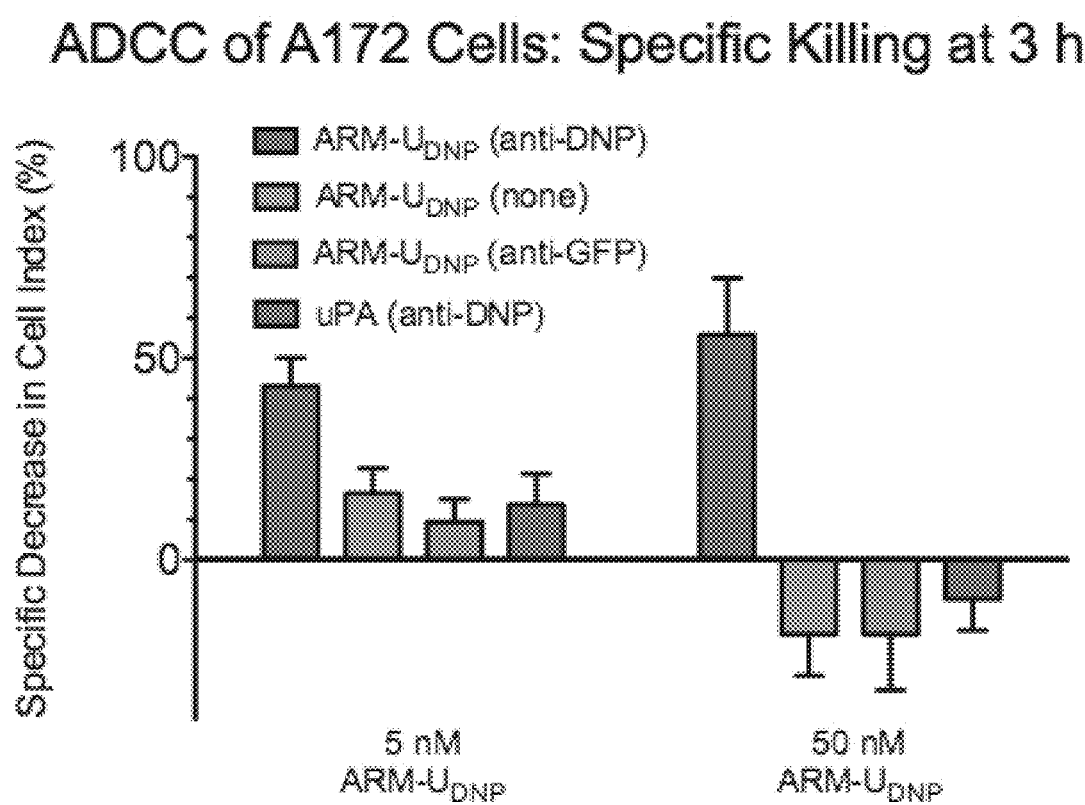
FIG. 21 shows antibody-dependent cellular cytotoxicity, as measured by the Roche xCelligence System, of A172 cells by freshly isolated PBMCs (60:1 effector:target). Antibody concentration=27 µg/mL. At 3 h, the specific cytotixicity was calculated as the specific decrease in cell index compared to cells treated with only anti-DNP antibody and PBMCs. Data points represent average values of triplicate experiments ±standard deviation.
Figure 22:
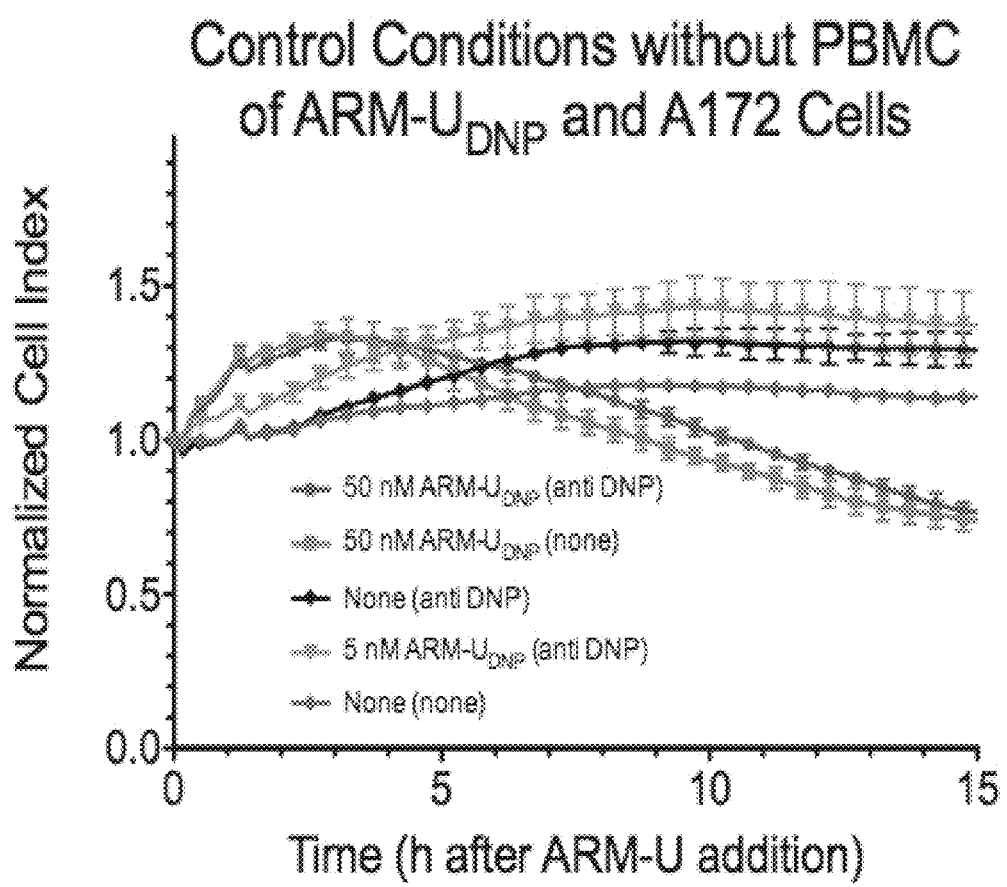
FIG. 22 shows control conditions for antibody-dependent cellular cytotoxicity of A172 cancer cells directed by ARM- $U_{DNP}$. Cell index values were normalized immediately after ARM-U addition. Error bars represent standard deviations of triplicate experiments.
Figure 23:
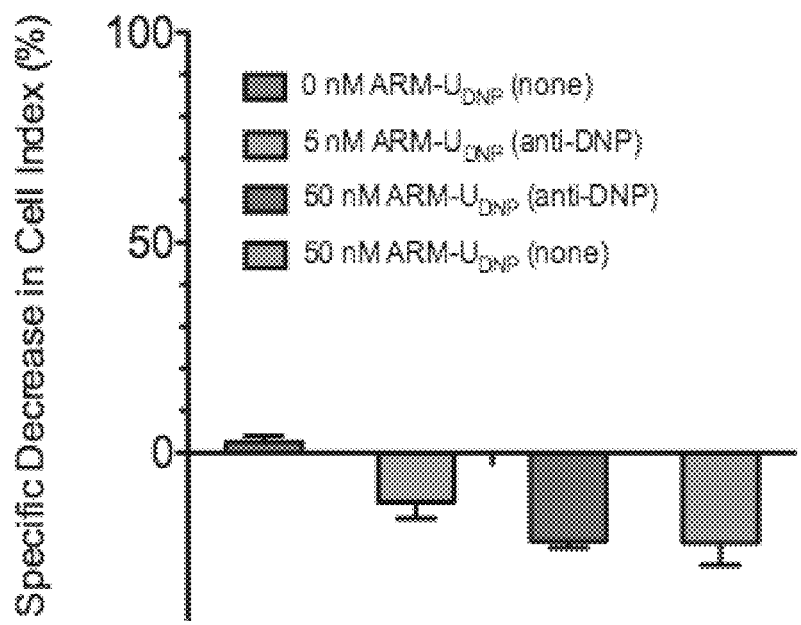
FIG. 23 shows controls for antibody-dependent cellular cytotoxicity, as measured by the Roche xCelligence System, of A172 cells without PBMCs. Antibody concentration=27 µg/mL. At 3 h, the specific cytotixicity was calculated as the specific decrease in cell index compared to cells treated with only anti-DNP antibody. Data points represent average values of triplicate experiments ±standard deviation.
Figure 24:
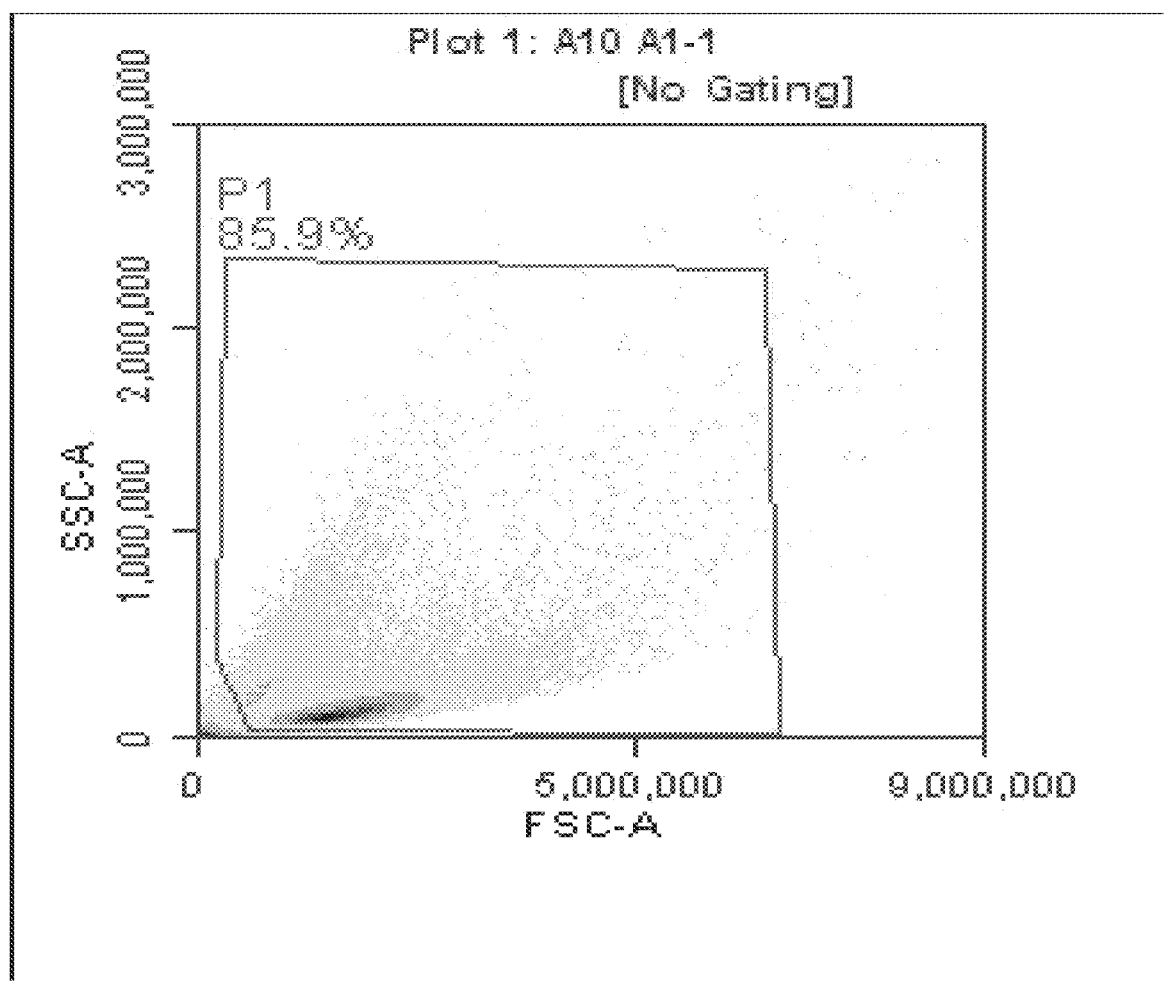
FIG. 24 shows a representative example of the initial gating of flow cytometry data used the in the examples to verify the mechanism of action of the present compounds.
Figure 25:
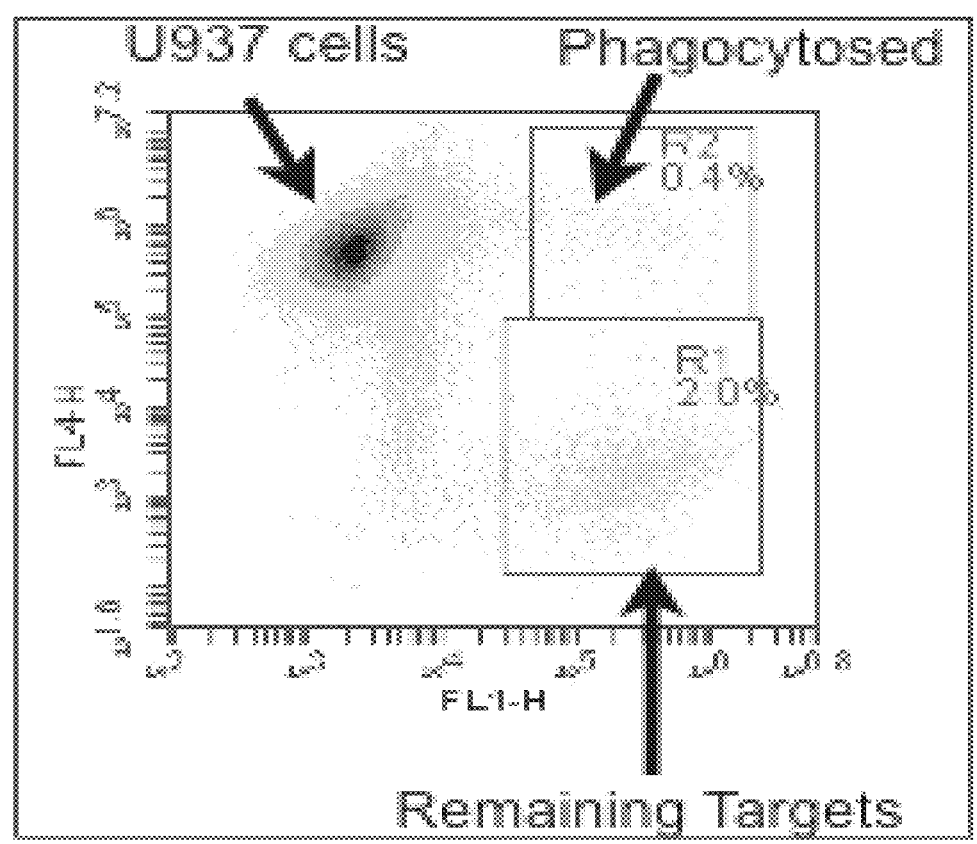
FIG. 25 shows a representative example of the final gating of flow cytometry data used the in the examples to verify the mechanism of action of the present compounds.

Scheme S3, FIG. 8, shows the synthetic strategy used to access compound 3.

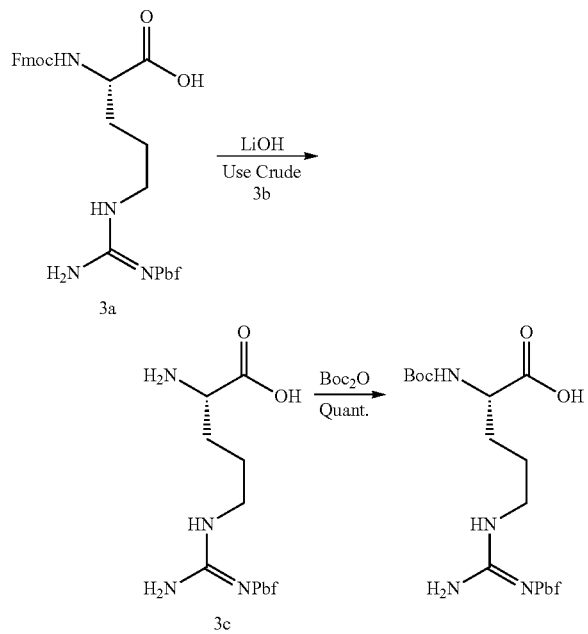

Synthesis of carbamate 3c Into a flask were added Fmoc-Arg(Pbf)-OH (1.98 g, 3.05 mmol, 1 equiv), dioxane (10 mL, 0.3 M), water (5 mL, 0.6 M), and lithium hydroxide (2 M aqueous, 4.6 mL, 9.2 mmol, 3 equiv). The mixture was stirred (2.5 h, producing precipitate), diluted with water (10 mL), and washed with EtOAc (20 mL). The aqueous phase was used directly in the next step.

To the aqueous phase containing crude amine 3b was added sodium hydroxide (1 M aqueous, 6 mL, 6 mmol, 2 equiv). Di-tert-butyl dicarbonate (864 mg, 3.97 mmol, 1.3 equiv) was dissolved in dioxane (20 mL, 0.15 M) and added. The mixture was stirred (19 h), concentrated under reduced pressure, diluted with water (30 mL) and sodium carbonate (5% aqueous, 3 mL, producing pH=9), washed with ether (40 mL), acidified with hydrochloric acid (1 M aqueous, until pH=1), extracted with ethyl acetate (3×30 mL), and dried with sodium sulfate. Volatiles were removed under reduced pressure to yield pure carbamate 3c (quantitative), a fraction of which was used directly in the next step. Product analysis is consistent with commercially available material.[5]

[5] Boc-Arg(Pbf)-OH can be purchased from Sigma-Aldrich.

$^1$H NMR ($CDCl_3$, 400 MHz) δ6.58-6.30 (m, 3H), 5.65-5.55 (brs, 1H), 4.25 (q, J=6.6 Hz, 1H), 3.25-3.10 (brs, 2H), 2.93 (s, 2H), 2.53 (s, 3H), 2.47 (s, 3H), 2.07 (s, 3H), 1.95-1.55 (m, 4H), 1.44 (s, 6H), 1.41 (s, 9H).

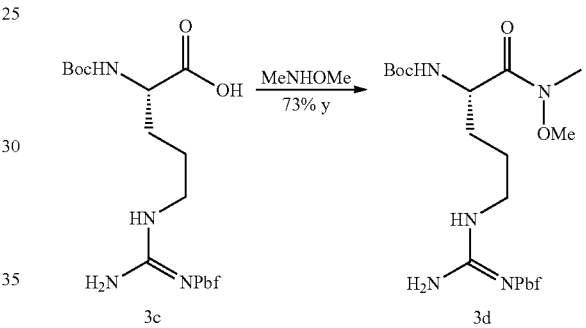

Synthesis of amide 3d Into a flask were added one third of crude acid 3c (1.0 mmol, 1 equiv), N,O-dimethylhydroxylamine hydrochloride (195 mg, 2.00 mmol, 2 equiv), EDC hydrochloride (250 mg, 1.30 mmol, 1.3 equiv), HOBt hydrate (230 mg, 1.50 mmol, 1.5 equiv), acetonitrile (4 mL, 0.3 M), and N-methylmorpholine (165 µL, 1.50 mmol, 1.5 equiv). The mixture was stirred (18 h), diluted with ethyl acetate (40 mL), washed with sodium chloride (50% saturated aqueous, 30 mL), a mixture (1:1, 30 mL) of citric acid (5% aqueous) and brine, a mixture (1:1, 30 mL) of sodium bicarbonate (saturated) and sodium carbonate (10% aqueous), and again with sodium chloride (50% aqueous), and dried with sodium sulfate. Volatiles were removed under reduced pressure to yield nearly pure amide 3d (530 mg, 0.93 mmol, 93% yield from carbamate 3a). Alternately, amide 3d can be prepared by first performing the amide coupling and then exchanging the amine protecting group. The crude material obtained from 1.5 mmol of starting carbamate 3a was purified by column chromatography (50 mL silica gel, 3:1 EtOAc/DCM) to yield amide 3d (623 mg, 1.09 mmol, 73% yield). $^1$H NMR signals were assigned by $^1$H-$^1$H COSY.

$^1$H NMR ($CDCl_3$, 500 MHz) δ6.40-2.22 (brs, 1H, guanidineNH), 6.18-6.06 (brs, 2H, guanidine-$NH_2$), 5.47 (d, J=8.3 Hz, 1H, Boc-NH), 4.68-4.58 (m, 1H, Arg-α), 3.72 (s, 3H, OMe), 3.40-3.30 (m, 1H, Arg-δ), 3.21-3.10 (m, 1H, Arg-δ), 3.18 (s, 3H, NMe), 2.94 (s, 2H, Pbf), 2.57 (s, 3H, Pbf), 2.51 (s, 3H, Pbf), 2.08 (s, 3H, Pbf), 1.75-1.52 (m, 4H, Arg-β, Arg-γ), 1.45 (s, 6H, Pbf), 1.41 (s, 9H, Boc); $^{13}$C NMR (CDCl$_3$, 125 MHz) δ172.58, 158.56, 156.15, 138.27, 133.05, 132.20, 124.45, 117.33, 86.24, 80.01, 61.56, 49.67, 43.19, 40.78, 32.03, 30.71, 28.70, 28.53, 29.29, 28.12, 24.89, 19.19, 17.82, 12.39; IR (film, cm-1) 3338, 2978, 2929, 1712, 1650, 1621, 1548, 1168, 1107; HRMS calculated for [C$_{26}$H$_{42}$N$_5$O$_7$SH]$^+$, requires m/z=570.2956, found m/z=570.2957 (ESI); TLC (2:1) EtOAc/DCM, permanganate, R$_f$=0.28.

$^{13}$C NMR (CDCl$_3$, 125 MHz) 3207.42, 158.65, 156.26, 155.82, 138.08, 132.68, 132.02, 124.55, 117.41, 86.31, 79.74, 59.56, 43.09, 40.59, 28.48, 28.20, 26.57, 25.14, 19.18, 17.84, 12.34; IR (film, cm$^{-1}$) 3334, 1699, 1552, 1246, 1156, 1091; HRMS calculated for [C$_{25}$H$_{39}$N$_4$O$_6$SH]$^+$, requires m/z=525.2741, found m/z=525.2738 (ESI); TLC (3:1) EtOAc/DCM, UV, R$_f$=0.38.

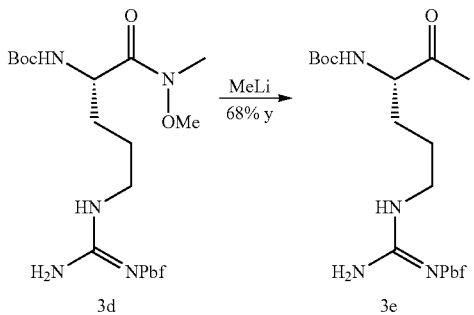

3d → 3e

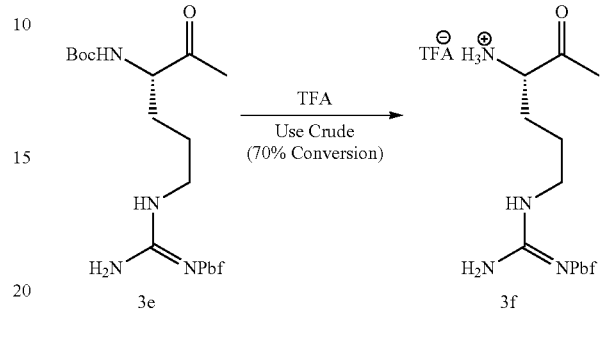

3e → 3f

Synthesis of ketone 3e Into a flame-dried flask backfilled with argon were added amide 3d (566 mg, 1.00 mmol, 1 equiv) and THF (20 mL, 0.05 M). The flask was capped with a rubber septum, flushed with argon, and cooled in a dry ice/acetone bath (−78° C., 10 min). Methyllithium (1.6 M in ether, 3.13 mL, 5.00 mmol, 5 equiv), was added dropwise (over 5 min, becoming orange). The mixture was stirred (1.5 h, quenched with ammonium chloride (saturated aqueous, 5 mL, becoming colorless), allowed to warm to ambient temperature, diluted with water (30 mL) and brine (30 mL), extracted with EtOAc (50+20 mL), and dried with sodium sulfate. Volatiles were removed under reduced pressure, and the crude material was purified by column chromatography (50 mL silica gel, 3:2 EtOAc/DCM) to yield ketone 3e (388 mg, 0.682 mmol, 68% yield). $^1$H NMR signals were assigned by $^1$H-$^1$H COSY and by comparison to signals from the starting materials.

$^1$H NMR (CDCl$_3$, 500 MHz) δ 6.22-6.05 (brs, 1H, guanidineNH), 6.05-5.97 (brs, 2H, guanidine-NH$_2$), 5.43 (d, J=7.1 Hz, 1H, Boc-NH), 4.33-4.25 (m, 1H, Arg-α), 3.43-3.34 (m, 1H, Arg-δ), 3.22-3.13 (m, 1H, Arg-δ), 2.95 (s, 2H, Pbf), 2.58 (s, 3H, Pbf), 2.52 (s, 3H, Pbf), 2.19 (s, 3H, Me), 2.09 (s, 3H, Pbf), 1.88-1.79 (m, 1H, Arg-β/Arg-γ), 1.70-1.52 (m, 3H, Arg-β, Arg-γ), 1.45 (s, 6H, Pbf), 1.41 (s, 9H, Boc);

Synthesis of amine 3f Into a flask were added ketone 3f (388 mg, 0.740 mmol, 1 equiv) and DCM (3.6 mL, 0.2 M). The flask was capped with a rubber septum, flushed with argon, and cooled in an ice bath (0° C., 10 min). Trifluoroacetic acid (0.4 mL, giving a 10% solution in DCM) was added. The argon line was removed, and the mixture was stirred (3 h, approximately 30% conversion as measured by LC/MS). Additional trifluoroacetic acid (0.2 mL, giving a 15% solution in DCM) was added. The mixture was stirred (additional 1.5 h, approximately 75% conversion by LC/MS and trace amounts of Pbf-deprotected material), and diluted with toluene (5 mL). Volatiles were removed under reduced pressure (2×toluene azeotrope), and the crude material (approximately 70% conversion by $^1$H NMR) was used directly for the next step. Retention of stereochemistry was shown by coupling amine 3f to each enantiomer of Boc-Phe-ONHS; each produced a single diastereomer that could be readily distinguished by $^1$H NMR.

$^1$H NMR (CD$_3$OD, 500 MHz, major signals) δ 4.19 (dd, J$_1$=8.1 Hz, J$_2$=4.1 Hz, 1H, Arg-α), 3.27-3.20 (m, 2H, Arg-δ), 3.00 (s, 2H, Pbf), 2.56 (s, 3H, Pbf), 2.50 (s, 3H, Pbf), 2.21 (s, 3H, Me), 2.08 (s, 3H, Pbf), 2.05-1.97 (m, 1H, Arg-β/Arg-γ), 1.84-1.47 (m, 3H, Arg-β, Arg-γ), 1.45 (s, 6H, Pbf); LC/MS elutes at 0.74 min, calculated for [C$_2$OH$_{32}$N$_4$O$_4$SH]$^+$, requires m/z=425.22, found m/z=425.14 (ESI).

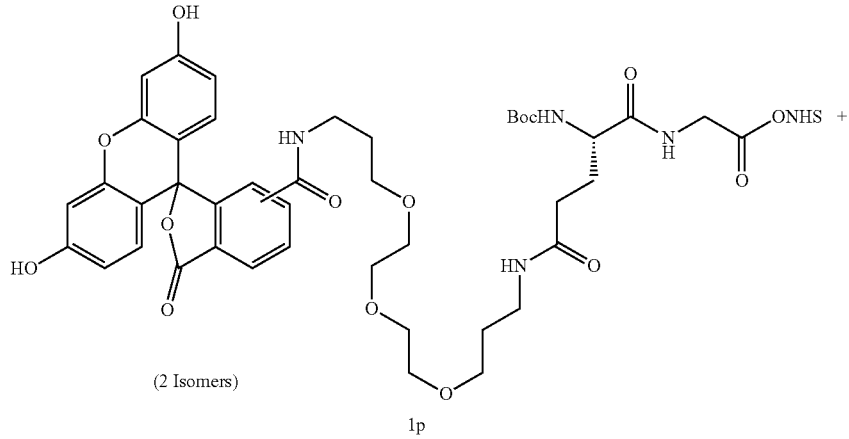

(2 Isomers)

1p

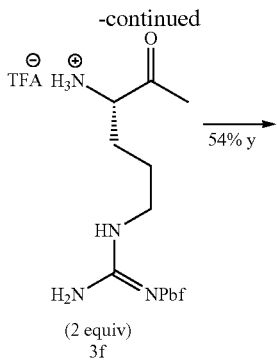

(2 equiv)
3f

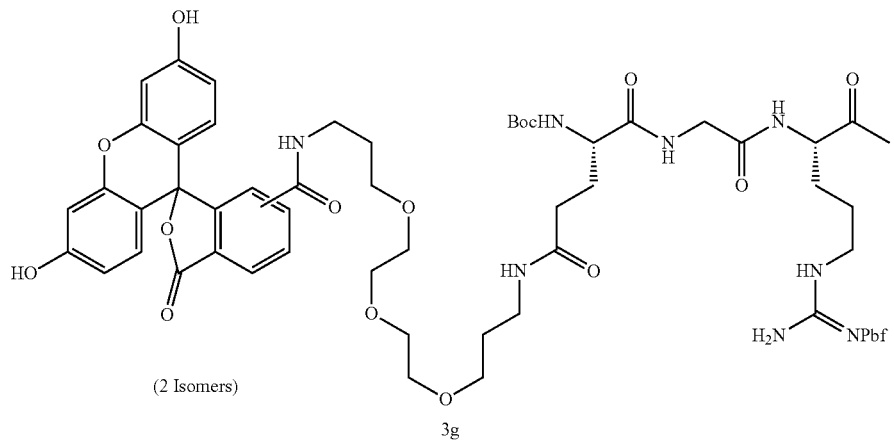

(2 Isomers)
3g

Synthesis of peptide 3g Into a flask were added 40% of crude NHS ester 1p (0.37 mmol, 1 equiv), crude amine 3f ((70% pure, 0.740 mmol, 2 equiv), THF (3.7 mL, 0.1 M), and Hünig's base (258 µL, 1.48 mmol, 4 equiv, producing neutral pH). The mixture was stirred in the dark (2.5 h, 60% conversion by LC/MS, becoming slightly acidic). Additional Hünig's base (65 µL, 0.37 mmol, 1 equiv, producing slightly basic pH) was added. The mixture was stirred (additional 1 h, full conversion by LC/MS), diluted with THF (10 mL) and DCM (40 mL), washed with sodium hydrogen sulfate (0.1 M, 60 mL), and dried with sodium sulfate. Volatiles were removed under reduced pressure, and the crude material was purified by column chromatography (50 mL silica gel, DCM+10-20% MeOH) to yield amide 3g (253 mg, 0.199 mmol, 54% yield).

$^1$H NMR (CD$_3$OD, 500 MHz) δ 8.41 (s, 0.5H, Ar), 8.18 (dd, J$_1$=8.0 Hz, J$_2$=1.6 Hz, 0.5H, Ar), 8.12 (dd, J$_1$=8.0 Hz, J$_2$=1.4 Hz, 0.5H, Ar), 8.04 (d, J=8.1 Hz, 0.5H, Ar), 7.63 (s, 0.5H, Ar), 7.28 (d, J=8.0 Hz, 0.5H, Ar), 6.70-6.66 (m, 2H, Ar), 6.60 (t, J=9.0 Hz, 2H, Ar), 6.55-6.50 (m, 2H, Ar), 4.36-4.30 (m, 1H, Arg-α), 4.00-3.95 (m, 1H, Glu-α), 3.87 (s, 2H, Gly-α), 3.64-3.34 (m, 14H, 6×CH$_2$—O, CH$_2$—NH), 3.24-3.10 (m, 4H, CH$_2$—NHAr, Arg-δ), 2.95 (s, 2H, Pbf), 2.55 (s, 3H, Pbf), 2.48 (s, 3H, Pbf), 2.27 (q, J=7.8 Hz, 2H, Glu-γ), 2.08 (s, 3H, Me), 2.05 (s, 3H, Pbf), 2.06-2.00 (m, 1H, Glu-β), 1.95-1.44 (m, 9H, Glu-β, 2×C—CH$_2$—C, Arg-β, Arg-γ), 1.41 (s, 6H, Pbf), 1.38 (s, 9H, Boc); $^{13}$C NMR (CDCl$_3$, 125 MHz), 208.47, 175.18, 174.80, 171.61, 170.58, 168.11, 167.83, 161.60, 159.80, 158.02, 157.95, 154.04, 142.26, 139.31, 137.90, 135.40, 134.40, 133.46, 130.18, 128.77, 126.25, 126.00, 125.77, 124.88, 124.00, 118.39, 113.91, 111.00, 110.92, 103.63, 87.65, 80.86, 71.45, 71.24, 71.15, 71.04, 70.89, 70.23, 70.17, 69.86, 69.79, 59.94, 55.88, 43.93, 43.59, 41.37, 39.08, 38.97, 37.92, 37.86, 33.16, 30.28, 30.04, 28.76, 28.21, 26.81, 26.26, 19.62, 18.42, 12.54; IR (film, cm-1) 3328, 2972, 2928, 2863, 1643, 1614, 1545, 1450, 1247, 1174, 1113; HRMS calculated for [C$_{68}$H$_{81}$N$_8$O$_{18}$SH]$^+$, requires m/z=1271.5541, found m/z=1271.5535 (ESI); TLC DCM+15% MeOH, UV/permanganate, R$_f$=0.32.

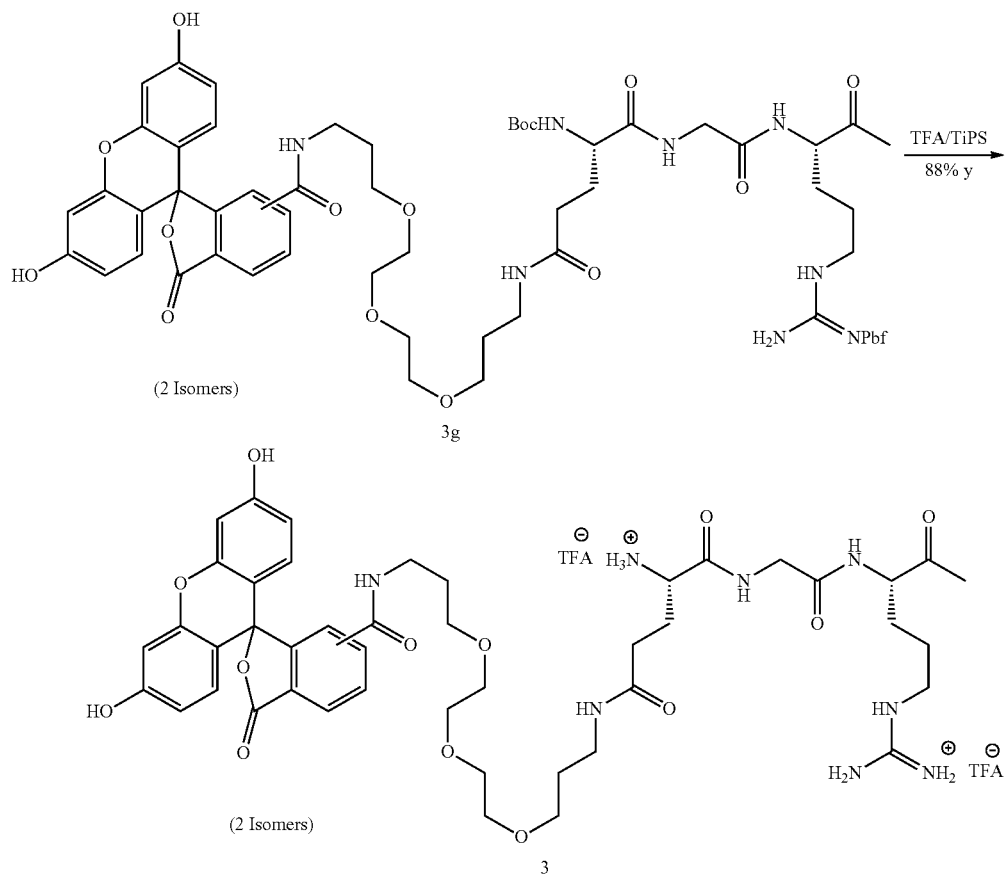

3g 3 (2 Isomers)

Synthesis of ketone 3 Into a flask were added protected ketone 3g (127 mg, 1.00 mmol, 1 equiv) and a mixture of TFA, TiPS, and water (38:1:1, 3 mL, 0.3 M). The mixture was stirred in the dark (3.5 h) and diluted with toluene (5 mL). Volatiles were removed under reduced pressure (2×toluene azeotrope). The crude mixture was diluted with deuterium oxide (3 mL) and deuterated methanol (1 mL) and washed with deuterated chloroform (2×2 mL). The aqueous phase, which contained mostly pure ketone 3, which was purified by semi-preparative RP-HPLC ($C_{18}$ column, water+ 0.1% TFA with 15-40% MeCN over 30 min, product isomers elute at 12.1 and 12.5 min) to yield pure ketone 3 (101 mg, 0.0881 mmol, 88% yield) as a mixture (approximately 1:1) of regioisomers at fluorescein and as a yellow solid. The regioisomeric ratio was measured by $^1$H NMR. $^1$H NMR signals were assigned by $^1$H-$^1$H COSY. Material was stored at −20° C. as an aqueous solution.

$^1$H NMR (D$_2$O, 400 MHz) δ 8.44 (d, J=1.3 Hz, 0.5H, fluor), 8.15 (d, J=1.2 Hz, 0.5H, fluor), 8.00 (d, J=8.3 Hz, 0.5H, fluor), 7.96 (d, J=8.9 Hz, 0.5H, fluor), 7.43 (s, 0.5H, fluor), 7.19 (d, J=7.3 Hz, 0.5H, fluor), 7.00 (d, J=9.1 Hz, 1H, fluor), 6.92 (d, J=9.0 Hz, 1H, fluor), 6.84-6.80 (m, 2H, fluor), 6.74 (dd, $J_1$=9.0 Hz, $J_2$=2.2 Hz, 1H, Ar), 6.67 (dd, $J_1$=9.4 Hz, $J_2$=2.1 Hz, 1H, fluor), 4.36-4.32 (m, 1H, Arg-α), 4.06-4.01 (m, 1H, Glu-α), 4.00 (d, J=17.1 Hz, 1H, Gly-α), 3.94 (d, J=16.7 Hz, 1H, Gly-α), 3.59-3.04 (m, 18H, 6×CH$_2$—O, Arg-δ, 2×CH$_2$—NHCO), 2.38-2.30 (m, 2H, Glu-γ), 2.13 (s, 3H, Me), 2.12-2.06 (m, 2H, Glu-β), 1.90-1.46 (m, 8H, Arg-β, Arg-γ, 2×C—CH$_2$—C); $^{13}$C NMR (D$_2$O+1.5% MeOH, 125 MHz) δ211.61, 174.27, 174.25, 171.22, 170.31, 168.69, 168.39, 168.21, 167.87, 167.24, 163.05 (q, J=35.6 Hz), 157.60, 157.33, 157.22, 141.24, 139.75, 139.13, 136.79, 132.79, 132.07, 131.97, 131.84, 130.59, 130.16, 129.87, 129.53, 129.09, 127.39, 118.73, 118.28, 116.26 (q, J=291.7 Hz), 114.97, 114.65, 103.14, 103.14, 70.18, 70.03, 69.90, 69.86, 69.38, 69.20, 68.94, 68.90, 59.70, 53.19, 42.73, 41.11, 38.17, 37.07, 31.38, 28.96, 28.80, 27.28, 27.11, 26.72, 24.95; IR (film, cm$^{-1}$) 3297, 3077, 2941, 2876, 1659, 1634, 1593, 1540, 1197, 1176, 1131; HRMS calculated for [$C_{45}H_{57}N_8O_{13}H$]$^+$, requires m/z=919.4196, found m/z=919.4169 (ESI); RP-HPLC $C_{18}$ column, 15-40% MeCN in water+0.1% TFA, flow=1.0 m/min, monitored at 214 nm, isomers elute overlapping at 16.8 and 1

Biological Evaluation
Buffers and Solutions
    pH were adjusted with 1 M NaOH or 2 M HCl.
    Antibody-Loading Buffer
    50 mL PBS Tween
    50 mg BSA (1 mg/mL)
    stored at 4° C.
    Coating Buffer
    100 mL water
    530 mg Na$_2$CO$_3$ (50 mM)
    to pH 9.6
    Color-Free ADCP Media
    RPMI Medium 1640, liquid
    ATCC #11835-030
    without phenol red
    supplemented with 5% HI-FBS
    and 1% penicillin-streptomycin Colored ADCP Media
RPMI Medium 1640, liquid
Invitrogen #11875-093
supplemented with 5% HI-FBS
and 1% penicillin-streptomycin
Destaining Solution
50 mL water
40 mL methanol
10 mL acetic acid
DPBS Solution
Invitrogen #14190-144
Dulbecco's modified Eagle's medium
ATCC #30-2002
EDTA Detachment Solution
210 mL DPBS
392 mg EDTA disodium salt (5.0 mM)
84 mg EGTA (1.0 mM)
to pH 7.4
0.22 µM sterile filter
FBS ADCC Media
RPMI Medium 1640, liquid
ATCC #11835-030
without phenol red
supplemented with 10% HI-FBS
and 1% penicillin-streptomycin
stored at 4° C.
FBS-free ADCC Media
RPMI Medium 1640, liquid
ATCC #11835-030
without phenol red
supplemented with 1% penicillin-streptomycin
stored at 4° C.
Flow Incubation Buffer
100 mL DPBS
12 mg $NaN_3$ (2 mM)
180 mg EDTA (5 mM)
to pH 7.4
100 mg BSA (1 mg/mL)
stored at 4° C.
Hanks Balanced Salt Solution
Invitrogen #14175-095
HEPES/saline (2×)
100 mL water
1.6 g NaCl (270 mM)
1.0 g HEPES (42 mM)
0.20 g dextrose (11 mM)
74 mg KCl (10 mM)
27 mg $Na_2HPO_4$ (2 mM)
to pH 7.05
McCoy's 5A medium
ATCC #30-2007
Non-Reducing Loading Buffer
3.8 mL water
1 mL 0.5 M tris HCl at pH 6.8
1.6 mL 10% sodium dodecyl sulfate
0.4 mL 1% bromophenol blue
0.8 mL glycerol
PBS
1 L water
8.0 g NaCl (137 mM)
0.20 g KCl (2.7 mM)
1.44 g $Na_2HPO_4$ (10 mM)
0.24 g $KH_2PO_4$ (1.8 mM)
to pH 7.4
PBS-Tween
300 mL PBS
60 mg $NaN_3$ (0.02%)
30 µL tween-80 (0.01%)
Protein-Loading Buffer
70 mL PBS Tween
130 mg EDTA (5 mM)
pH to 7.4
70 mg BSA (1 mg/mL)
stored at 4° C.
Reporter Buffer
45 mL water
5 g diethanolamine (10%)
5 mg $MgCl_2$ (0.1 mg/mL)
10 mg $NaN_3$ (0.02%)
to pH 9.6
RPMI-1640 medium
Invitrogen #11875-093
stored at 4° C.
Running buffer
15.1 g tris base
94 g glycine
5 g sodium dodecyl sulfate
5 L water
to pH 8.3
Staining Solution
100 mL destaining solution
100 mg Coomassie blue
Substrate Solution
20 mL reporter buffer
20 mg p-nitrophenyl phosphate (1 mg/mL)
stored at 4° C.
Tris buffer
100 mL water
585 mg NaCl (100 mM)
158 mg Tris·HCl (10 mM)
to pH 7.5
uPA Buffer
30 mL water
204 mg $NaOAc·3H_2O$ (50 mM)
176 mg NaCl (100 mM)
11 mg EDTA disodium salt (1 mM)
to pH 5.0
0.22 µM sterile filter Proteins, Antibodies, and Reagents Alexa Fluor 488 donkey anti-rabbit IgG
Invitrogen #A21206 (Lot #439378)
The purchased solution was stored at 4° C.
Anti-DNP Antibody Produced in Rabbit Whole Antiserum
Sigma #D9656 (Lot #089K4764)
The purchased frozen solution was thawed, split into
    aliquots, and stored frozen at −20° C.
Anti-Dinitrophenyl-KLH Rabbit IgG Fraction
Invitrogen #A6430 (Lot 807872)
The purchased solution was stored at 4° C.
Anti Fluorescein/Oregon Green goat IgG fraction
Invitrogen #A-11095 (Lot #675497)
The purchased solution was split into aliquots, each of
    which was frozen at −20° C. The
aliquot being used was stored at 4° C. for up to 3 months.
Anti-Fluorescein/Oregon Green rabbit IgG fraction
Invitrogen #A889 (Lot #645149)
The purchased solution was stored at 4° C.
Anti-Green Fluorescent Protein Rabbit IgG Fraction
Invitrogen #A11122 (Lot 743636)
The purchased solution was stored at 4° C.

Anti-Goat IgG (H&L) (Rabbit) Antibody Alkaline Phosphatase Conjugated
Rockland #605-4502 (Lot #22999)
The purchased solution was stored at 4° C.
Cbz-Gly-Gly-Arg-AMC
Bachem, #1140
Fetal Bovine Serum, Qualified, Heat-Inactivated
Invitrogen #16140-071
The purchased solution split into aliquots, each of which was stored at −20° C.
Fluorescein Isothiocyanate Isomer 1
90% pure
Acros #119250010
Human HMW Urokinase (isolated from human urine)
Innovative Research #IUP-HTC (Lot #310)
The purchased solution (in the uPA buffer) was split into aliquots, each of which was frozen at −80° C.
Human LMW Urokinase
Innovative Research #IUPA-LMW (Lot #210)
The purchased solution was split into aliquots, each of which was frozen at −80° C.
Human uPAR Antibody: Polyclonal goat IgG
R&D Systems #AF807 (lot #BBS0208011)
The purchased lyophilized solid was stored at −80° C., reconstituted with 500 µL of sterile DPBS (producing a 200 µg/mL solution), and stored at 4° C.
Lympholyte-Poly
Cedarlane #CL5070
Penicillin-Streptomycin, Liquid (10,000 units penicillin; 10,000 µg Streptomycin/mL)
Invitrogen #15140-163
Rabbit anti human uPA IgG fraction
Innovative Research #IASHUPA-GF (lot #706)
The purchased solution was split into aliquots, each of which was frozen at −80° C.
Recombinant Human IFN-γ
R&D Systems #285-IF
1 µg/mL
Seeblue Prestained Standard
Invitrogen #LC5625 (Lot #670628)
The purchased solution was stored at 4° C.
Trinitrobenzene sulfonic acid
Thermo Scientific #28997
5% w/v in methanol
Trypan Blue Stain 0.4%
Invitrogen #15250
Urokinase, Human
American Research Products #12-4306 Lot #920901
The purchased lyophilized solid was stored at −80° C., reconstituted with 67 µL of the uPA buffer (producing a 1.5 µg/µL solution), and split into aliquots, each of which was frozen at −80° C.
Vybrant DiD Cell Labeling Solution
Invitrogen #V-22887
1 mM in ethanol
FL-4 fluorophore
Vybrant DiO Cell Labeling Solution
Invitrogen #V-22886
1 mM in DMF
FL-1 fluorophore
Equipment, Materials, and Software
0.16-well E-plate-16
Roche #05469830001
96 Well Flat Bottom Immuno Plate
MaxiSorp, Non Sterile, PS
Nunc #442404
C6 Flow Cytometer
Accuri
with CFlow Plus software
FlowJo software
Mini-PROTEAN Tetra Cell for Ready Precast Gels
BioRad #165-8004
Petri Dishes
BD Falcon #351029
100×15 mm
PowerPac Basic Power Supply
BioRad #164-5050
Ready Gel Tris-HCl gel 15% crosslinking
8.6×6.8 cm, 10 wells (30 uL)
BioRad #161-1103
Synergy 2 Multimode Microplate Reader
BioTek
with Gen 5 software
T-Flasks
BD Falcon #353136
75 $cm^2$ tissue culture treated
Typhoon Trio Variable Mode Imager
with ImageQuant software•Prism software
exCelligence System model RTCA-DP
Roche
RTCA software v1.2

Catalytic Inhibition

Stock solutions were prepared of compound 1 (4 µg, 104 µL total volume 2× hepes/saline buffer), uPA (4.6 µg, diluted with water to 4.6 µL total volume), and Cbz-Gly-Gly-Arg-AMC (400 µg, 7 mL total volume 20:1 tris buffer/N-methlypyrrolidinone). Into microcentrifuge tubes were added 2 µL of the uPA solution (2 µg, 37 pmol) and 1.7 µL of either the compound 1 stock solution (66 ng, 56 pmol) or 2× hepes/saline buffer to give a final volume of 3.7 µL, final uPA concentration of 10 µM, and final compound 1 concentration of 15 µM. The mixtures were allowed to stand in the dark at ambient temperature (1 h) and diluted with water 25.9 µL. An aliquot of each mixture (12 µL, 15 pmol uPA) was diluted into 738 µL of the AMC solution to give a final volume of 750 µL, a final uPA concentration of 20 nM, and a final AMC concentration of 96 µM. Triplicate aliquots of 200 µL of each solution were loaded into a 96-well plate, and the fluorescence (330 nm absorbance, 460 nm emission) was recorded at one-minute intervals for ten minutes on an automated plate-reader. Figure S1 shows these data. uPA-mediated hydrolysis of Cbz-Gly-Gly-Arg-AMC liberates free AMC, whose fluorescence is substantially greater that that of the starting peptide. Thus, the initial rate of increase of fluorescence is proportional to the amount of active uPA remaining. Slopes for each line were calculated using linear regression (Prism software) of the first five data points. While unmodified uPA produces a slope of 91.3±2.3 fluorescence units per minute, compound 1 treated uPA produces a slope of only 2.9±0.5 fluorescence units per minute, which corresponds to a 97% reduction in catalytic ability.

In-Gel Fluorescence

Stock solutions were prepared of compound 1 (4 µg, 142 µL total volume 2× HEPES/saline buffer) and compound 3 (4 µg, 36.6 µL total volume 2× HEPES/saline buffer). Into microcentrifuge tubes were added 4 µL of either HMW uPA solution (1.5 µg/µL, 6 µg) or the uPA buffer and 7 µL of either the compound 1 stock solution (98 ng), the MeK-Fluor stock solution (382 ng), or 2× HEPES/saline buffer to give a final volume of 11 µL, final uPA concentration of 10 µM, final compound 1 concentration of 15 µM, and final compound 3 concentration of 60 µM. The mixtures were allowed to stand in the dark at ambient temperature (1 h) and diluted with the non-reducing loading buffer (12 µL). An aliquot of each mixture (15 µL) was loaded into a precast gel (15% Tris-HCl). The gel was run (200 mV, 30 min), analyzed by fluorescence (488 nm excitation, 532 nm emission), stained (1 h), and destained (2 h). As shown in Figure S2, lane 3 evidences that a substantial amount of compound 1 becomes bound to uPA after incubation, whereas lane 4 shows that compound 3 does not bind uPA.

A subsequent experiment was performed to assess the selectivity of the covalent modification of uPA. The following stock solutions were prepared.

| Compound | Concentration | Solvent |
|---|---|---|
| HMW uPA | 2.0 µg/4.5 µL | 2× HEPES/Saline Buffer |
| BSA | 2.4 µg/4.5 µL | 2× HEPES/Saline Buffer |
| Rabbit anti-uPA antibody | 5.5 µg/4.5 µL | 2× HEPES/Saline Buffer |
| compound 1 | 524 ng/4.5 µL | Water |
| compound 1 | 262 ng/4.5 µL | Water |
| compound 1 | 131 ng/4.5 µL | Water |
| compound 1 | 65 ng/4.5 µL | Water |
| compound 3 | 509 ng/4.5 µL | Water |

Into microcentrifuge tubes were added 4.5 µL of the appropriate protein solution (4 µM final concentration) and 4.5 µL of the appropriate ketone solution (6, 12, 24, 48 µM final concentrations). Mixtures were mixed, allowed to stand at ambient temperature (1 h, in the dark), and diluted with non-reducing loading buffer (15 µL). An aliquot of each mixture (15 µL) was loaded into a precast gel (15% Tris-HCl). The gel was run (200 mV, 30 min), analyzed by fluorescence (488 nm excitation, 532 nm emission), stained (1 h), and destained (2 h). The results appear in Figure S3.

Comparing the amount of fluorescence incorporated into uPA by increasing concentrations of compound 1 (lanes 4-7) shows that increasing the equivalents of chloromethyl ketone beyond one equivalent does not substantially increase the amount of attachment to the protein, but rather just increases the amount of compound 1 that remains unreacted (as in Lane 2). Furthermore, treating other proteins with compound 1 (Lanes 9-10) does not cause substantial covalent attachment. These data are consistent with the hypothesis that one equivalent of compound 1 selectively attaches to the active site of uPA rather than all the compound 1 randomly attaching nonselectively to ubiquitous protein functional groups.

ELISA
General Procedures:
  Washing: The incubating solution was flicked out of the plate, and remaining liquid was removed by firmly pounding the plate upside-down five times onto a paper towel. Washing solutions (200 µL) were added to each well and removed by the same procedure. The subsequent incubation solution was added immediately.
ELISA Procedure:
  Coating: To each well was added a solution in the coating buffer of rabbit IgG anti human urokinase antibody (3 µg/mL, 200 µL). The plate was sealed with tape, allowed to stand (12 h), washed with PBS-tween (3×200 µL) and PBS (1×200 µL), loaded with PBS (200 µL), sealed, allowed to stand (2 h), and washed with PBS-tween (2×200 µL).
  ARM-U$_{Fluor}$ Preincubation: A solution in 2× HEPES/saline (750 µL) of urokinase (3 µg, 55 pmol, 75 nM) was prepared. A solution in water (211 µL) of compound 1 (4 µg, 3.4 nmol, 16 µM) was prepared. Into four microcentrifuge tubes were added 100 µL of either the urokinase solution or buffer and 100 µL of either the compound 1 solution or water (giving a final uPA concentration of 37 nM and a final compound 1 concentration of 8 µM). The solutions were gently mixed, allowed to stand (1 h, in the dark), and diluted with the protein-loading buffer (30 mL).
  uPA Loading: To each well was added 150 µL of the preincubated urokinase solution (13 ng/mL final uPA concentration). The plate was sealed, allowed to stand (2 h), and washed with PBS-tween (4×200 µL).
  Primary Antibody: Several solutions in the antibody-loading buffer of goat IgG anti-fluorescein antibody were prepared by serial dilution (final concentrations from 15 µg/mL=100 nM to 150 pg/mL=1 pM). To each well was added 150 µL of the appropriate solution or of pure antibody-loading buffer as a negative control. The plate was sealed, allowed to stand (2 h), and washed with PBS-tween (4×200 µL).
  Secondary Antibody: A solutions in the antibody-loading buffer of rabbit anti-goat-IgG antibody conjugated with alkaline phosphatase was prepared (final concentration 0.4 µg/mL). To each well was added 150 µL of this solution. The plate was sealed, allowed to stand (2 h), and washed with PBS-tween (3×200 µL) and the reported buffer (3×200 µL).
  Reporting: To each well was added 150 µL of the substrate solution. The plate was allowed to stand for 10 min, and the 405 nm absorbance was measured at five-minute intervals (10, 15, 20, and 25 min) on an automated plate reader.
  Analysis: Each condition was run in triplicate. For each well, measurements showed a linear increase in the 405 nm absorbance over time (resulting from production of para-nitrophenol under substrate-saturation conditions). These data are set forth in Figure S4.

The rate of increase of 405 nm absorbance in each well was calculated (Prism software), and mean slopes and standard deviations were calculated from the triplicate experiments at each concentration of anti fluorescein antibody. The slopes from the experiments without compound 1 (negative controls) were subtracted from the slopes from the experiments with compound 1 to remove the background binding, which was significant only at the highest antibody concentrations. From the resulting sigmoid-shaped curve, the dissociation constant was estimated graphically. Figures S5 and S6 show these analyses.

Cell Culture
General Procedures:
  Cell Counting: A cell suspension (10 µL) was diluted in Trypan blue (0.4%, 90 µL). 10 µL of this mixture was loaded onto a hemocytometer. Live cells were counted visually under 10× magnification.
  EDTA Detachment: Adherent cells were aspirated and washed with DPBS (5 mL). To the flask was added the EDTA detachment solution (5 mL). The flask was incubated (15 min). Cells were fully detached by gently rinsing the solution over the bottom of the flask. The cell suspension was pelleted, aspirated, suspended in media, and split as desired into new flasks.
  Incubations were done at 37° C. in a moist atmosphere supplemented with 5% $CO_2$.
  Pelleting was done by centrifuge for 5 minutes at 1100 rpm.

Cell Lines:
All cell lines were grown in an incubator (37° C.) supplemented with 5% $CO_2$. Media was changed approximately every 4 days. Cells were split approximately 4:1. Cells were not grown beyond approximately 30 passages.

A172 human glioblastoma cells were purchased from ATCC (#CRL-1620), grown in T-flasks with Dulbecco's modified Eagle's medium supplemented with 10% HI-FBS, and detached by the EDTA detachment procedure.

HT-29 human colon adenocarcinoma cells were purchased from ATCC (#HTB-38), grown in T-flasks with McCoy's 5A medium supplemented with 10% HI-FBS, and detached by the EDTA detachment procedure.

U937 Cells were purchased from ATCC (#CRL-1593.2), grown in Petri dishes as a suspension with RPMI-1640 medium supplemented with 10% HI-FBS and 1% penicillin-streptomycin.

Flow Cytometry
General Procedures:
Washing: Beginning with aspirated cells in a Eppendorf or Falcon tube, the washing solution was added by pipette. Cells were mixed either by gently flicking the outside of the tube by hand or by mixing the suspension by pipette. Cells were pelleted and aspirated by pipette.

Flow Cytometry Procedure:
Compound 1 incubation: 2× hepes/saline buffer (1 mL) was diluted to 1.6× by adding water (0.25 mL). The following stock solutions were prepared.

| Compound | Concentration | Solvent |
|---|---|---|
| HMW uPA | 6.0 μg/4.0 μL | water |
| LMW uPA | 3.7 μg/4.0 μL | water |
| compound 1 | 7 μg/255 μL | 1.6× HEPES/saline buffer |

To each uPA solution was added 7.1 μL of the compound 1 solution (final volume=11.1 μL, uPA final concentration=10 μM, compound 1 final concentration=15 μM). The solutions were mixed and maintained in the dark (1 h). Each uPA solution was diluted with the flow incubation buffer by serial dilution to make the following dilutions:

| uPA Amount | Volume | uPA Concentration |
|---|---|---|
| 10 pmol | 1 mL | 10 nM |
| 3 pmol | 1 mL | 3 nM |
| 1 pmol | 1 mL | 1 nM |
| 240 fmol | 1 mL | 240 pM |
| 240 fmol | 3 mL | 80 pM |
| 240 fmol | 10 mL | 24 pM |

Detachment: HT-29 cells (approximately 80% confluent) were detached from their flask by the EDTA-detachment procedure. The cells were transferred into a Falcon tube and counted (approximately 10 million cells). Aliquots containing approximately 250,000 cells were transferred into Eppendorf or Falcon tubes (depending on the required volume for incubations), and cells were pelleted and aspirated.

ARM-U Incubation: Cells were suspended in the appropriate uPA solution and allowed to stand at ambient temperature in the dark (1 h). Cells were pelleted, aspirated, and washed with DPBS (0.5 mL). Cells in Falcon tubes were transferred to Eppendorf tubes.

Primary Antibody Incubation: Rabbit IgG anti-fluorescein antibody (1 μg/μL, 6 μL=6 μg) was diluted in the flow incubation buffer (final volume=6 mL, final antibody concentration=1 μg/mL). 250 μL of this solution was added to each tube, the cells were suspended, and the suspensions were allowed to stand (4° C., 30 min) in the dark. Cells were pelleted, aspirated, and washed with cold DPBS (0.5 mL).

Secondary Antibody Incubation: Alexa-Fluor-488-conjugated Donkey anti-rabbit-IgG antibody (2 μg/μL, 9 μL=18 μg) was diluted in the flow incubation buffer (final volume=6 mL, final antibody concentration=3 μg/mL). 250 μL of this solution was added to each tube, the cells were suspended, and the suspensions were allowed to stand (4° C., 30 min) in the dark. Cells were pelleted, aspirated, and washed with cold DPBS (0.5 mL).

Flow Cytometry: DPBS (0.25 mL) was added to each tube. Immediately before analysis, a solution of propidium iodide (500 μg/mL, 20 μL) was added, and the cells were suspended by pipette and analyzed by flow cytometry.

Data analysis: For each experiment 10,000 events were counted. Forward and side scatter plots were optimally gated to remove debris particles and cellular aggregates. The FL-3 channel was gated to omit dead cells (whose FL-3 signal is greater than approximately $10^6$). Figure S7 shows the crude data distributions for some key conditions. Although fluorescein and Alexa Fluor 488 both fluoresce in the FL1 channel, the Alexa-Fluor-488-conjugated antibody significantly increases the signal relative to fluorescein. Control experiments without antibodies gave <10% of the corresponding increase in FL1 signals. The geometric means of the FL-1H signals were calculated (FlowJo software). Figure S8 shows these calculations.

A subsequent experiment was performed to assess the specificity with which ARM-$U_{Fluor}$ targets the cells via the uPAR receptor. The following conditions were tested.

| Condition | Anti-uPAR Blocking | ARM-$U_{Fluor}$ | Primary Antibody | Secondary Antibody |
|---|---|---|---|---|
| positive control | none | 1 nM | rabbit anti-fluorscein | donkey anti-rabbit |
| no ARM-$U_{Fluor}$ | none | none | rabbit anti-fluorscein | donkey anti-rabbit |
| isotype control | none | 1 nM | rabbit anti-DNP | donkey anti-rabbit |
| low blocking | 5 μg/mL goat anti-uPAR | 1 nM | rabbit anti-fluorscein | donkey anti-rabbit |
| high blocking | 20 μg/mL goat anti-uPAR | 1 nM | rabbit anti-fluorscein | donkey anti-rabbit |

Compound 1 incubation: Compound 1 and HMW uPA were mixed as described above. After the 1-hour incubation, the mixture was diluted with the flow incubation buffer to a final concentration of 1 nM uPA and cooled on ice.

Detachment: HT-29 cells (approximately 70% confluent) were detached from their flask by the EDTA-detachment procedure. The cells were transferred into a Falcon tube and counted. Five aliquots containing approximately 750,000 cells were transferred into Falcon tubes, and cells were pelleted and aspirated.

Anti-uPAR Blocking: Goat anti-uPAR antibody (0.2 μg/μL, 10 or 40 μL=2 or 8 μg) was diluted in the flow incubation buffer (400 μL, final antibody concentration=5 or 20 μg/mL). Cells were suspended in 400 uL of either the high or the low concentration of the anti-uPAR solution or buffer. Cell suspensions were maintained on ice (30 min), pelleted, aspirated, and washed with DPBS (1 mL).

ARM-U Incubation: Cells were suspended in the uPA solution (800 μL) or buffer. Cells were and maintained on ice in the dark (30 min), pelleted, aspirated, and washed with DPBS (1 mL).

Primary Antibody Incubation: Rabbit IgG anti-fluorescein antibody (1 μg/μL, 10 μL=10 μg) was diluted in the flow incubation buffer (final volume=4 mL, final antibody concentration=2.5 μg/mL). Rabbit IgG anti-DNP antibody (2 μg/μL, 2.5 μL=5 μg) was diluted in the flow incubation buffer (final volume=2 mL, final antibody concentration=2.5 g/mL). Cells were suspended in on of these solutions (790 μL), aliquots (250 μL) were transferred into Eppendorf tubes, and the suspensions were maintained on ice (30 min) in the dark. Cells were pelleted, aspirated, and washed with DPBS (0.3 mL).

Secondary Antibody Incubation: Alexa-Fluor-488-conjugated donkey anti-rabbit-IgG antibody (2 μg/L, 10 μL=20 μg) was diluted in the flow incubation buffer (final volume=5 mL, final antibody concentration=4 μg/mL). 250 μL of this solution was added to each tube, the cells were suspended, and the suspensions were maintained on ice (30 min) in the dark. Cells were pelleted, aspirated, and washed with cold DPBS (0.3 mL).

Flow Cytometry: DPBS (0.25 mL) was added to each tube. Immediately before analysis, a solution of propidium iodide (500 μg/mL, 20 μL) was added, and the cells were suspended by pipette and analyzed by flow cytometry.

Data analysis: For each experiment 10,000 events were counted. Forward and side scatter plots were optimally gated to remove debris particles and cellular aggregates. The FL-3 channel was gated to omit dead cells (whose FL-3 signal is greater than approximately $10^6$). The geometric means of the FL-1H signals were calculated (FlowJo software). Figure S9 shows these calculations.

The data show that using either the high or the low concentration of anti-uPAR antibody to block the uPAR on the surface of the cells results in a reduction of the flow cytometry signal, causing the output signal to be essentially equal to the signal observed when ARM-U$_{Fluor}$ is omitted. These results suggest that all the output signal in the positive control condition results from ARM-U$_{Fluor}$ specifically binding to uPAR on the cellular surface, rather than from non-specific binding. Furthermore, substituting an isotype-matched anti-DNP antibody for the anti-fluorescein antibody also reduces the signal to near the background level, which further supports that the observed signal is due to a specific interaction between ARM-U$_{Fluor}$ and the anti-fluorescein antibody.

| Condition | Anti-uPAR Blocking | ARM-U$_{Fluor}$ | Primary Antibody | Secondary Antibody Alexa Fluor 488 Conjugate |
|---|---|---|---|---|
| positive control | none | 1 nM | rabbit anti-fluorscein | donkey anti-rabbit |
| No ARM-U$_{Fluor}$ | none | none | rabbit anti-fluorscein | donkey anti-rabbit |
| isotype control | none | 1 nM | rabbit anti-DNP | donkey anti-rabbit |
| low blocking | 5 μg/mL goat anti-uPAR | 1 nM | rabbit anti-fluorscein | donkey anti-rabbit |
| high blocking | 20 μg/mL goat anti-uPAR | 1 nM | rabbit anti-fluorscein | donkey anti-rabbit |

Phagocytosis Assay (ADCP)

Target cell passing: Two days before the experiments, a plate of target cells (A172 or HT-29, 60-80% confluent) was passed into a new flask.

Effector cell priming: Two days before the experiments, a plate of U937 cells (approximately 60% confluent) was passed into a new Petri dish (10 mL colored ADCP media total volume). IFN-γ (5 μL, 1 μg/mL in DPBS) was added, and the cells were maintained in an incubator (37° C., 24 h). The cells were transferred into a Falcon tube, and DiD (19 uL, final concentration=1.9 μM) was added. The cells were maintained in an incubator (37° C., 30 min), pelleted, aspirated, resuspended in colored ADCP media (10 mL), and split equally into two Petri dishes. To each dish were added additional colored ADCP media (5 mL) and IFN-γ (5 μL, 1 μg/mL in DPBS), and the cells were maintained in an incubator (37° C., 24 h).

| Compound | Concentration | Solvent |
|---|---|---|
| HMW uPA | 6.0 μg/4.0 μL | water |
| LMW uPA | 3.7 μg/4.0 μL | water |
| compound 1 | 4 μg/145 μL | 1.6× HEPES/saline buffer |
| compound 2 | 4 μg/172 μL | 1.6× HEPES/saline buffer |

ARM-U formation: 2× HEPES/saline buffer (1 mL) was diluted to 1.6× by adding water (0.25 mL). The following stock solutions were prepared. (In each day of experiments either compound 1 or compound 2 was used.)

To each uPA solution was added 7.1 μL of the chloromethyl ketone solution (final volume=11.1 μL, uPA final concentration=10 μM, final chloromethyl ketone concentration=15 M). The solutions were mixed and maintained in the dark (1 h). Each uPA solution was diluted with the flow incubation buffer by serial dilution to give the following final uPA concentrations: 100 nM, 10 nM, 1 nM, 0.1 nM.

Target cell preparation: To a plate of target cells (60-80% confluent, either HT-29 or A172, 10 mL total media volume) was added DiO (20 μL, final concentration=2 μM). The cells were maintained in an incubator (37° C., 30 min), aspirated, and washed with colored ADCP media (3×10 mL). colored ADCP media (10 mL) was added. The cells were maintained in an incubator (37° C., 2 h), detached, split in to the required number of Falcon tubes, pelleted, aspirated, and resuspended in 1 mL of either one of the stock solutions of the ARM-U complexes (described above) or a stock solution of 2,4,6-trinitrophenylsulfonic acid (2 µL of a 5% solution in methanol, diluted in 1 mL colored ADCP media, final concentration=340 µM) or fluorescein isothiocyanate (10 µL of 1 µg/mL in DPBS, plus 10 mL DPBS, final concentration=2.6 nM) as a positive control or the flow incubation buffer as a negative control. The cells were allowed to stand at ambient temperature (30 min), pelleted, aspirated, washed with color-free ADCP media (3×10 mL), pelleted, resuspended in color-free ADCP media (1 mL), counted, and diluted with color-free ADCP media to give a final concentration of 250,000 cells per mL.

Effector cell preparation: Both dishes of primed U937 cells were transferred into a Falcon tube, pelleted, aspirated, resuspended in color-free ADCP media (10 mL), counted, and diluted with color-free ADCP media to give a final concentration of 4 million cells per mL.

Phagocytosis: All conditions were run in triplicate. For each experiment, into a sterile 2 mL Eppendorf tube were added color-free ADCP media (20 µL), either rabbit IgG anti-DNP antibody (0.625 µL, 2 mg/mL) or rabbit IgG anti-fluorescein antibody (1.25 µL, 1 mg/mL) or neither, target cells (50 µL=12,500 cells), and effector cells (50 µL=200,000 cells), to give an effector-to-target ratio of 16:1 and a final antibody concentration of 10 µg/mL. Tubes were gently agitated by hand, maintained at 4° C. (30 min), and gently agitated again. The cells were pelleted (2 min, 1100 rpm). The tubes were opened, covered with parafilm, pierced three times each with a 22 gauge needle, maintained in an incubator (37° C., 1 h), resuspended by briefly agitating with a vortex, and analyzed by flow cytometry.

Data analysis: For each experiment 100,000 events were counted. Forward and side scatter plots were optimally gated to remove debris particles and cellular aggregates. On a plot of FL-1 vs FL-4, the following populations were counted.

| Population | Approximate FL-1 Signal | Approximate FL-4 Signal |
|---|---|---|
| Effector Cells | $10^3$-$10^4$ | $10^5$-$10^{6.5}$ |
| Target Cells | $10^5$-$10^7$ | $10^{2.5}$-$10^4$ |
| Double Positive Cells | $10^5$-$10^7$ | $10^5$-$10^{6.5}$ |

Phagocytosis was calculated by the following formula. Figure S10 shows these data.

$$\% \text{ phagocytosis} = \frac{\text{(double positive cells)}}{\text{(remaining target cells)} + \text{(double positive cells)}} \times 100$$

A subsequent experiment was performed by the same procedure, except using commercially available serum from rabbits immunized against DNP-KLH (final concentration=0.5%) instead of 10 µg/mL rabbit IgG anti-DNP. Figure S11 shows these data.

Cytotoxicity Assay (ADCC)

Target cell seeding: One day before the experiment, A172 cells were detached, counted, aspirated, and diluted in FBS ADCC media (to a final concentration of 25,000 cells/mL). Into each well of an E-plate was added 200 µL of the cell suspension (5,000 cells). The plate was allowed to stand at ambient temperature (30 min) and maintained in an incubator (37° C., 12 h).

Growth curves: The xCelligence system was maintained inside the incubator (37° C.). An E-plate containing 100 µL FBS ADCC media per well was used for obtaining background measurements. The seeded E-plate was placed in the port, and cell index readings were obtained (every 2 min for 30 min) to confirm that the cells had adhered properly.

ARM-U formation: 2× HEPES/saline buffer (1 mL) was diluted to 1.6× by adding water (0.25 mL). The following stock solutions were prepared.

| Compound | Concentration | Solvent |
|---|---|---|
| HMW uPA | 6.0 µg/4.0 µL | water |
| compound 2 | 4 µg/259 µL | 1.6× HEPES/saline buffer |

To each uPA solution or 64 µL of the uPA buffer was added 7.1 µL of either water or the chloromethyl ketone solution (final volume=11.1 µL, uPA final concentration=10 µM, final chloromethyl ketone concentration=10 µM). The solutions were mixed, maintained in the dark (1 h), and diluted with FBS-free ADCC media (544 µL, to a final uPA concentration of 200 nM). For the 5 nM experiment, these solutions were diluted another 10-fold in FBS-free ADCC media (to a final concentration of 20 nM)

Experimental setup: Either rabbit IgG anti-DNP (2 mg/mL stock) or rabbit IgG anti-GFP (2 mg/mL stock) were added to the ARM-U solutions to give final concentrations of 108 µg/mL antibody. Supernatant (100 µL) was removed from each well of the E-plate to make room for reagent addition. Solutions of ARM-U and antibody (50 µL) were added to each well (giving final concentrations of 50 or 5 nM uPA or ARM-U and 27 µg/mL antibody). The E-plate was returned to the port, and cell index readings were obtained (every 2 min for 90 min)

PBMC isolation: Fresh blood (50 mL, stabilized with sodium heparin) was obtained from a healthy volunteer on the day of the experiment. Into each of two Falcon tubes were added first Lympholyte Poly (25 mL) and then blood (25 mL) gently on top. The tubes were centrifuged (0.5 rcf, 35 min). The top (pale yellow) layer was removed, and the top layer of cells was isolated, diluted with Hank's balanced salt solution, counted, pelleted (0.2 ref, 15 min), aspirated, and diluted in FBS-free ADCC media (to a final concentration of 6.25 million cells per mL). 50 µL of this suspension (312,500 cells, 62.5:1 effector:target) was added to each well of the E-plate. The E-plate was returned to the port, and cell index readings were obtained (every 2 min for 20 h, 37° C.).

Data analysis: Cell index readings were normalized (RTCA software) at the timepoint immediately after addition of the PBMCs. Figure S12 shows these data. Values from the 3-hour time point were used to calculate specific killing. Normal growth was defined as that shown by target A172 cells treated with effector cells and anti-DNP antibody, but no uPA or ARM-U constructs. Specific killing was calculated as the following formula. Figure S13 shows these data.

$$\% \text{ specific killing} = 100 - \frac{\text{(cell index)}}{\text{(normal growth cell index)}} \times 100$$

Interestingly, increases in cell index were observed during the first 5 hours after treatment of A172 cells with negative control conditions including uPA plus anti-DNP, ARM-U$_{DNP}$ plus isotype control anti-GFP, and ARM-U$_{DNP}$ without antibody. We speculate that these observations reflect morphological changes in the adherent cells, which are known to be caused by the uPA-uPAR interaction[6] and are known to be measurable by the xCelligence System[7]. For the conditions with ARM-U$_{DNP}$ plus anti-DNP (blue), on the other hand, a dramatic decrease in cell index is observed within the first 3 hours, and therefore this effect is specific to the combination of ARM-U$_{DNP}$ and an isotope-matched antibody.

[6] Blasi, F., Carmeliet, P. (2002) *Nat. Rev. Mol. Cell. Biol.* 3, 932.

[7] Yu, N., Atienza, J. M., Bernard, J., Blanc, S., Zhu, J., Wang, X., Xu, X., Abassi, Y. A. (2006) *Anal. Chem.* 78, 35.

A subsequent experiment was performed using an analogous procedure, but omitting the PBMC effector cells. Cell index readings were normalized (RTCA software) at the timepoint immediately after addition of ARM-U. Figure S14 shows these data. Values from the 3-hour time point were used to calculate specific killing. Normal growth was defined as that shown by target A172 cells treated with anti-DNP antibody, but no uPA or ARM-U constructs. Specific killing was calculated in the same way. Figure S14 shows these data.

Consistent with the previous experiments, conditions with high ARM-U concentrations cause initial increases in the cell index over the first 4 hours, followed by gradual decreases in cell index. There is no significant difference between 50 nM ARM-U$_{DNP}$ with or without antibody (dark blue vs red), which shows that in the absence of PBMCs there is no effect that is specific to the combination of ARM-U$_{DNP}$ and matched antibody, and which further shows that the results observed in the experiments with PBMCs do require the presence of the PBMCs.

ADCP Flow Cytometry Data

The first gating, to omit small debris particles and any large cell aggregates, was performed on a plot of forward scatter versus side scatter. All conditions were gated in the same way. Figure S16 shows a representative example. The second gating, used to identify phagocytosed target cells and remaining target cells, was performed on a plot of channel 1 fluorescence (FL1) versus channel 4 fluorescence (FL4). Figure S17 shows a representative example with the populations labeled for clarity.

Triplicate ADCP flow cytometry data, evidenced the activity of compounds 1 and 2 against cancer cells through a mechanism of phagocytosis of cancer cells.

REFERENCES

[i] Jemal, A., Siegel, R., Xu, J., Ward, E. (2010) Cancer statistics 2010, *CA Cancer J Clin.* 60, 277-300.

[ii] Garbe, C., Eigentler, T. K., Keilholz, U., Hauschild, A., Kirkwood, J. M. (2011) Systematic review of medical treatment in melanoma: current status and future prospects, *The Oncologist* 16, 5-24.

[iii] Boyle, P., Levin, B., Eds. (2008) *World Cancer Report 2008*, pp 438-443, International Agency for Research on Cancer, Lyon.

[iv] Andreasen, P. A., Kjoller, L., Christensen, L., Duffy, M. J. (1997) The urokinase-type plasminogen activator system in cancer metastasis: A review, *Int. J. Cancer* 72, 1-22.

[v] Duffy, M. J. (1993) Urokinase-type plasminogen activator and malignancy, *Fibrinolysis* 7, 295-302.

[vi] Saksela, O., Rifkin, D. B. (1988) Cell-associated plasminogen activation: Regulation and physiological functions, *Ann. Rev. Cell. Biol.* 4, 93-126.

[vii] Del Rosso, M., Fibbi, G., Pucci, M., D'Alessio, S. A., Del Rosso, A., Magnelli, L., Chiarugi, V. (2002) Multiple pathways of cell invasion are regulated by multiple families of serine proteases, *Clin. & Exp. Metastasis* 19, 193-207.

[viii] Jessani, N., Liu, Y., Humphrey, M., Cravatt, B. F. (2002) Enzyme activity profiles of the secreted and membrane proteome that depict cancer cell invasiveness. *Proc. Natl. Acad. Sci. U.S.A.* 99, 10335-10340.

[ix] Romer, J., Nielsen, B. S., Ploug, M. (2004) The urokinase receptor as a potential target in cancer therapy, *Curr. Pharm. Des.* 10, 2359-2376.

[x] Blasi, F., Carmeliet, P. (2002) uPAR: A versatile signaling orchestrator, *Nat. Rev. Mol. Cell. Biol.* 3, 932-943.

[xi] Duffy, M. J. (1996) Proteases as prognostic markers in cancer *Clin. Cancer. Res.* 1996, 2, 613-618.

[xii] Dano, K., Behrendt, N., Brunner, N., Ellis, V., Ploug, M., Pyke, C. (1994) The urokinase receptor: Protein structure and role in plasminogen activation and cancer invasion, *Fibrinolysis* 8 suppl 1, 189-203.

[xiii] Quax, P. H. A., van Muijen, G. N. P., Weening-Verhoeff, E. J. D., Lund, L. R., Dano, K., Ruiter, D. J., Verheijen, J. H. (1991) Metastatic Behavior of human melanoma cell lines in nude mice correlates with urokinase-type plasminogen activator, its type-1 inhibitor, and urokinase-mediated matrix degradation, *J Cell. Biol.* 115, 191-199.

[xiv] Madsen, M. A., Deryugina, E. I., Niessen, S., Cravatt, B. F., Quigley, J. P. (2006) Activity-based protein profiling implicates urokinase activation as a key step in human fibrosarcoma intravasation, *J. Biol. Chem.* 281, 15997-16007.

[xv] Sier, C. F., Stephens, R., Bizik, J., Mariani, A., Bassan, M., Pedersen, N., Frigerio, L., Ferrari, A., Dano, K., Brünner, N., Blasi, F. (1998) The level of urokinase-type activator receptor is increased in serum of ovarian cancer patients, *Cancer Res.* 58, 1843-1849.

[xvi] Harbeck, N., Kates, R. E., Gauger, K., Willems, A., Kiechle, M., Magdolen, V., Schmitt, M. (2004) Urokinase-type plasminogen activator (uPA) and its inhibitor PAI-1: Novel tumor-derived factors with a high prognostic and predictive impact in breast cancer, *Thromb. Haemost.* 91, 450-456.

[xvii] Duffy, M. J., O'Grady, P., Devaney, D., O'Siorain, L., Fennelly, J. J., Lijnen, H. J. (1998) Urokinase-plasminogen activator, a marker for aggressive breast carcinomas, *Cancer* 62, 531-533.

[xviii] Herszenyi, L., Plebani, M., Carraro, P., de Paoli, M., Roveroni, G., Cardin, R., Tulassay, Z., Naccarato, R., Farinati, F. (1999) The role of cystein and serine proteases in colorectal carcinoma, *Cancer* 86, 1135-1142.

[xix] Harvey, S. R., Hurd, T. C., Markus, G., Martinick, M. I., Penetrante, R. M., Tan, D., Venkataraman, P., DeSouza, N., Sait, S. N. J., Driscoll, D. L., Gibbs, J. F. (2003) Evaluation of urinary plasminogen activator, its receptor, matrix metalloproteinase-9 and von Willebrand factor in pancreatic cancer, *Clin. Cancer Res.* 9, 4935-4943.

[xx] Konecny, G., Untch, M., Pihan, A., Kimmig, R., Gropp, M., Stieber, P., Hepp, H., Slamon, D., Pegram, M. (2001) Association of urokinase-type plasminogen activator and its inhibitor with disease progression and prognosis in ovarian cancer, *Clin. Cancer Res.* 7, 1743-1749.

[xxi] Schmitt, M., Wilhelm, O. G., Reuning, U., Krüger, A., Harbeck, N., Lengyel, E., Graeff, H., Gänsbacher, B., Kessier, H. Bürgle, M., Stürzebecher, J., Sperl, S. Mag-

[xxi] dolen, V. (2000) The urokinase-type plasminogen activator system as a novel target for tumor therapy, *Fibrinolysis & Proteolysis* 14, 114-132.

[xxii] Ertongur, S., Lang, S., Mack, B., Wosikowski, K., Muehlenweg, B., Gires, O. (2004) Inhibition of the invasion capacity of carcinoma cells by WX-UK1, a novel synthetic inhibitor of the urokinase-type plasminogen activator system, *Int. J. Cancer* 2004, 110, 815-824.

[xxiii] Ossowski, L., Reich, E. (1983) Antibodies to plasminogen activator inhibit human tumor metastasis, *Cell* 35, 611-619.

[xxiv] Liu, S., Aaronson, H., Mitola, D. J., Leppla, S. H., Bugge, T. H. (2003) Potent antitumor activity of a urokinase-activated engineered anthrax toxin, *Proc. Natl. Acad. Sci. U.S.A.* 100, 657-662.

[xxv] Min, H. Y., Doyle, L., V., Vitt, C. R., Zandonella, C. L., Stratton-Thomas, J. R., Shuman, M. A., Rosenberg, S. (1996) Urokinase receptor antagonists inhibit angiogenesis and primary tumor growth in syngeneic mice, *Cancer Res.* 56, 2428-2433.

[xxvi] Vallera, D. A., L1, C., Jin, N., Mortari-Panoskaltsis, A., Hall, W. A. (2002) Targeting urokinase-type plasminogen activator receptor on human glioblastoma tumors with diphtheria toxin fusion protein DTAT, *J Natl. Cancer Inst.* 94, 597-606.

[xxvii] Spiegel, D. A. (2010) Synthetic immunology to engineer human immunity, *Nat. Chem. Biol.* 6, 871-872.

[xxviii] Murelli, R. P., Zhang, A. X., Michel, J., Jorgensen, W. L., Spiegel, D. A. (2009) Chemical control over immune recognition: A class of antibody-recruiting small molecules that target prostate cancer, *J. Am. Chem. Soc.* 131, 17090-17092.

[xxix] Lu, Y., Low, P. S. (2002) Folate targeting of haptens to cancer cell surfaces mediates immunotherapy of syngeneic murine tumors, *Cancer Immunol. Immunother.* 51, 153-162.

[xxx] Lu, Y., Sega, E., Low, P. S. (2005) Folate receptor-targeted immunotherapy: Induction of humoral and cellular immunity against hapten-decorated cancer cells, *Int. J Cancer* 116, 710-719.

[xxxi] Popkov, M., Gonzalez, B., Sinha, S. C., Barbas, C. F., III. (2009) Instant immunity through chemically programmable vaccination and covalent self-assembly *Proc. Natl. Acad. Sci. U.S.A.* 106, 4378-4383.

[xxxii] Carlson, C. B., Mowery, P., Owen, R. M., Dykhuizen, E. C., Kiessling, L. L. (2007) Selective tumor cell targeting using low-affinity, multivalent interactions, *ACS Chem. Biol.* 2, 119-127.

[xxxiii] Ortega, E., Kostovetzky, M., Larralde, C. (1984) Natural DNP-binding immunoglobulins and antibody multispecificity, *Mol. Immunol.* 21, 883-888.

[xxxiv] Kettner, C., Shaw. E. (1981) Inactivation of trypsin-like enzymes with peptides of arginine chloromethyl ketone, *Methods Enzymol.* 80, 826-842.

[xxxv] Spraggon, G., Phillips, C., Nowak, U. K., Ponting, C. P., Saunders, D., Dobson, C. M., Stuart, D. I., Jones, E. Y. (1995) The crystal structure of the catalytic domain of human urokinase-type plasminogen activator, *Structure* 3, 681-691.

[xxxvi] Williams, E. B., Krishnaswamy, S., Mann, K. G. (1989) Zymogen/enzyme discrimination using peptide chloromethyl ketones, *J. Biol. Chem.* 264, 7536-7545.

[xxxvii] Walker, B., Elmore, D. T. (1984) The behaviour of urokinase and porcine kidney cell plasminogen activator towards some synthetic peptides *Thromb. Res.* 34, 103-107.

[xxxviii] Binnema, D. J., van Iersel, J. J. L., Dooijewaard, G. (1986) Quantitation of urokinase antigen in plasma and culture media by use of an ELISA, *Thromb. Res.* 43, 569-577.

[xxxix] Rajagopal, V., Kreitman, R. J. (2000) Recombinant toxins that bind to the urokinase receptor are cytotoxic without requiring binding to the $\alpha_2$-macroglobulin receptor, *J. Biol. Chem.* 275, 7566-7573.

[xl] Bracher, M., Gould, H. J., Sutton, B. J., Dombrowicz, D., Karagiannis, S. N. (2007) Three-colour flow cytometric method to measure antibody-dependent tumour cell killing by cytotoxicity and phagocytosis, *J. Immunol. Methods* 323, 160-171.

[xli] Boltz-Nitulescu, G., Willheim, M., Spittler, A., Leutmezer. F., Tempfer, C., Winkler, S. (1995) Modulation of IgA, IgE, and IgG Fc receptor expression of human mononuclear phagocytes by $1\alpha,25$-dihydroxyvitamin $D_3$ and cytokines, *J. Leuko. Biol.* 58, 256-262.

[xlii] Lu, Yingjuan, Klein, P. J., Westrick, E., Xu, L.-C., Santhapuram, H. K. R., Bloomfield, A., Howard, S. J., Vlahov, I. R., Ellis, P. R., Low, P. S., Leamon, C. P. (2009) Strategy to prevent drug-related hypersensitivity in folate-targeted hapten immunotherapy of cancer, *AAPS J.* 2, 628-638.

[xliii] Kute, T. E., Savage, L., Stehle, J. R. Jr., Kim-Shapiro, J. W., Blanks, M. J., Wood, J., Vaughn, J. P. (2009) Breast tumor cells isolated from in vitro resistance to trastuzumab remain sensitive to trastuzumab anti-tumor effects in vivo and to ADCC killing, *Cancer Immunol. Immunother.* 58, 1887-1896.

[xliv] Zhu, J., Wang, X., Xu, X., Abassi, Y. A. (2006) Dynamic and label-free monitoring of natural killer cell cytotoxic activity using electronic cell sensor arrays, *J. Immunol. Methods* 309, 25-33.

[xlv] Weiner, G. J. (2007) Monoclonal antibody mechanisms of action in cancer, *Immunol. Res.* 39, 271-278.

The invention claimed is:

1. A method of lessening, suppressing or inhibiting cancer in a patient in need thereof, comprising administering to said patient an effective amount of a composition in pharmaceutical dosage form comprising an anti-cancer effective amount of a compound according to the chemical formula consisting of:

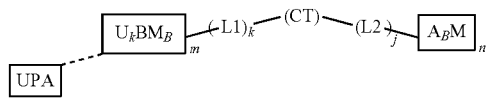

Wherein

UPA is a urokinase-type plasminogen activator (UPA);

$U_KBM_B$ is a UPA-binding motif covalently or non-covalently bound to UPA via a $U_KBM$ group;

said $U_KBM$ is a group according to the chemical formula:

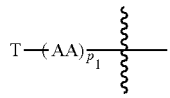

wherein T is a $R^e$ group or an amino acid group according to the chemical structure:

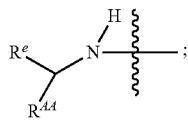

$R^{AA}$ is side chain of an amino acid;
$R^e$ is H or an electrophilic group which is reactive with a nucleophile in the active site of urokinase-type plasminogen activator (UPA) to produce a covalent bond or non-covalent bond interaction;
$p_1$ is an integer from 0 to 25; and
Each (AA) is independently a single amino acid residue;

$$A_BM$$

is an antibody binding moiety comprising a hapten which is capable of binding to an antibody in a patient or subject according to the chemical structure:

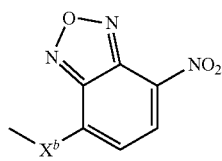

(a)

Wherein $X^b$ is a bond, O, $CH_2$ or $NR^1$ or S; and
$R^1$ is the same as above;
(b) A group according to the chemical structure:

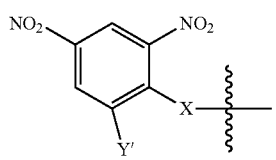

Wherein Y' is H or $NO_2$,
X is O, $CH_2$, $NR^1$, S(O), S(O)$_2$, —S(O)$_2$O, —OS(O)$_2$, or OS(O)$_2$O; and
$R^1$ is H, a $C_1$-$C_3$ alkyl group, or a —C(O) ($C_1$-$C_3$) group;
(c) A digalactose hapten moiety according to the chemical structure:

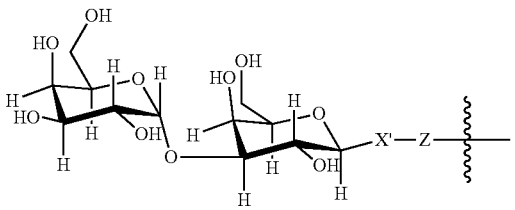

Wherein X' is $CH_2$, O, N—$R^{1'}$ or S;
$R^{1'}$ is H or $C_1$-$C_3$ alkyl; and
Z is a bond, a monosaccharide, disaccharide, oligosaccharide, glycoprotein or glycolipid; or
(d) A group according to the chemical structure:

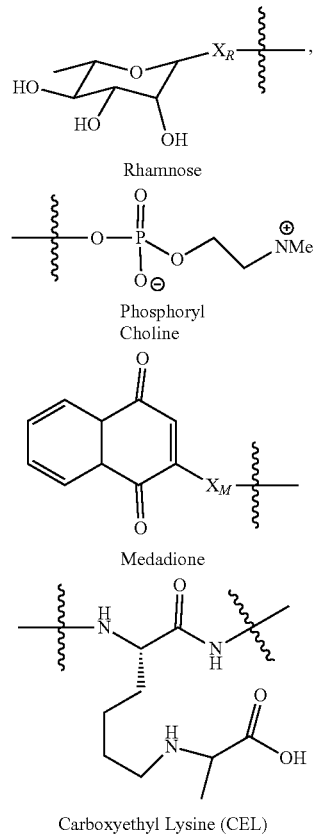

Rhamnose

Phosphoryl Choline

Medadione

Carboxyethyl Lysine (CEL)

Wherein $X_R$ is O or S; and
$X_M$ is O or S;
L1 is a linker molecule which chemically links $$U_kBM_B$$

to $$A_BM$$

via CT and L2 in said compound;

L2 is a linker molecule which chemically links

A_BM to

U_kBM_B via CT and L1 in said compound;
wherein L1 and L2 are each independently a group according to the chemical structure:
a group according to the chemical structure:

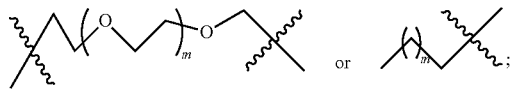

or a polypropylene glycol or polypropylene-co-polyethylene glycol linker containing between 3 and 75 alkyleneglycol units;

Each m of L1 or L2 is independently an integer selected from 3 to 75;

CT is a bond or a connector molecule;

Each j is independently 0, 1, 2, 3, 4 or 5;

Each k is independently 0, 1, 2, 3, 4 or 5, with the proviso that k and/or j are other than 0 when CT is a bond; and m of U_kBM_B is 1 and n of

A_BM is from 1 to 3; or a pharmaceutically acceptable salt, stereoisomer, solvate or polymorph thereof in combination with a pharmaceutically acceptable carrier, additive or excipient.

2. The method according to claim 1, wherein

U_kBM_B forms a covalent bond with

UPA wherein said $R^e$ is an electrophilic group according to the chemical formula:

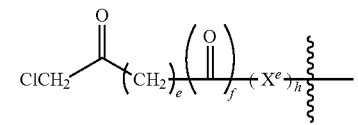

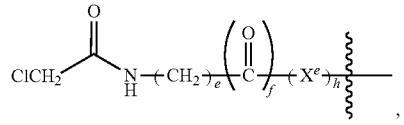

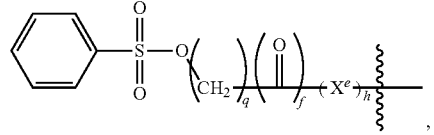

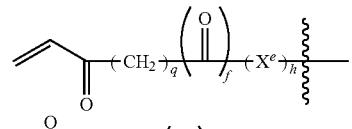

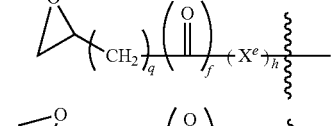

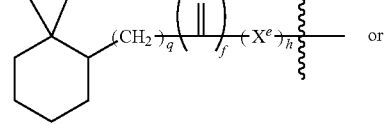

or

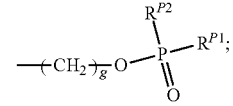

Wherein $X^e$ is O, S, or N—$R^{Xe}$;
$R^{Xe}$ is H or a $C_1$-$C_3$ alkyl or alkanol group;
$R^{P1}$ is any group which forms a stable linkage with phosphorous in the phosphonate moiety;
$R^{P2}$ is a halogen;
Each e is independently 0, 1, 2, 3, 4, 5 or 6;
Each f is independently 0 or 1;
Each g is 0, 1, 2, 3, 4, 5 or 6;
Each h is independently 0 or 1; and
Each q is independently 1, 2, 3, 4, 5, or 6.

3. The method according to claim 1, wherein $P_1$ is an integer from 1 to 10.

4. The method according to claim 3, wherein $P_1$ is an integer from 1 to 3.

5. The compound according to claim 3, wherein $P_1$ is 2 and each (AA) is an amino acid residue independently selected from the group consisting of glycine, alanine, leucine, isoleucine and threonine, glutamic acid, aspartic acid, serine and lysine.

6. The method according to claim 1, wherein $R^{AA}$ is a side chain of arginine or lysine.

7. The method according to claim 1, wherein $R^{AA}$ is arginine.

8. The method according to claim 1, wherein $R^e$ is

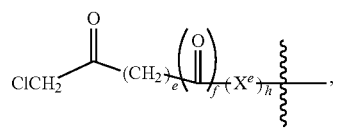

and e, f and h are each independently 0.

9. The method according to claim 3, wherein L1 and/or L2 is a group according to the chemical structure:

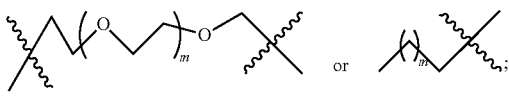

or a polypropylene glycol or polypropylene-co-polyethylene glycol linker containing between 3 and 75 alkyleneglycol units.

10. The method according to claim 3, wherein L1 and/or L2 is a polyethylene glycol linker containing from 4 to 75 ethylene glycol units.

11. The method according to claim 3, wherein said connector group CT is a group according to the chemical structure:

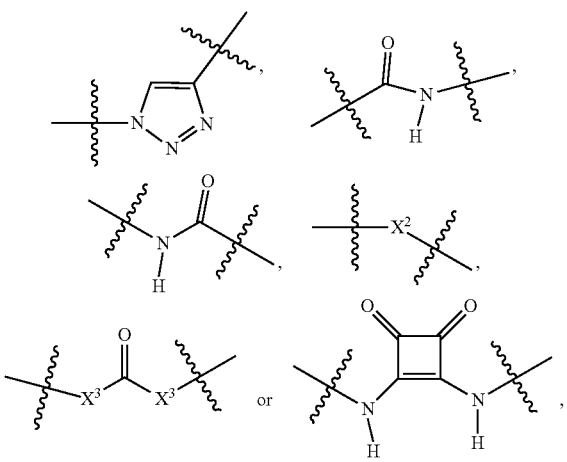

wherein $X^2$ is O, S, $NR^4$, S(O), $S(O)_2$, —$S(O)_2O$, —$OS(O)_2$, or $OS(O)_2O$;

$X^3$ is O, S or $NR^4$; and $R^4$ is H, a $C_1$-$C_3$ alkyl or alkanol group, or a —C(O)($C_1$-$C_3$) group.

12. The method according to claim 3, wherein CT is a triazole group.

13. The method according to claim 1, wherein said UPA is human recombinant urokinase.

14. The method according to claim 1, wherein said composition is formulated with an additional anticancer agent.

15. The method according to claim 1, wherein said composition is co-administered with an additional anticancer agent.

16. The method according to claim 14, wherein said additional anticancer agent is an antimetabolite, an inhibitor of topoisomerase I and II, an alkylating agent, a microtubule inhibitor or a mixture of distinct additional anticancer agents thereof.

17. The method according to claim 15, wherein said additional anticancer agent is an antimetabolite, an inhibitor of topoisomerase I and II, an alkylating agent, a microtubule inhibitor or a mixture of distinct additional anticancer agents thereof.

18. The method according to claim 14, wherein said additional anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an IGFR-TK inhibitor, an anti-HGF antibody, a PI3 kinase inhibitor, an AKT inhibitor, a JAK/STAT inhibitor, a checkpoint-1 or 2 inhibitor, a focal adhesion kinase inhibitor, a Map kinase (mek) inhibitor, a VEGF trap antibody or a mixture of distinct additional anticancer agents thereof.

19. The method according to claim 15, wherein said additional anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody or a mixture of distinct additional anticancer agents thereof.

20. The method according to claim 1, wherein said cancer is metastatic cancer.

* * * * *